(12) United States Patent
Turjman et al.

(10) Patent No.: US 9,445,828 B2
(45) Date of Patent: Sep. 20, 2016

(54) METHODS, DEVICES, AND SYSTEMS FOR POSTCONDITIONING WITH CLOT REMOVAL

(71) Applicant: Cognition Medical Corp., Cambridge, MA (US)

(72) Inventors: Alexis Turjman, Cambridge, MA (US); Jonah Bernstein, Cambridge, MA (US)

(73) Assignee: Cognition Medical Corp., Cambridge, MA (US)

( * ) Notice: Subject to any disclaimer, the term of this patent is extended or adjusted under 35 U.S.C. 154(b) by 107 days.

(21) Appl. No.: 13/844,728

(22) Filed: Mar. 15, 2013

(65) Prior Publication Data

US 2014/0155980 A1 Jun. 5, 2014

Related U.S. Application Data

(60) Provisional application No. 61/668,408, filed on Jul. 5, 2012.

(51) Int. Cl.
*A61F 2/06* (2013.01)
*A61B 17/221* (2006.01)
(Continued)

(52) U.S. Cl.
CPC ....... *A61B 17/221* (2013.01); *A61B 17/12031* (2013.01); *A61B 17/12036* (2013.01); *A61B 17/12109* (2013.01); *A61B 17/12136* (2013.01); *A61B 17/12172* (2013.01);
(Continued)

(58) Field of Classification Search
CPC .............. A61F 2/82; A61F 2/86; A61F 2/95; A61F 2/962; A61F 2/966; A61B 17/12136
See application file for complete search history.

(56) References Cited

U.S. PATENT DOCUMENTS

| 4,655,746 A | 4/1987 | Daniels et al. |
| 5,209,728 A * | 5/1993 | Kraus ................. A61M 25/104 604/913 |

(Continued)

FOREIGN PATENT DOCUMENTS

| EP | 0486720 A1 | 5/1992 |
| WO | WO-03018085 A2 | 3/2003 |

(Continued)

OTHER PUBLICATIONS

International Search Report and Written Opinion Issued by the U.S. Patent and Trademark Office as International Searching Authority for International Application No. PCT/US2013/049428 mailed Mar. 18, 2014 (24 pgs.).

(Continued)

*Primary Examiner* — Robert Lynch
(74) *Attorney, Agent, or Firm* — Wilmer Cutler Pickering Hale and Dorr LLP

(57) ABSTRACT

New devices, systems, and methods are disclosed for preventing, treating, and/or at least minimizing ischemia and/or reperfusion injury by restoring and/or modulating blood flow, particularly in the cerebral vasculature where blood vessels are narrow and tortuous. These devices, systems, and methods make it possible for a clinician to adequately and systematically restore blood flow to ischemic tissue while simultaneously modulating the blood flow to minimize reperfusion injury. New thrombectomy devices and systems, which, for example, expand with greater radial force, further enable improved binding with clots and restoration of blood flow.

14 Claims, 63 Drawing Sheets

(51) Int. Cl.

| | | |
|---|---|---|
| *A61B 17/12* | (2006.01) | |
| *A61B 17/3207* | (2006.01) | |
| *A61F 2/82* | (2013.01) | |
| *A61F 2/95* | (2013.01) | |
| *A61M 25/00* | (2006.01) | |
| *A61F 2/86* | (2013.01) | |
| *A61F 2/966* | (2013.01) | |
| *A61F 2/962* | (2013.01) | |
| *A61B 17/22* | (2006.01) | |

(52) U.S. Cl.
CPC ........ *A61B 17/320725* (2013.01); *A61F 2/82* (2013.01); *A61F 2/95* (2013.01); *A61M 25/0082* (2013.01); *A61B 2017/2215* (2013.01); *A61B 2017/22065* (2013.01); *A61F 2/86* (2013.01); *A61F 2/962* (2013.01); *A61F 2/966* (2013.01)

(56) References Cited

U.S. PATENT DOCUMENTS

| | | | |
|---|---|---|---|
| 5,321,340 | A | 6/1994 | Tamaki et al. |
| 6,231,588 | B1 | 5/2001 | Zadno-Azizi |
| 2001/0012951 | A1* | 8/2001 | Bates .................... A61F 2/013 606/200 |
| 2004/0006370 | A1 | 1/2004 | Tsugita |
| 2005/0107741 | A1 | 5/2005 | Willard et al. |
| 2010/0023106 | A1 | 1/2010 | Meyer et al. |
| 2010/0036410 | A1 | 2/2010 | Krolik et al. |
| 2010/0069826 | A1 | 3/2010 | Rabbitte et al. |
| 2011/0160742 | A1 | 6/2011 | Ferrera et al. |
| 2011/0172697 | A1 | 7/2011 | Jonsson |
| 2011/0288478 | A1 | 11/2011 | Ehrenreich et al. |

FOREIGN PATENT DOCUMENTS

| | | | | |
|---|---|---|---|---|
| WO | WO2008113372 | * | 9/2008 | .............. B81B 3/00 |
| WO | WO-2008113372 A2 | | 9/2008 | |

OTHER PUBLICATIONS

Pignataro, Giuseppe et al., "In vivo and in vitro characterization of a novel neuroprotective strategy for stroke: ischemic postconditioning," Journal of Cerebral Blood Flow & Metabolism, vol. 28, No. 2, pp. 232-241, No Month Listed 2008, 10 pages.

Roger, Veronique L. et al., "Heart Disease and Stroke Statistics—2012 Update: A Report From the American Heart Association," Circulation, vol. 125, pp. e2-e220, originally published online Dec. 15, 2011, retrieved from the internet on May 12, 2014 from [http://circ.ahajournals.org/], 225 pages.

Thomalla, Götz et al., "Two Tales: Hemorrhagic Transformation but Not Parenchymal Hemorrhage After Thrombolysis Is Related to Severity and Duration of Ischemia: MRI Study of Acute Stroke Patients Treated With Intravenous Tissue Plasminogen Activator Within 6 Hours," Stroke, vol. 38, No. 2, pp. 313-318, published online Jan. 4, 2007, retrieved from the Internet on May 12, 2014 from [http://stroke.ahajournals.org/], 7 pages.

Tsang, Andrew et al., "Myocardial postconditioning: reperfusion injury revisited," American Journal of Physiology—Heart and Circulatory Physiology, vol. 289, No. 1, pp. H2-H7, published Jul. 1, 2005, accessed May 12, 2014, 12 pages.

Zhao, Heng et al., "Interrupting reperfusion as a stroke therapy: ischemic postconditioning reduces infarct size after focal ischemia in rats," Journal of Cerebral Blood Flow & Metabolism, vol. 26, No. 9, pp. 1114-1121, published online May 31, 2006, 8 pages.

Extended European Search Report issued in 13812984.6, dated Dec. 18, 2015, 10 pages.

* cited by examiner

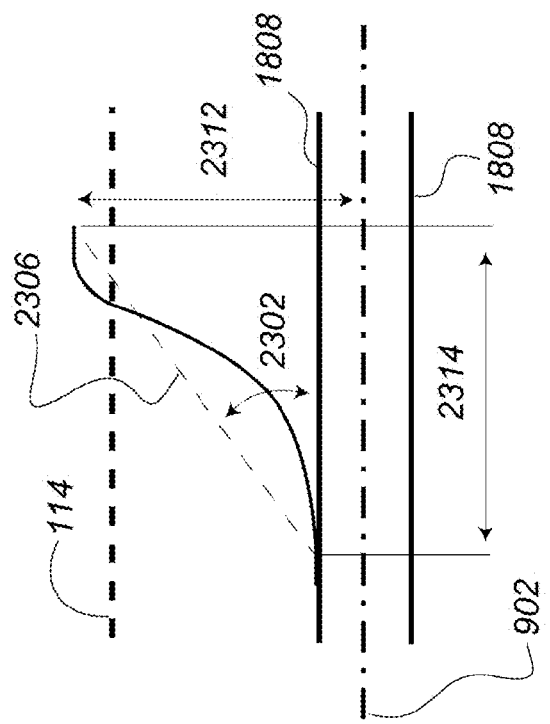
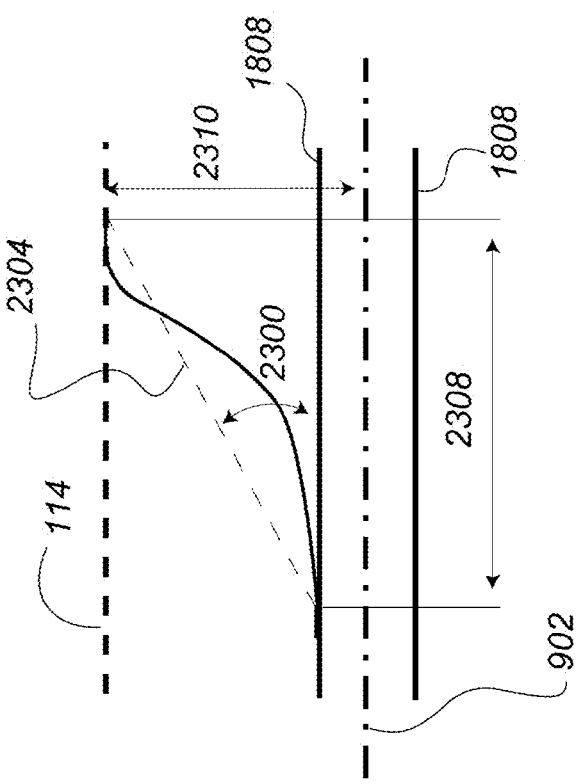
FIG. 23B
FIG. 23A

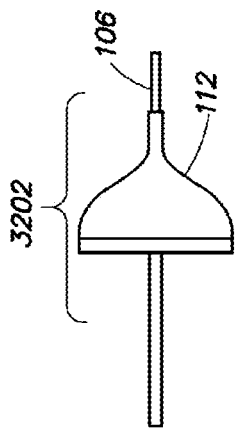
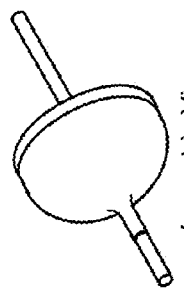
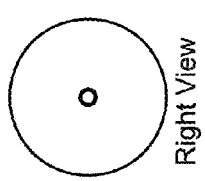
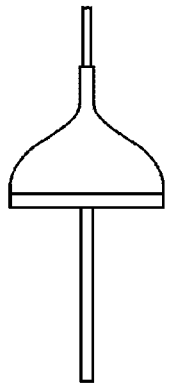
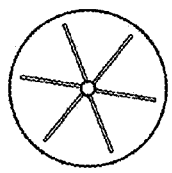
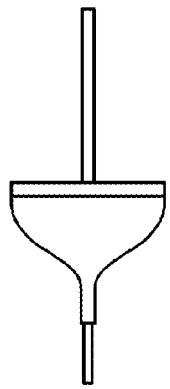
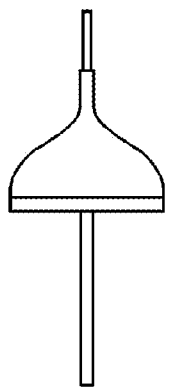
FIG. 32A Bottom View
FIG. 32B Isometric View
FIG. 32C Right View
FIG. 32D Front View
FIG. 32E Left View
FIG. 32F Rear View
FIG. 32G Top View

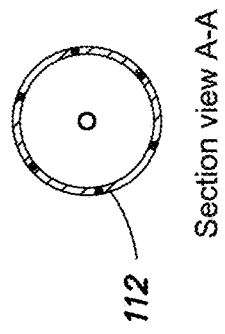
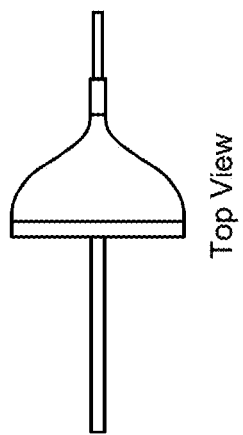
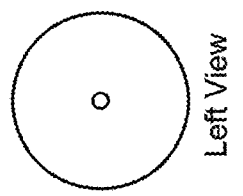
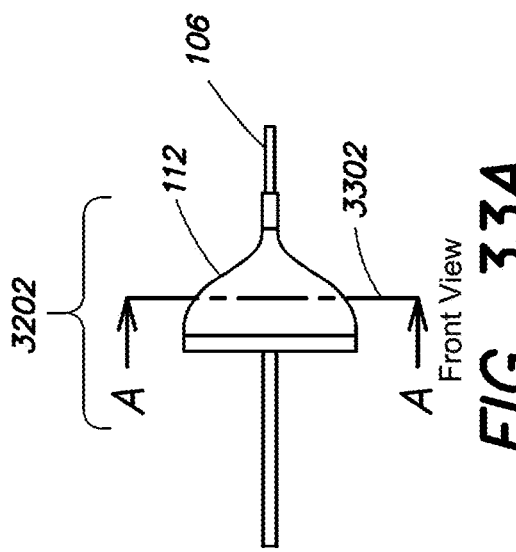
FIG. 33C
FIG. 33B
FIG. 33D
FIG. 33A

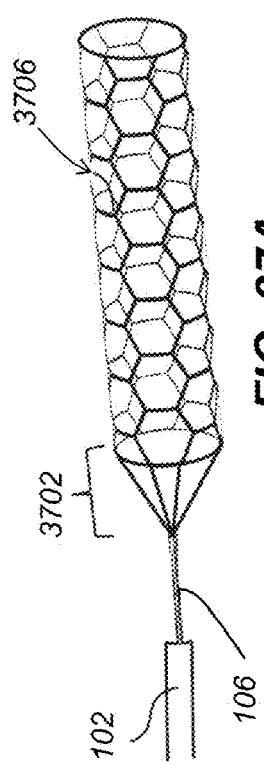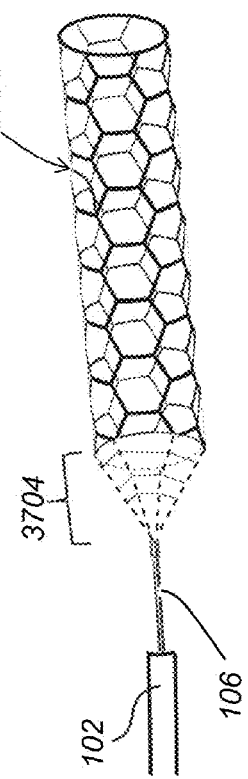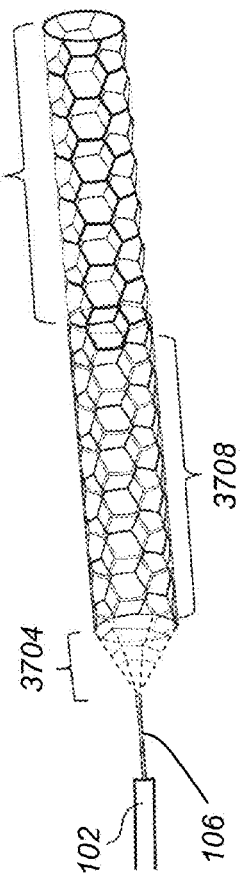

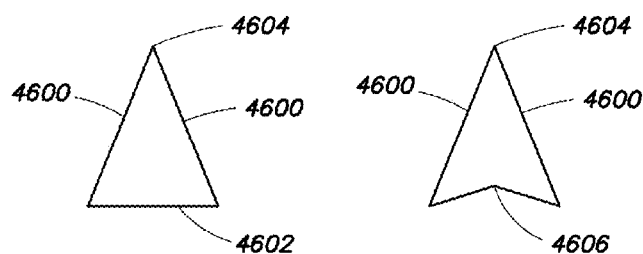
FIG. 46A      FIG. 46B
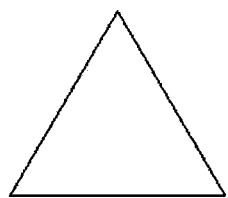 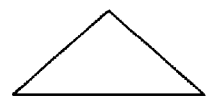 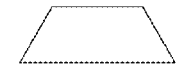
FIG. 46C      FIG. 46D      FIG. 46E
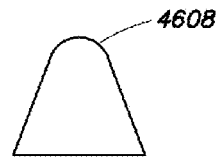  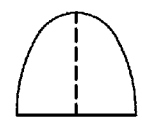
FIG. 46F      FIG. 46G      FIG. 46H
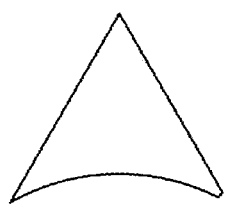  
FIG. 46I      FIG. 46J      FIG. 46K

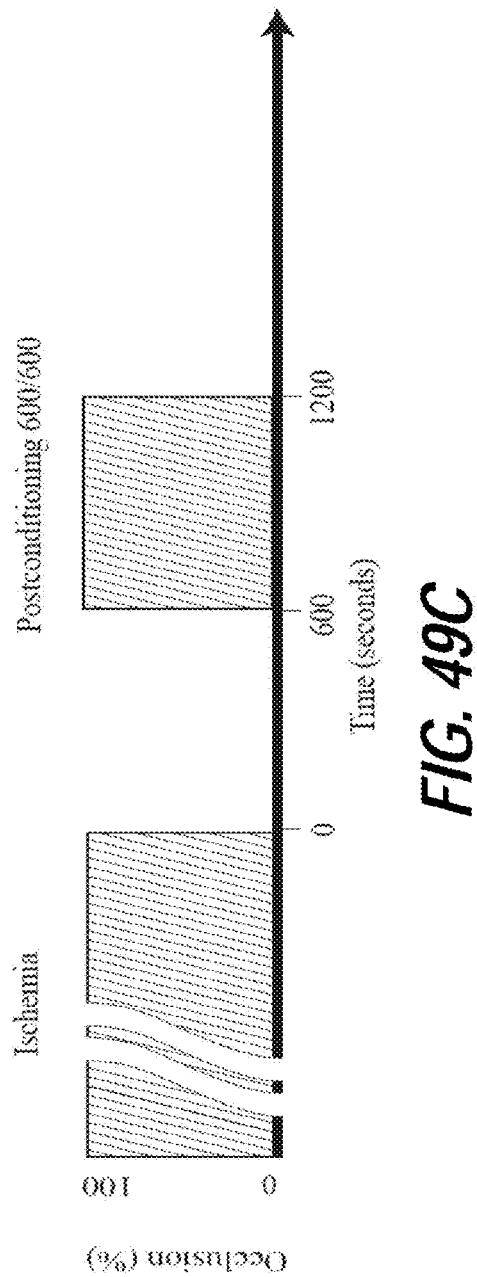
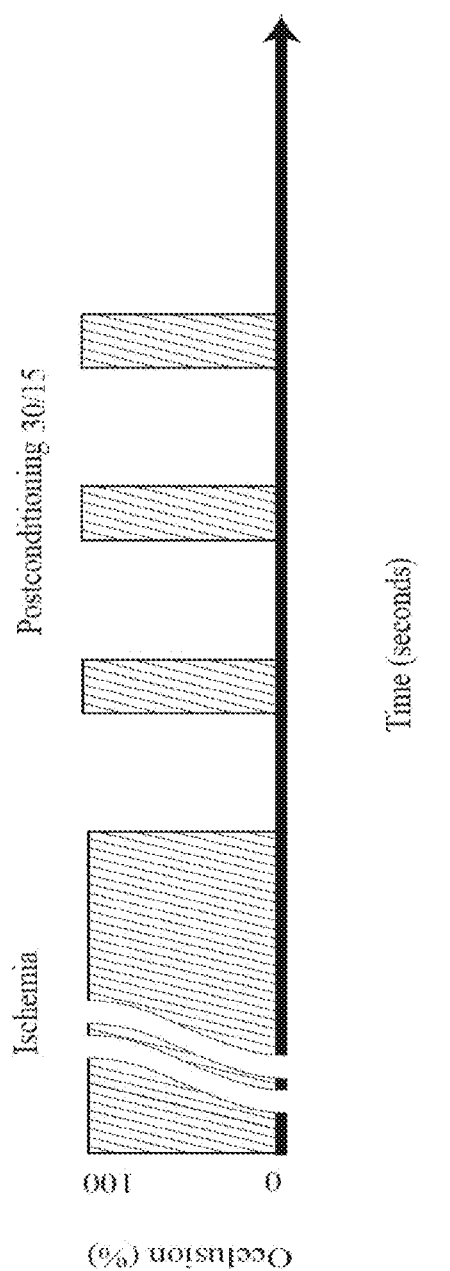
FIG. 49C
FIG. 49D

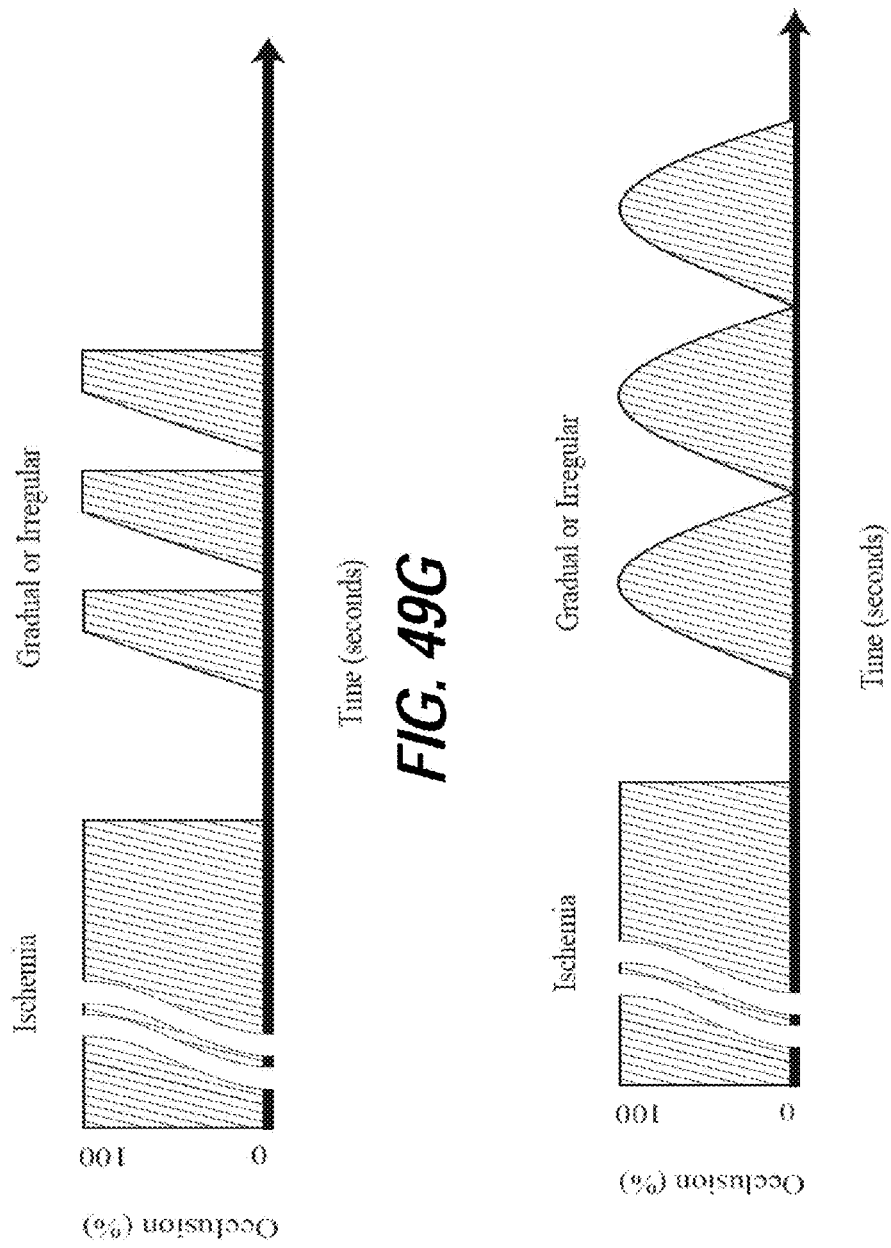

METHODS, DEVICES, AND SYSTEMS FOR POSTCONDITIONING WITH CLOT REMOVAL

RELATED APPLICATIONS

This application claims priority to and incorporates by reference the entire contents of provisional application No. 61/668,408, filed on Jul. 5, 2012.

TECHNICAL FIELD

The present disclosure relates generally to methods, devices, and systems for treating vascular disorders. More specifically, the present disclosure relates to methods, devices, and systems for restoring blood flow by, e.g., removing blood clots, and/or modulating post-reperfusion blood flow.

BACKGROUND OF THE INVENTION

Ischemia, or the restriction of blood supply to tissue, may result in tissue damage in a process known as ischemic cascade, including shortage of metabolic requirements (i.e., oxygen and glucose), build-up of metabolic waste products, inability to maintain cell membranes, mitochondrial damage, and eventual leakage of autolyzing proteolytic enzymes into the cell and surrounding tissues. Brain ischemia may be chronic, e.g., leading to vascular dementia, or acute, e.g., causing a stroke. A stroke is the rapid decline of brain function due to a disturbance in the supply of blood to the brain caused by a clot or hemorrhage in a blood vessel. A clot may consist of at least one of a thrombus, embolus, or thromboembolus. A stroke in which a vessel is restricted or occluded by a clot is an ischemic stroke.

Ischemic stroke is the fourth leading cause of death in the United States, affecting over 795,000 patients per year and costing tens of billions of healthcare dollars. See, e.g., Véronique L. Roger et al., "Heart Disease and Stroke Statistics—2012 Update: A Report from the American Heart Association," 125 *Circulation* e2-e220 (2012). Furthermore, patients who survive an ischemic stroke often require rehabilitation and management of symptoms including loss of brain function, motor skills, and memory. The extent of infarction (i.e., destruction of brain tissue) correlates with the extent of these lingering effects of the stroke and the mortality rate.

Of the existing treatment options for ischemic stroke, an older method, but still the primary method used in the United States, is to treat the clot with a clot-dissolving enzyme known as tissue plasminogen activator (hereinafter "tPA"). The use of tPA has two primary drawbacks. First, tPA has limited effectiveness, both in dissolving clots and providing overall benefits for the patients. Many patients do not qualify for tPA treatment because they do not arrive at the hospital within the effective time window of approximately 4.5 hours after the onset of stroke. Even when used within that window, tPA achieves only a limited decrease in the overall mortality rate. Second, tPA may present adverse effects, such as serious internal bleeding. See, e.g., Götz Thomalla et al., "Two Tales: Hemorrhagic Transformation But Not Parenchymal Hemorrhage After Thrombolysis Is Related to Severity and Duration of Ischemia: MRI Study of Acute Stroke Patients Treated with Intravenous Tissue Plasminogen Activator Within 6 Hours," 38 (2) *Stroke* 313-18 (2007).

A newer method of treating ischemic stroke is mechanical thrombectomy, in which a device physically engages with a clot and is used to drag the clot out of the body. Usually, an operator, e.g., a surgeon, first establishes a path for the thrombectomy device to reach a clot in the cerebral vasculature by inserting an initial guidewire (or guiding catheter) into an artery in a lower region of the body, such as the femoral artery. Then, the operator steers the guidewire through the arteries leading up to the brain and just past (i.e., distal to) the position of the clot. Favoring whichever path poses least resistance, the guidewire passes either between the clot and the blood vessel wall or through the clot. The operator inserts a microcatheter over the initial guidewire to follow its path until reaching a position distal to the clot. The initial guidewire may be removed and replaced with a new guidewire (hereinafter "pushwire" to differentiate from an initial guidewire). This pushwire has a thrombectomy device attached to its distal end to engage with the clot.

Currently, the most successful class of thrombectomy devices is based on neurovascular stent technology. Like stents, which are self-expandable and generally cylindrical, these devices tend to expand to the shape of the blood vessel walls. Thombectomy devices may comprise thin metal struts arranged to create a cell pattern. During device expansion, a clot may become enmeshed in the cells and compressed against a blood vessel wall. At this point, blood flow may be partially or fully restored in the vessel, thus relieving ischemia.

Unfortunately, abrupt restoration of blood supply to ischemic tissues may cause reperfusion injury, which is additional damage to blood vessels, potentially greater damage than even the ischemia. For example, reperfusion results in a sudden increase in oxygen in the tissues, causing a greater production of free radicals and reactive oxygen species that damage cells. The restored blood flow also brings more calcium ions to the tissues causing calcium overloading that may result in potentially fatal cardiac arrhythmias and accelerated cellular self-destruction. Furthermore, reperfusion may exaggerate the inflammation response of damaged tissue, triggering white blood cells to destroy damaged cells that may otherwise still be viable.

Reperfusion injury is highly significant and can visibly increase the infarct size (i.e., destroyed tissue) by as much as 30%. See, e.g., Andrew Tsang et al., "Myocardial Postconditioning: Reperfusion Injury Revisited," 289(1) *Am. J. Physiol. Heart & Circ. Physiol.* H2-7 (2005); Heng Zhao et al., "Interrupting Reperfusion as a Stroke Therapy: Ischemic Postconditioning Reduces Infarct Size After Focal Ischemia in Rats," 26(9) *J. Cereb. Blood Flow & Metab.* 1114-21 (2006); Giuseppe Pignataro et al., "In Vivo and In Vitro Characterization of a Novel Neuroprotective Strategy for Stroke: Ischemic Postconditioning," 28(2) *J. Cereb. Blood Flow & Metab.* 232-41 (2008).

Existing thrombectomy devices and/or systems do not systematically or even adequately control the restoration of blood flow so as to minimize and/or prevent reperfusion injury. Thus far, the prevention of reperfusion injury has been limited to the field of interventional cardiology. During the management of an ischemic event in the heart, a cardiologist will treat the blockade of a vessel with stents and/or balloon angioplasty to restore blood flow. Following reperfusion, a cardiologist uses an inflatable balloon to block and unblock blood flow through the vessel in intervals, thus modulating the resumed blood flow and minimizing reperfusion injury in a process called postconditioning.

Existing postconditioning devices and/or systems are designed for the large arteries of the heart (e.g., catheters with high longitudinal rigidity and large diameters); however, the narrow and tortuous arteries of the cerebral vasculature render these existing devices and/or systems inadequate or at least less desirable in the context of ischemic stroke.

Existing postconditioning devices and/or systems also fail to incorporate simultaneous clot capture. In order to initiate reperfusion and perform postconditioning simultaneously, both a reperfusion member and flow modulation member must be disposed concurrently in the same region. Particularly in the brain, where space constraints make it difficult to fit both an engaged reperfusion member and an active flow modulation member, no existing postconditioning devices and/or systems are designed to simultaneously deploy a clot capture member for reperfusion and perform postconditioning for the ischemic tissue.

Thus, there remains a need for postconditioning devices, systems and methods designed to prevent, minimize, and/or treat ischemic stroke and/or reperfusion injury by restoring and modulating blood flow in the cerebral vasculature.

Meanwhile, in addition to overlooking reperfusion injury, existing thrombectomy devices and/or systems are not designed to consistently bind with, capture, and/or retrieve clots. In fact, only about 30% of clots are successfully retrieved on a first pass (i.e., a deployment of the thrombectomy device). After five passes, 10% of clots still remain lodged. Furthermore, in 10% of cases, reperfusion is not even achieved while a thrombectomy device and/or system is engaged with the clot. Thus, there also remains a need for thrombectomy devices and/or systems that not only increase binding with clots but also increase reperfusion by creating a greater gap within the clot or between the clot and the blood vessel wall.

SUMMARY OF THE INVENTION

The devices, systems, and methods of the present invention are predicated on the recognition of the anatomic and physiologic principles, particularly in the cerebral vasculature, underlying reperfusion injury and ischemic stroke. For instance, the prior thrombectomy and/or postconditioning art fails to recognize the importance of and provide methods and systems for adequately controlling the restoration of blood flow so as to minimize and/or prevent reperfusion injury. Likewise, the prior art fails to appreciate the arterial space constraints in the brain that limit the positioning of devices and/or systems. These embodiments of the present invention are primarily directed, therefore, to initiating reperfusion and performing postconditioning simultaneously in a blood vessel with improved devices, systems, and methods. These embodiments are designed to prevent, minimize, and/or treat ischemia and/or reperfusion injury by restoring and modulating blood flow in the cerebral vasculature, as well as vasculature in the lungs, heart, pelvis, legs, and any other part of the human body.

In on embodiment, an aspect of the invention is a method comprising the steps of introducing a device into a cerebral blood vessel that is at least partially blocked by a clot and applying pressure to an internal wall of the cerebral blood vessel to enhance blood flow in the vessel. Postconditioning is then applied to reduce reperfusion injury. Then in one embodiment the method involves removing at least part of the clot from the vessel and then removing the device from the cerebral blood vessel. Each of the steps in this embodiment, the application of pressure, the removal of the clot, and the postconditioning occurs after the device is introduced and before the device is removed from the vessel. In this method, the step of postconditioning may comprise at least partially occluding the vessel. Another aspect of this method includes performing the steps of applying, removing, and postconditioning comprise a single medical procedure. In another aspect of the method the step of postconditioning may include selectively permitting flow through the vessel and reducing flow through the vessel in prescribed sequence.

Another aspect of the invention is an apparatus that includes a catheter, a balloon disposed on the catheter at a distal end of the catheter. The catheter according to the embodiment includes an orifice for inflating the balloon. A stent is provided in the vicinity of a distal end of a wire that extends through a lumen to an end of the catheter. In another aspect of this embodiment, a sealing interface is disposed between the wire and the lumen, nearer to the distal end of the catheter than is the orifice for inflating the balloon, that is adapted to seal the lumen so that the balloon may be inflated. The sealing interface in this embodiment may include an outwardly facing surface on the wire and an inwardly facing surface on the lumen. Additionally, the inwardly facing sealing surface of the lumen has a smaller diameter than the other portions of the lumen of the catheter. In another aspect of this embodiment, the outwardly facing surface of the wire has a larger diameter than other portions of the wire.

A further embodiment of the invention includes a device capable of transporting fluid and a pushwire bearing a flow restoration member. In this embodiment, the device includes a catheter which includes a lumen that has an inner surface, a pushwire that includes a sealing ring disposed toward the distal end of the pushwire. The sealing ring is sized to sealingly engage the inner surface of the catheter so that when engaged the sealing ring substantially blocks flow of the fluid through the catheter. In another embodiment, an assembly configured to treat ischemia in a patient includes a catheter with a proximal region, a distal region, and a single lumen and a flow modulation member coupled to the proximal region of the catheter and including an inflatable balloon able to reversibly decrease and increase the flow of fluid through the blood vessel at least twice, and so modulate blood flow through the blood vessel. The inflatable balloon according to another embodiment has a balloon inflation aperture continuous with the single lumen and able to receive inflating fluid from the single lumen, a pushwire with a proximal end and a distal end, wherein the pushwire is at least partially within the single lumen, a member for increasing the flow of blood through the clot, coupled to the distal end of the pushwire; and one or more sealing members adapted to decrease the flow rate of inflating fluid leaving the single lumen.

In some embodiments the sealing member is made of an electro-active compound, such that applying and/or altering an electric current applied to the pushwire causes the electro-active sealing member to expand so as to provide more resistance to the flow of fluid through the catheter, wherein the flow modulation member is capable of expanding to produce a desired seal. In this embodiment, as in others, the assembly is adapted to operate with a pressure of the fluid less than 5 atm. Also in this embodiment and others, the member for increasing the flow of blood through a blood vessel beyond a clot comprises a self-expanding scaffold, adapted to engage a clot in a blood vessel.

The catheter in the above embodiment may comprise a first section in the proximal region and a second section in the distal region, the area in the second section of the lumen, in the plane normal to the central axis of the catheter, being smaller than the area in the first section of the lumen, in the plane normal to the central axis of the catheter. The sealing member of the one or more sealing members may comprise a protrusion with an outwardly facing surface attached to the pushwire at a location on the pushwire proximal to the flow restoration member. The protrusion slows the flow of fluid through the lumen when the protrusion engages an inwardly facing surface at the distal region of the catheter. The one or more sealing members of this embodiment may comprise a sealing tip at the distal end of the catheter. A luminal edge of the sealing tip is designed to come in close proximity with a sealing surface of the pushwire and slows the flow of fluid through the lumen when the sealing surface pushwire is placed through the sealing tip. In this embodiment, the sealing tip allows the flow restoration member to pass the sealing tip when the catheter is translated relative to the pushwire.

Another aspect of the inventive method disclosed in this application includes a method of using an assembly able to treat ischemia in a patient, the steps of the method include first, identifying a blood clot in a blood vessel; second, inserting a catheter into the blood vessel, the catheter including a proximal region, a distal region, and a single lumen, wherein a pushwire with a proximal end and a distal end is placed at least partially within the single lumen; third, modulating blood flow in the blood vessel by selectively decreasing and increasing the flow of fluid through the blood vessel with a flow modulation member at least twice. The flow modulation member is coupled to the distal region of the catheter and includes an inflatable balloon having a balloon inflation aperture with the single lumen and adapted to receive inflating fluid from the single lumen, wherein one or more sealing members are provided along the lumen to reduce the volumetric flow rate of inflating fluid leaving the single lumen; and fourth, increasing the flow rate in the blood vessel by translating the catheter relative to the pushwire to deploy a flow restoration member, wherein the flow restoration member is coupled to the pushwire near the distal end of the pushwire and comprises a self-expanding scaffoldable to engage the clot.

An aspect of this method includes the feature that the catheter used in the method comprises a first section in the proximal region and a second section in the distal region, the area in the second section of the lumen, in the plane normal to the central axis of the catheter, being smaller than the area in the first section of the lumen, in the plane normal to the central axis of the catheter. Additionally, another aspect of the invention includes the feature that one or more sealing members used in the method comprise a sealing ring coupled to the pushwire at a location in the single lumen proximal to the flow restoration member, wherein the sealing ring is able to engage the distal region of the catheter. Additionally, the one or more sealing members comprise a sealing tip coupled to the distal end of the catheter, and the sealing tip is adapted to selectively sealingly engage when the catheter is translated relative to the pushwire. Also, according to this embodiment, the sealing tip is able to allow the flow restoration member to pass the sealing tip when the catheter is translated relative to the pushwire.

Another embodiment of the invention includes an assembly able to treat ischemia in a patient with an intermediate catheter with a proximal region, a distal region, and a single intermediate lumen. A flow modulation member is coupled to the proximal region of the intermediate catheter and comprises an inflatable balloon to reversibly decrease and increase the flow of fluid through a blood vessel for modulating blood flow through the blood vessel. The inflatable balloon has a balloon lumen continuous with the single intermediate lumen and receives inflating fluid from the lumen of the intermediate catheter. Also included in this assembly is a microcatheter with a single microcatheter lumen and the microcatheter is at least partially within the lumen of the intermediate catheter. A pushwire having a proximal end and a distal end is adapted to be at least partially within the lumen of the microcatheter. Also included in the assembly of this embodiment is a flow restoration member coupled to the distal end of the pushwire and comprising a self-expanding scaffoldable to engage a clot in a blood vessel and one or more sealing members able to reduce the volumetric flow rate of inflating fluid leaving the single intermediate lumen.

In some embodiments of this invention, the self-expanding scaffold is a stent. Further, in some embodiments, the intermediate catheter includes a first section in the proximal region and a second section in the distal region, the area in the second section of the lumen, in the plane normal to the central axis of the catheter, being smaller than the area in the first section of the lumen, in the plane normal to the central axis of the intermediate catheter. One or more sealing members may be included that have a protrusion which reduces the space between the pushwire and the protrusion through which fluid can flow around the location of the protrusion coupled to the microcatheter, so that the protrusion may facilitate the inflation of the balloon when the protrusion is within or near the distal region of the intermediate catheter. In some embodiments the protrusion is annular. Moreover, the one or more sealing members may include a sealing tip coupled to the distal end of the intermediate catheter, wherein a luminal edge of the sealing tip comes in close proximity with the pushwire and slows the flow of fluid through the lumen when the pushwire is placed through the sealing tip.

Another aspect of the method of this invention may include a method of using an assembly able to treat ischemia in a patient. The steps of this method may include, identifying a target blood clot in a blood vessel; inserting into the blood vessel an intermediate catheter with a proximal region, a distal region, and a single intermediate lumen, wherein a microcatheter with a single microcatheter lumen is at least partially within the single intermediate lumen, wherein a pushwire with a proximal end and a distal end is at least partially within the lumen of the microcatheter; modulating blood flow in the blood vessel by reversibly decreasing and increasing the flow of fluid through the blood vessel with a flow modulation member at least twice, wherein the flow modulation member is coupled to the distal region of the intermediate catheter and comprises an inflatable balloon having a balloon lumen continuous with the single intermediate lumen and able to receive inflating fluid from the single intermediate lumen; reducing the rate of inflating fluid leaving the single intermediate lumen by translating the intermediate catheter relative to the microcatheter so that the protrusion slows the flow of fluid through the lumen when the protrusion engages the distal region of the intermediate catheter; and increasing the flow rate in the blood vessel by translating the catheter relative to the pushwire to deploy a flow restoration member.

In another aspect of the invention the flow restoration member used in the method may be coupled to the pushwire near the distal end of the pushwire and includes a self-expanding scaffold capable of engaging the clot. In still another aspect of the invention, the catheter used in the method may include a first section in the proximal region and a second section in the distal region, the area in the second section of the lumen, in the plane normal to the central axis of the catheter, being smaller than the area in the first section of the lumen, in the plane normal to the central axis of the catheter. The method may employ one or more sealing members used in the method comprise a protrusion coupled to the pushwire at a location in the single lumen proximal to the flow restoration member. The protrusion slows the flow of fluid through the lumen when the protrusion engages the distal region of the catheter. The one or more sealing members used in the method may include a sealing tip coupled to the distal end of the catheter, wherein the sealing tip is able to engage the pushwire when the catheter is translated relative to the pushwire. Additionally, the luminal edge of the sealing tip comes in close proximity with the pushwire and slows the flow of fluid through the lumen when the pushwire is placed through the sealing tip.

In still another embodiment of the invention an assembly able to treat ischemia in a patient is described. In this embodiment, the invention includes a catheter with a proximal end, a distal end, and at least two catheter lumina; one or more flow modulation members coupled to the catheter and comprising an inflatable balloon able to reversibly decrease and increase the flow of fluid through the blood vessel with a flow modulation member at least twice, wherein the inflatable balloon has a balloon lumen continuous with a first catheter lumen and able to receive inflating fluid from the first catheter lumen, wherein the distal end of the first catheter lumen is closed; one or more pushwires with a proximal end and a distal end, wherein the pushwire is placed at least partially within a second catheter lumen; and one or more flow restoration members coupled to the pushwire near the distal end of the pushwire. In this embodiment, a flow restoration member may include a self-expanding scaffoldable to engage a clot in a blood vessel.

In another method of the invention, the assembly is able to treat ischemia in a patient. In this embodiment the use of the assembly includes the following steps: identifying a blood clot in a blood vessel; inserting a catheter into the blood vessel the catheter including a proximal end, a distal end, and at least two catheter lumina, wherein a pushwire with a proximal end and a distal end is placed at least partially within a first catheter lumen; modulating blood flow in the blood vessel by reversibly decreasing and increasing the flow of fluid through the blood vessel with a flow modulation member at least twice, wherein the flow modulation member is coupled to the proximal region of the catheter and comprises an inflatable balloon having a balloon lumen continuous with a second catheter lumen receiving inflating fluid from the second catheter lumen, wherein one or more sealing members slow the flow rate of the inflating fluid that leaves the second catheter lumen; and increasing the flow rate in the blood vessel by translating the catheter relative to the pushwire to deploy a flow restoration member. In this method, the flow restoration member is coupled to the pushwire near the distal end of the pushwire and comprises a self-expanding scaffoldable to engage the clot, In still a further embodiment of the invention an assembly able to treat ischemia in a patient includes: an intermediate catheter with a proximal end, a distal end, and at least two intermediate catheter lumina; one or more flow modulation members coupled to the intermediate catheter and comprising an inflatable balloon or membrane able to reversibly reduce and increase the flow of fluid through the blood vessel at least twice for modulating blood flow through the blood vessel, wherein the inflatable balloon has a connecting lumen continuous with a first intermediate catheter lumen and receives inflating fluid from the first intermediate catheter lumen, wherein the distal end of the first intermediate catheter lumen is closed; one or more microcatheters with a microcatheter lumen, wherein the microcatheter is at least partially within a second intermediate catheter lumen; one or more pushwires with a proximal end and a distal end, wherein the pushwire is at least partially within the microcatheter lumen; and one or more flow restoration members coupled to near the distal end of the pushwire and comprising a self-expanding scaffold that engages a clot in a blood vessel.

In another embodiment of the method according to the invention an assembly is used to treat ischemia in a patient. The steps of the method include: identifying a blood clot in a blood vessel; inserting into the blood vessel an intermediate catheter with a proximal end, a distal end, and at least two intermediate catheter lumina, wherein a microcatheter with a microcatheter lumen is placed at least partially in a first intermediate catheter lumen, wherein a pushwire with a proximal end and a distal end is placed at least partially in the microcatheter lumen; modulating blood flow in the blood vessel by reversibly decreasing and increasing the flow of fluid through the blood vessel with a flow modulation member at least twice, wherein the flow modulation member is coupled to the proximal region of the intermediate catheter and comprises an inflatable balloon having a balloon lumen continuous with a second intermediate catheter lumen and able to receive inflating fluid from the second intermediate catheter lumen; and increasing the flow of blood in the blood vessel by translating the catheter relative to the pushwire to deploy a flow restoration member, wherein the flow restoration member is coupled to pushwire near the distal end of the pushwire and comprises a self-expanding scaffoldable to engage the clot.

The present invention in one embodiment is an assembly adapted to engage a clot in a blood vessel. The assembly includes a catheter with a proximal end, a distal end, and at least one lumen; a pushwire with a proximal end and a distal end, wherein the pushwire is at least partially within the at least one lumen; and a clot capture member coupled to the pushwire near the distal end of the pushwire and comprising a self-expanding scaffold that is capable of engaging a clot in a blood vessel when the catheter is moved so that the expanding scaffold is not completely within the catheter. The scaffold includes open cells formed by a pattern of struts and the cells have a hexagonal cell shape able to facilitate engagement with the clot.

The present invention in another embodiment is an assembly adapted for engaging a clot in a blood vessel. The assembly includes a catheter with a proximal end, a distal end, and at least one lumen; one or more pushwires with a proximal end and a distal end, wherein the pushwire is at least partially within the at least one lumen; and a clot capture member coupled to the distal end of the pushwire and comprising a self-expanding scaffold to engage a clot in a blood vessel when the catheter is refracted so as to at least partially not surround the expanding scaffold, wherein the scaffold comprises open cells formed by a pattern of struts, wherein at least one of the struts has a cross-sectional shape with an angle less than 180 degrees oriented such that the angle protrudes outward from the scaffold to facilitate engagement with the clot.

According to another method of the present invention a clot in a blood vessel can be engaged. The method includes the steps of: identifying a blood clot in a blood vessel; inserting into the blood vessel a catheter with at least one lumen, wherein a pushwire with a proximal end and a distal end is placed at least partially within the at least one lumen, wherein a clot capture member comprising a self-expanding scaffold is coupled to the distal end of the pushwire; aligning the distal end of the catheter within or distal to the clot; retracting the catheter to unsheathe and allow the scaffold to expand within the blood vessel, wherein the scaffold comprises open cells formed by a pattern of struts, wherein the cells have a hexagonal cell shape able to facilitate engagement with the clot; and extracting any clot material engaged by the scaffold by removing the catheter and the pushwire from the blood vessel.

In still another embodiment of the invention, the specification describes a method for engaging a clot in a blood vessel. The steps include: identifying a blood clot in a blood vessel; inserting into the blood vessel a catheter with at least one lumen, wherein a pushwire with a proximal end and a distal end is placed at least partially within the at least one lumen, wherein a clot capture member comprising a self-expanding scaffold is coupled to the pushwire near the distal end of the pushwire; placing the distal end of the catheter close to the distal end of the clot; retracting the catheter to unsheathe and allow the scaffold to expand within the blood vessel, wherein the scaffold comprises open cells formed by a pattern of struts, wherein at least one of the struts has a cross-sectional shape with an angle less than 180 degrees oriented such that the angle protrudes outward from the scaffold to facilitate engagement with the clot; and extracting any clot material engaged by the scaffold by removing the catheter and the pushwire from the blood vessel.

In another aspect of the invention assembly is disclosed that is able to prevent and/or treat ischemic stroke in a patient. The assembly according to this embodiment includes a flow restoration member comprising a self-expanding scaffold capable of engaging a clot in a cerebral blood vessel; and a flow modulation member to reversibly decreasing and increasing the flow of fluid through the blood vessel with the flow modulation member at least twice, performing one or more postconditioning cycles in the cerebral blood vessel, wherein the members are able to be used simultaneously to prevent and/or treat ischemic stroke.

The invention in another embodiment includes a method of preventing and/or treating ischemic stroke in a patient. In this embodiment the steps of the method include: identifying a blood clot in a cerebral blood vessel; inserting an assembly able to prevent, mitigate and/or treat ischemic stroke into the blood vessel, the assembly comprising: a flow restoration member comprising a self-expanding scaffoldable to engage a clot in a cerebral blood vessel; and a flow modulation member able to modulate blood flow in a cerebral blood vessel, wherein the members are able to be used simultaneously to prevent, mitigate, reduce and/or treat ischemic stroke; deploying the scaffold to restore blood flow in the cerebral blood vessel; and performing one or more postconditioning cycles with the flow modulation member by reversibly decreasing and increasing the flow of fluid through the blood vessel at least twice.

The present invention is according to another embodiment, a device for modulating blood flow, the device includes: a flow modulation member having a plurality of self-expanding struts and a membrane capable of blocking blood flow; a pushwire, wherein the flow modulation member is attached to the pushwire; and a microcatheter with a lumen sized to receive at least a portion of the pushwire, the membrane capable of blocking blood flow attached to the microcatheter, wherein relative movement between the pushwire and the microcatheter in one direction unsheathes the flow modulation member, allowing the flow modulation member to expand, and wherein relative movement between the pushwire and the microcatheter in the opposite direction re-sheathes the flow modulation member, causing the flow modulation member to retract.

Another embodiment of the present invention is a device for modulating blood flow, the device includes: a flow modulation member comprising a microcatheter and an inflatable balloon attached to the microcatheter adapted to selectively reduce blood flow; a fluid conduit associated with the microcatheter for conducting inflation fluid between a proximal side of the microcatheter and the balloon, wherein the conduit is flexible and contiguous with the microcatheter. In this embodiment, the conduit may be a tube that travels outside the microcatheter. The conduit according to this embodiment may be disposed in a helical arrangement outside the microcatheter. The conduit of this embodiment may be a hollow space between an inner wall and an outer wall of the microcatheter, the inner and outer wall of the microcatheter connected at selected locations along its length.

In another aspect of the invention, device for engaging with a blood clot or embolus includes: a clot capture member attached to a push wire and having a plurality of self-expanding struts with an angular cross-sectional profile, wherein a point of the profile faces outward from the clot capture member; and a microcatheter for housing the clot capture member, wherein relative movement between the pushwire and the microcatheter in one direction unsheathes the member, causing the member to expand, and wherein relative movement between the pushwire and the microcatheter in the opposite direction re-sheathes the member, allowing the member to retract. In aspect, the system for achieving and modulating reperfusion may include a flow modulation member capable of blocking blood flow; a pushwire with a self-expanding clot capture member attached toward the distal end, and, a pushwire, adapted to be introduced to the vasculature through the microcatheter and wherein both the clot capture member is attached to the pushwire; and the flow modulation member is also attached to the pushwire; and a microcatheter adapted to receive at least a portion of the pushwire, wherein relative motion between the guidewire and the microcatheter in one direction is capable of unsheathing both the flow modulation member and the clot capture member, causing one or both members to expand, and wherein relative motion between the guidewire and the microcatheter in an opposite direction is capable of re-sheathing one or both of the flow modulation member and the clot capture member, causing one or both members to retract.

A system for achieving and modulating reperfusion of a vessel in the cerebral vasculature following ischemic stroke is another aspect of the invention. In this embodiment, the system includes: a flow modulation member capable of reversibly reducing blood flow; a mechanism for selectively causing blood flow of the vessel to increase; and the flow modulation member adapted to reach the location of the clot via the endovascularture; the system adapted so that the flow modulation member is capable of performing at least two iterations of reducing and then varying flow in the vessel proximate the site of the clot.

A method for modulating blood flow is another aspect of the invention. In this embodiment the method includes: inserting a microcatheter into a blood vessel; inserting a pushwire into the microcatheter, wherein a flow modulation member is attached to the pushwire, wherein the member has a plurality of self-expanding struts and a membrane capable of blocking blood flow; translating the pushwire or the microcatheter relative to one another in one direction to unsheathe the member, allowing the member to expand; translating the pushwire or the microcatheter relative to one another in an opposite direction to re-sheathe the member, causing the member to retract; and repeating the translating steps at least once to modulate blood flow.

An embodiment of the invention can also be described as method for modulating blood flow for the treatment of ischemic stroke. In this embodiment the method includes: inserting a microcatheter and a fluid conduit into a blood vessel, wherein the conduit is flexible and contiguous with the microcatheter, wherein a flow modulation member is attached to the microcatheter, and wherein the member has an inflatable balloon capable of blocking blood flow; conducting inflation fluid to the balloon, causing the balloon to expand; conducting inflation fluid from the balloon, causing the balloon to retract; and repeating the conducting steps at least once to modulate blood flow.

Another embodiment of the invention can be described as a method for removing a blood clot or embolus, the method includes the steps of: inserting a microcatheter into an occluded blood vessel; inserting a pushwire into the microcatheter, wherein a self-expanding clot capture member is attached to the guidewire and has a plurality of self-expanding struts with an angular cross-sectional profile, wherein a point of the profile faces outward from the member toward the clot or embolus; translating the guidewire or the microcatheter relative to one another in one direction to unsheathe the member, causing the member to expand to engage the clot or embolus.

The invention presently disclosed in one embodiment is a method for achieving and modulating reperfusion, the method according to this embodiment includes the steps of: inserting a microcatheter into an occluded blood vessel; inserting a pushwire into the microcatheter, wherein both a flow modulation member capable of blocking blood flow and a self-expanding clot capture member are attached to the pushwire; translating the pushwire or the microcatheter relative to one another in one direction to unsheathe one or both of the flow modulation member and the clot capture member, causing one or both members to expand; and translating the guidewire or the microcatheter relative to one another in an opposite direction to re-sheathe one or both of the flow modulation member causing the flow modulation member to retract; and repeating the translating steps at least once to treat an occlusion and modulate reperfusion.

The present invention in another embodiment is a method for achieving and modulating reperfusion, the method includes the steps of: inserting a microcatheter into an occluded blood vessel; inserting a pushwire into the microcatheter, wherein a self-expanding clot capture member is attached to the guidewire; and a flow modulation member capable of blocking or reducing blood flow is attached to the microcatheter; translating the pushwire or the microcatheter relative to one another in one direction to unsheathe the clot capture member, causing the clot capture member to expand; and performing an expansion step to cause the flow modulation member to occlude or lessen flow; and repeating the expansion at least once to modulate reperfusion.

Finally, the present invention in an embodiment is a system for achieving and modulating reperfusion, the system includes: three catheters where in at least one region, a narrow catheter is inside an intermediate catheter, and the intermediate catheter, is inside a largest catheter; wherein a pusher member is at least partially inside the narrow catheter; and the intermediate catheter has a flow modulation member capable of reversibly occluding or blocking flow near its distal end; a clot capture member; a pushwire, wherein the clot capture member is attached to the pushwire; wherein relative translation between the pushwire and the smallest catheter in one direction is capable of unsheathing the clot capture member, causing the capture member to expand.

The details of one or more embodiments of the present invention are set forth in the accompanying drawings and the description below. Other features, objects, and advantages of the present invention will be apparent from the description and drawings, and from the claims.

BRIEF DESCRIPTION OF THE DRAWINGS

The invention and the following detailed description of certain embodiments thereof may be understood with reference to the following figures:

FIGS. 23A-23B illustrate the angle between the central longitudinal axis and a primary strut axis in an umbrella-like flow modulation member during working and resting states in accordance with some embodiments of the present invention;

FIGS. 32A-32G and 33A-33D illustrate an umbrella-like flow modulation member with struts encased in a membrane in accordance with some embodiments of the present invention;

FIGS. 37A-37E illustrate a series of assemblies with a flow modulation member and a clot capture member in accordance with some embodiments of the present invention;

FIGS. 46A-46K illustrate various strut cross-sections for a clot capture member in accordance with some embodiments of the present invention;

FIGS. 49A-49J illustrate various timed occlusion/reperfusion cycles for flow modulation in accordance with some embodiments of the present invention.

DETAILED DESCRIPTION

Embodiments of the present invention include new devices, systems, and methods for preventing, treating, and/or at least minimizing ischemic stroke and/or reperfusion injury by restoring and/or modulating blood flow, particularly in the cerebral vasculature. These devices, systems, and methods make it possible for a clinician to adequately and systematically restore blood flow to ischemic tissue while simultaneously modulating the blood flow to minimize reperfusion injury. Some embodiments of the present invention specifically enable postconditioning in the challenging dimensional constraints of the brain. Some embodiments further enable improved binding with clots and reperfusion by creating a greater gap in the clot or between the clot and the blood vessel wall, particularly for clots that are resistant to the weak engagement of existing thrombectomy devices and/or systems. Contributing features, such as flexibility and radial force, will be discussed further herein.

Reperfusion and/or Flow Modulation Devices and Systems

According to some embodiments of the present invention, a flow modulation system may include an initial guidewire, a microcatheter, an intermediate catheter, and/or a flow modulation member. According to some embodiments of the present invention, a reperfusion system may include an initial guidewire, a microcatheter, an intermediate catheter, a pushwire and/or a clot capture member. In further embodiments of the present invention, a flow modulation system and a reperfusion system may be combined to systematically and effectively control the restoration of blood flow so as to prevent, minimize, and/or treat ischemic stroke and/or reperfusion injury by restoring and modulating blood flow in a blood vessel, such as an cerebral artery.

Figure 1A:
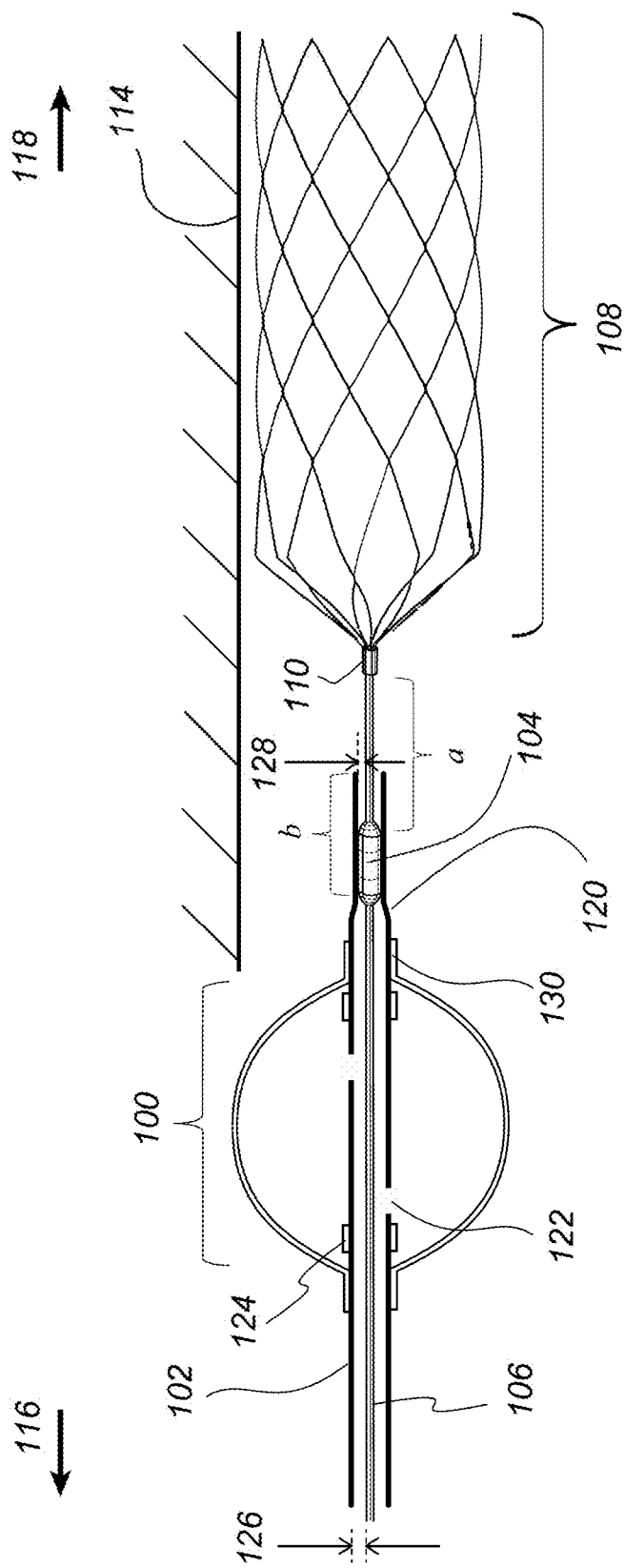
FIGS. 1A-1B illustrate assemblies with a single-lumen balloon microcatheter and a pushwire-mounted sealing ring in accordance with some embodiments of the present invention.
Figure 1B:
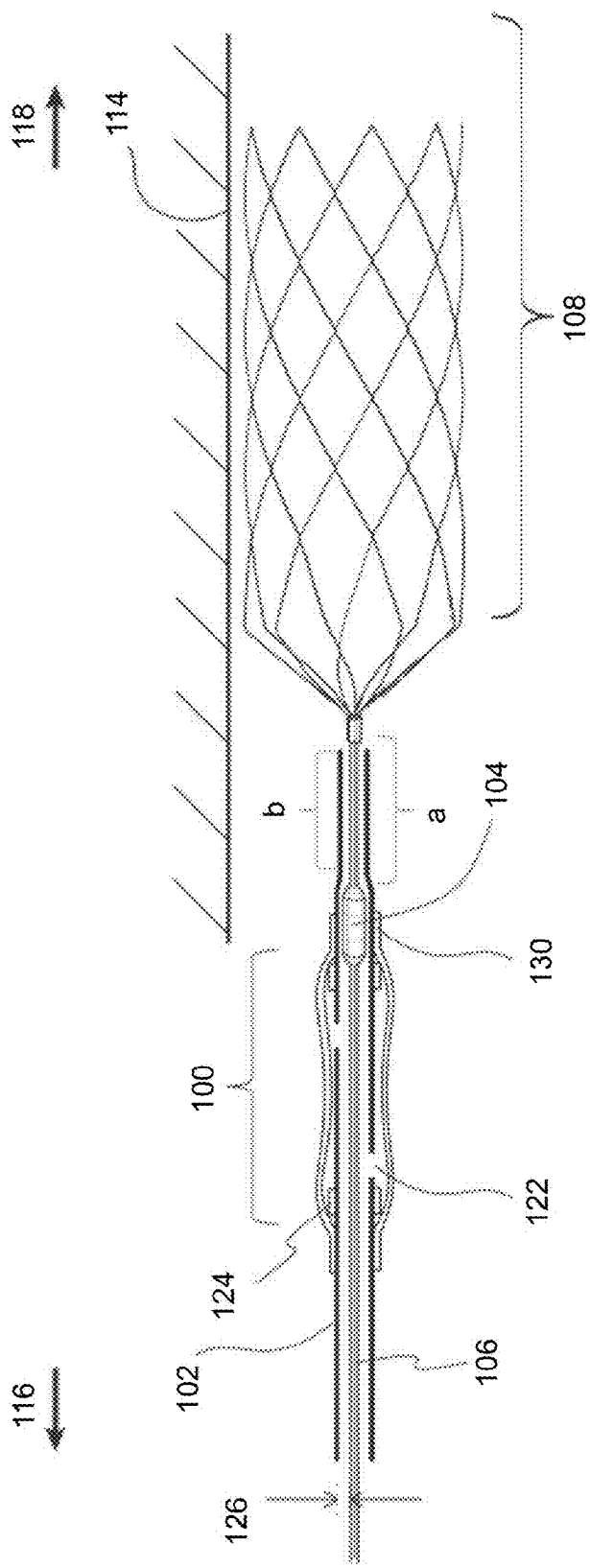

FIGS. 1A-1B, for example, illustrate endoluminal assemblies in accordance with some embodiments of the present invention. The assembly in FIG. 1A, which is disposed in a blood vessel with wall 114. includes a flow modulation member 100, a microcatheter 102, a pushwire 106, and a clot capture member 108 that is attached to the pushwire with an attachment ring 110. These devices are situated between the luminal walls 114 of a blood vessel with blood flowing from the proximal direction 116 to the distal direction 118.

According to some embodiments of the present invention, an initial guidewire or access wire may be included and used to navigate an initial path through the vasculature from a point of insertion into the body (located, e.g., at the groin)

to a location in a blood vessel of a clot and/or ischemic region (e.g., a cerebral artery). A guidewire may be advanced beyond the clot and/or ischemic region to allow room for catheters and devices in accordance with embodiments of the present invention.

According to some embodiments of the present invention, a guidewire may be manufactured from one or more materials including, but not limited to, gold, nitinol, platinum, stainless steel, nickel, titanium, and tungsten. In some embodiments, a guidewire may be plated with radio-opaque materials, such as gold or platinum, to aid visibility during a procedure. In further embodiments, a guidewire may have some form of exterior coating to reduce friction and/or provide other advantages. Exterior coatings may include, but are not limited to, a silicone coating to reduce friction, a hydrophilic coating to lubricate, an anti-thrombogenic/Heparin coating to inhibit clotting, a hydrophobic coating to provide greater tactile response, and a polytetrafluoroethylene (PTFE) coating to reduce friction.

According to some embodiments of the present invention, one or more catheters or flexible tubes may be inserted and used to deliver devices and/or fluids to the clot and/or ischemic region. According to some embodiments, a catheter may have one or more lumina. A catheter may be advanced over the inserted guidewire, which enables the catheter to follow its predefined pathway to the point of treatment. According to some embodiments, one or more catheters may include, but is not limited to, a microcatheter, an intermediate catheter, and a large catheter.

According to some embodiments of the present invention, a microcatheter may be used to deliver devices and/or fluids to the clot and/or ischemic region of the blood vessel. These devices and fluids may include, but are not limited to, flow modulation members, clot capture members, inflating fluids, and drugs (e.g., tPA).

According to some embodiments of the present invention, an intermediate catheter (e.g., size 5 French) may be used to establish a conduit to a position closer to the clot and/or ischemic region of the blood vessel, preserve a path to the clot, and decrease the time needed for multiple passes. An intermediate catheter may be used to deliver devices and/or fluids including, but not limited to, microcatheters, flow modulation members, clot capture members, inflating fluids, and drugs (e.g., tPA). An intermediate catheter may also be used to contain or aspirate clot material once a clot capture member is pulled into the catheter.

According to some embodiments of the present invention, an large catheter (e.g., size 6 French, such as ENVOY® Guiding Catheter available from DePuy Orthopedics, Inc. (Warsaw, Ind.)) may be used to establish a conduit for the guidewire and catheters through larger blood vessels, preserve that path, and decrease the time needed for multiple passes. A larger catheter may also be used to contain or aspirate clot material once a clot capture member is pulled into the catheter.

According to some embodiments of the present invention, a catheter may be manufactured from materials including, but not limited to, silicone rubber, nitinol, nylon, polyurethane, and polyethylene terephthalate (PETE) latex, and thermoplastic elastomers. In further embodiments, catheters may have some form of exterior coating to reduce friction and/or provide other advantages. Exterior coatings may include, but are not limited to, a silicone coating to reduce friction, a hydrophilic coating to lubricate, an anti-thrombogenic/Heparin coating to inhibit clotting, a hydrophobic coating to provide greater tactile response, and a PTFE coating to reduce friction.

Figure 2:
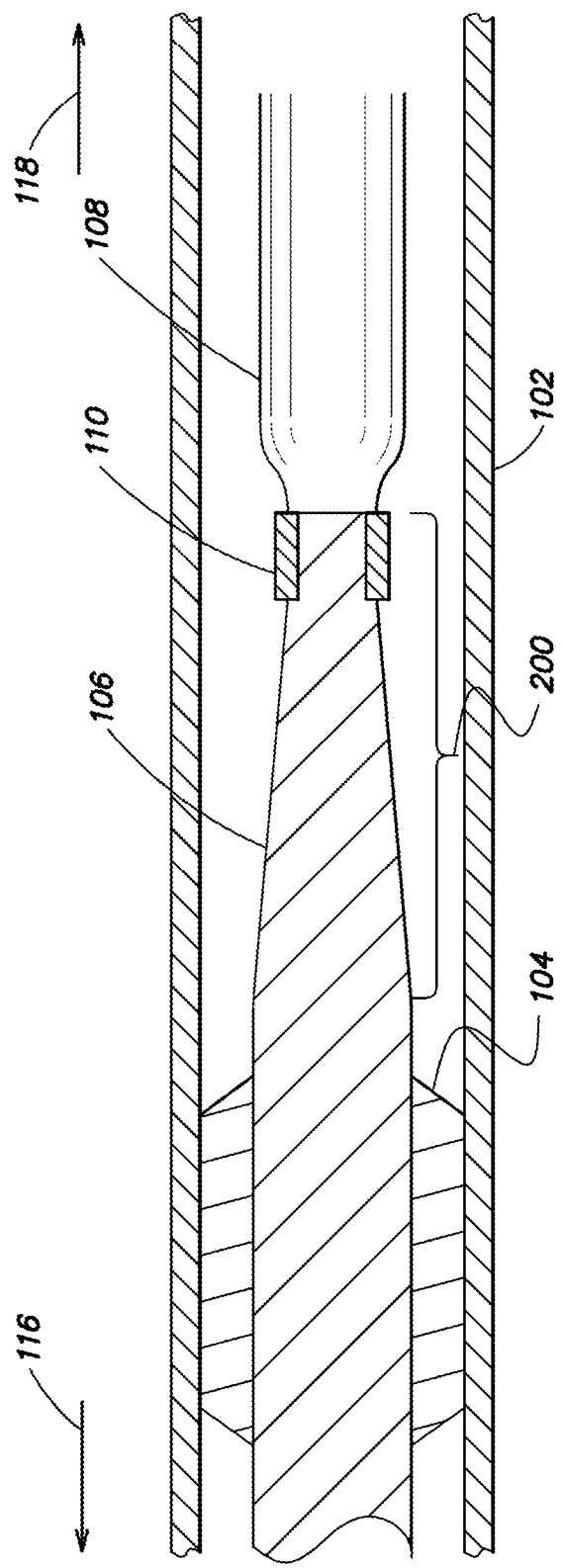
FIG. 2 illustrates a guidewire with distal tapering in accordance with some embodiments of the present invention.
Figure 3A:
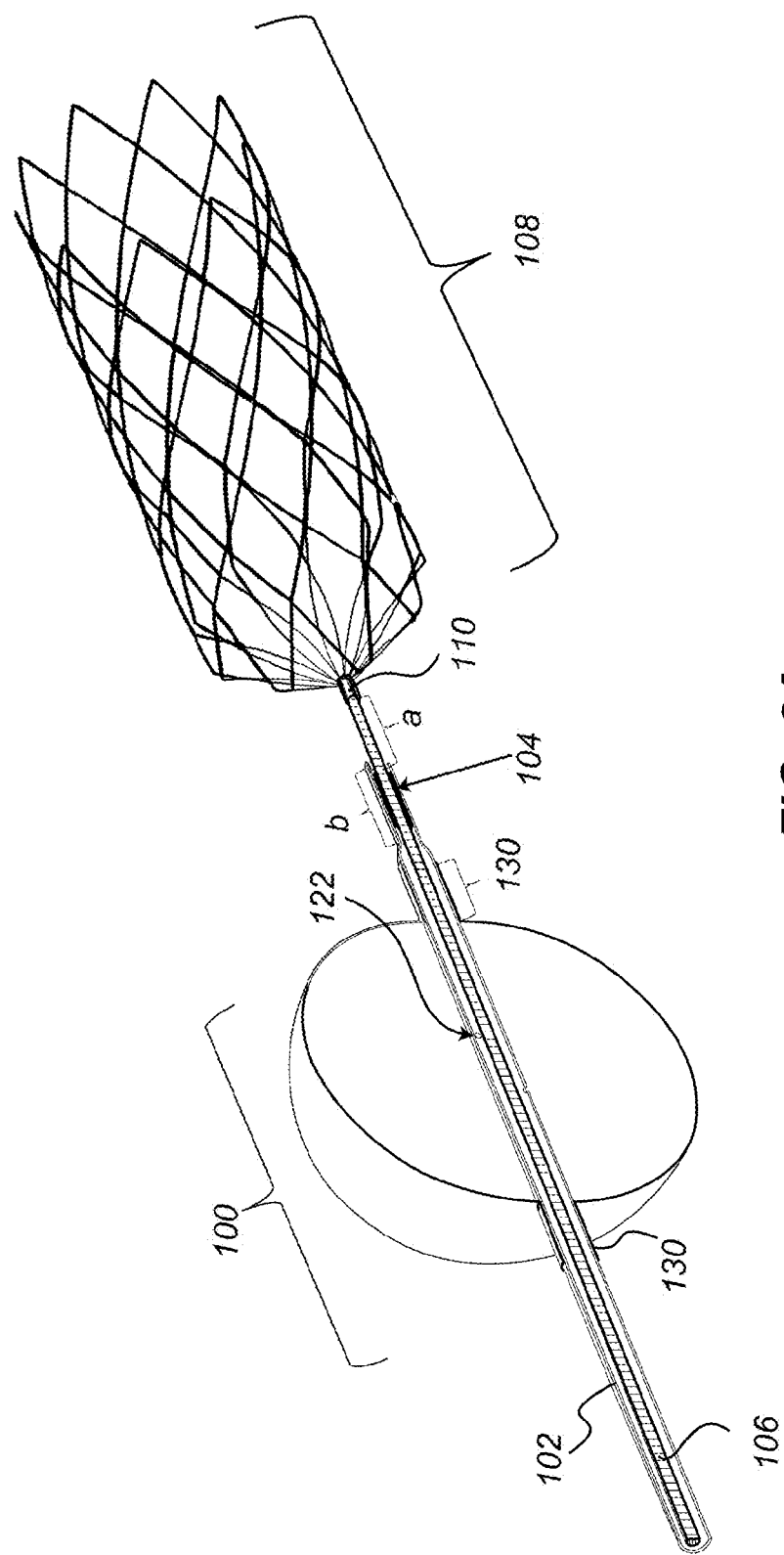
FIGS. 3A-3B illustrate assemblies with a single-lumen balloon microcatheter and a pushwire-mounted sealing ring in accordance with some embodiments of the present invention.
Figure 3B:
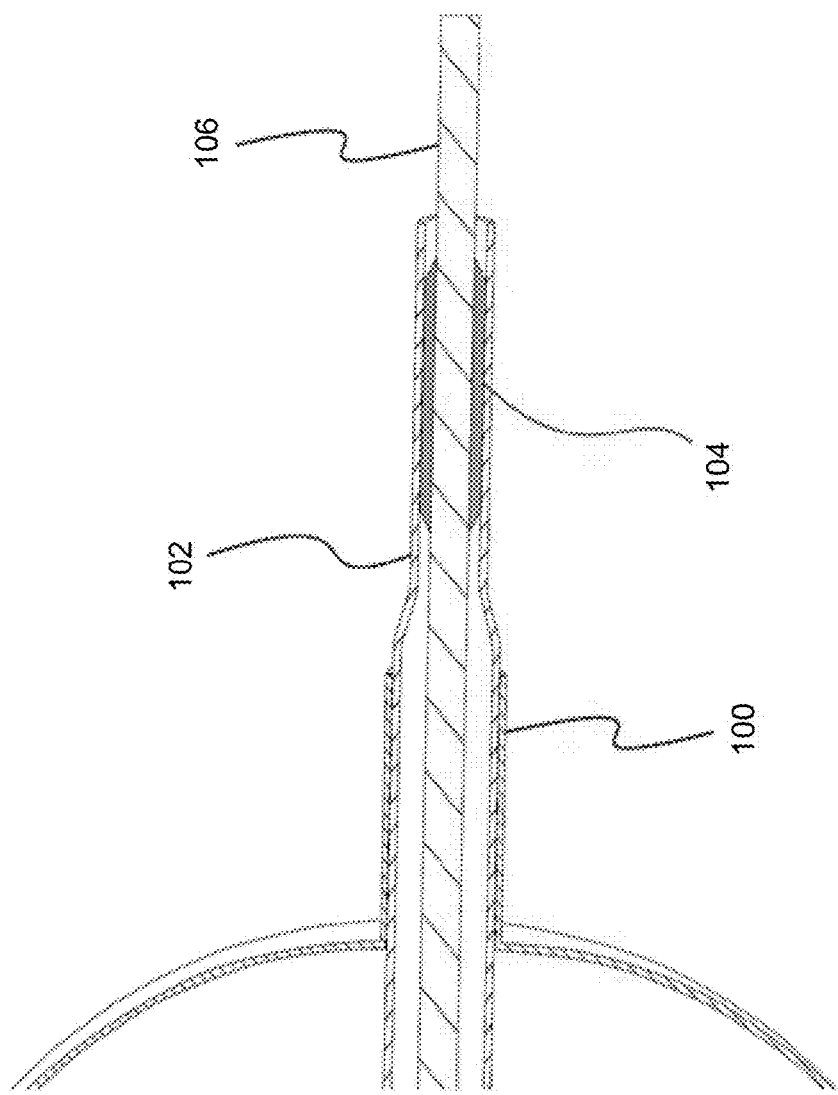
Figure 4A:
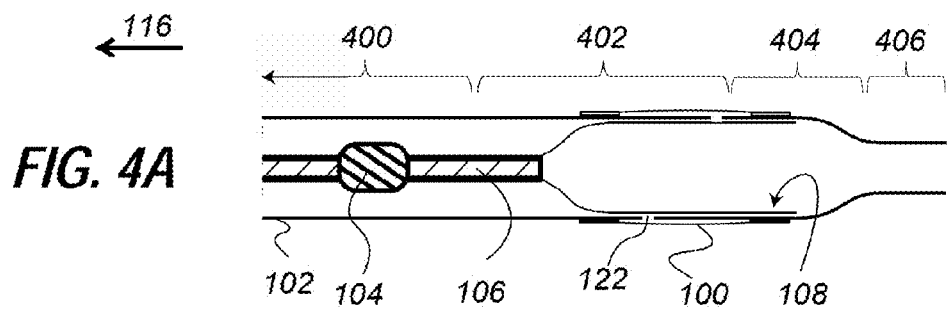
FIGS. 4A-4D and 5 illustrate steps for using assemblies with a single-lumen balloon microcatheter and a pushwire-mounted sealing ring in accordance with some embodiments of the present invention.
Figure 4B:
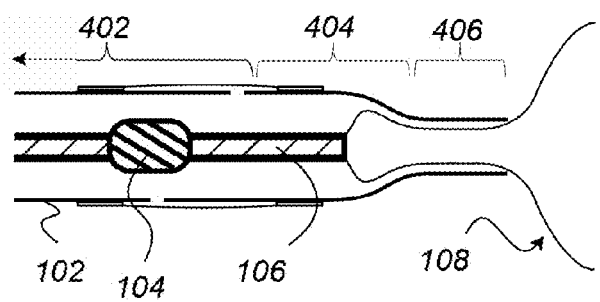
Figure 4C:
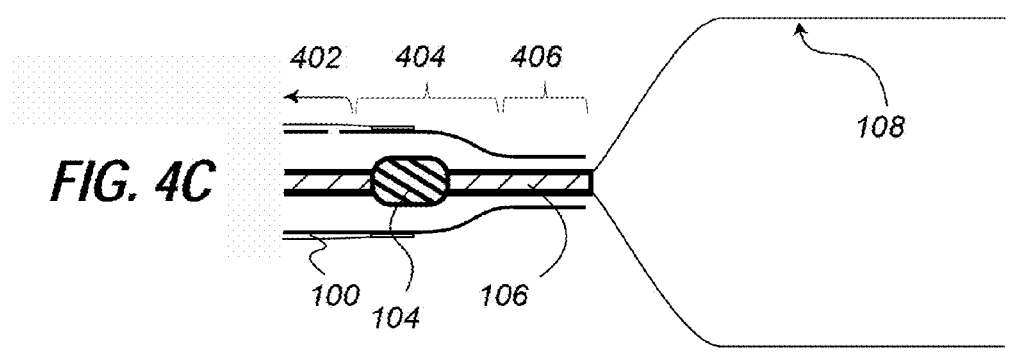
Figure 4D:
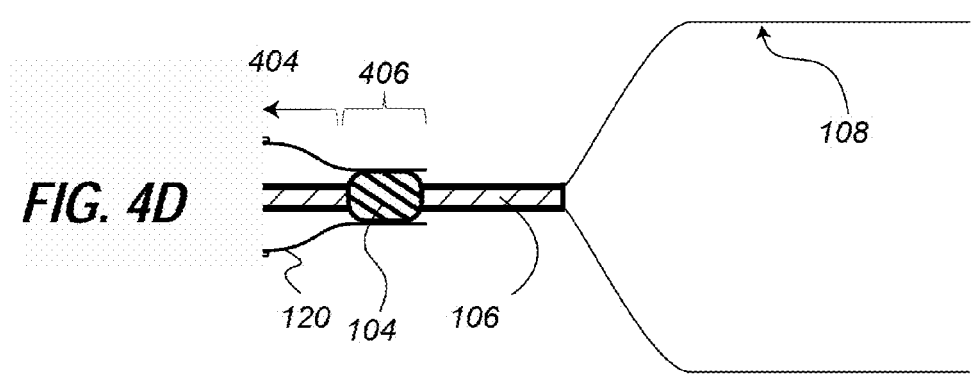

Following removal of an initial guidewire, a similar wire may be inserted into a lumen of a microcatheter that has been placed over the initial guidewire in accordance with embodiments of the present invention. This "pushwire" carries one or more distal devices, such as a flow modulation member and a clot capture member. A pushwire may be inserted and guided along a predefined pathway to the location of a clot and/or ischemic region in the body to deliver distal devices, generally by translation relative to a microcatheter. According to some embodiments, when a microcatheter is retracted, a distal device on the pushwire may be unsheathed by translation of the microcatheter in the proximal direction. In further embodiments, a distal device on the pushwire may be resheathed by translation of the microcatheter in the opposite distal direction. A pushwire may taper toward the distal end to provide more latitudinal flexibility and room for distal devices. FIG. 2 illustrates a guidewire 106 with tapering in region 200 in accordance with some embodiments of the present invention.

According to some embodiments of the present invention, a pushwire may be manufactured from one or more materials including, but not limited to, gold, nitinol, platinum, stainless steel, nickel, titanium, and tungsten. In some embodiments, a pushwire may be plated with radio-opaque materials, such as gold or platinum, to aid visibility during a procedure. In further embodiments, a pushwire may have some form of exterior coating to reduce friction and/or provide other advantages. Exterior coatings may include, but are not limited to, a silicone coating to reduce friction, a hydrophilic coating to lubricate, an anti-thrombogenic/Heparin coating to inhibit clotting, a hydrophobic coating to provide greater tactile response, and a PTFE coating to reduce friction.

According to some embodiments, a delivery handle and winged steering apparatus, which remain outside the body, may be used to facilitate the insertion and/or control the movements of guidewires, catheters, pushwires, and distal devices, by allowing an operator to impart greater torque.

According to some embodiments of the present invention, a reperfusion member is any mechanical device or chemical entity adapted to achieve reperfusion. A clot capture member is a type of reperfusion device that engages with a clot in a blood vessel, with the goal of removing the clot (preferably from the body entirely) in accordance with some embodiments. In some embodiments, a clot capture member may be a distal device, that is, the clot capture member may be coupled to the distal end of a pushwire and delivered to the location of a clot via the lumen of a catheter. A pass is an attempt to macerate, dislodge, and/or remove clot material. According to some embodiments, a pass may consist of navigating a guidewire past the location of a clot, translating a catheter over the guidewire and past the clot, exchanging the guidewire for a pushwire coupled with a reperfusion member, such as a clot capture member. If a first pass is not successful, a new pass may require repeating one or more of these steps. Clot capture members generally and improved variations thereupon are described in greater detail below in accordance with some embodiments of the present invention.

According to some embodiments of the present invention, a flow modulation member is any device adapted to modulate blood flow by, for example, reversibly occluding a blood vessel. A flow modulation member may partially or completely occlude a blood vessel, for example, in intervals, with the goal of postconditioning an ischemic region, particularly to prevent and/or minimize reperfusion injury, in accordance with some embodiments. In some embodiments, a flow modulation member may be a distal device, that is, the flow modulation member may be coupled to the distal end of a pushwire and delivered to the location of a clot via the lumen of a catheter. In other embodiments, a flow modulation member may be an inflatable member that is coupled to the distal end of a pushwire, a microcatheter, or an intermediate catheter.

For embodiments in which a flow modulation member inflates and deflates to reversibly occlude a blood vessel, a lumen of a catheter may be used as a conduit for inflating fluid. In some of these embodiments, a port may be added to the proximal end of the catheter for pumping the inflating fluid. Other ports may be provided for inserting other fluids and devices, such as a probe for monitoring pressure in the inflatable member. Flow modulation members generally and improved variations thereupon are described in greater detail below in accordance with some embodiments of the present invention.

According to some embodiments, a flow modulation member is positioned proximal to a clot and/or clot capture member in order to reversibly control occlusion at the same time that a clot capture member is engaged with a clot and reperfusion of the blood vessel first begins. A flow modulation member should be positioned close to the clot and/or clot capture member to minimize the probability of interference with from a collateral artery feeding the reperfused blood vessel between the flow modulation member and the clot but not so close as to disturb the clot or clot capture member. In preferred embodiments, the proximity of a flow modulation member is selected to maximize the extent to which a reperfused blood vessel receives the benefits of postconditioning. For example, in the embodiments shown in FIGS. 1A-1B, the flow modulation member 100 is designed with a balloon of diameter (at its target level of inflation) of 2.4 mm for blood vessels with a diameter of 2 mm, and is positioned with the location the center of the balloon is 12 mm proximal to the distal end of the microcatheter. Generally, the distance between the center of the balloon and the distal end of the microcatheter may range from 5 mm to 40 mm.

Single-Lumen Balloon Embodiments of a Flow Modulation Member

According to some embodiments of the present invention, the flow modulation member consists of a balloon, which may have some features similar to balloons used for cardiac postconditioning and/or balloon catheters. However, one critical difference between the present embodiments and balloons used in other parts of the body is that this flow modulation balloon and its inflating-fluid conduit must be able to navigate the narrow, winding blood vessels of the brain. Existing saline tube configurations, particularly those that may be used in connection with a clot treating system, are not capable of effectively reaching the parts of blood vessels where clots tend to occur. Thus, embodiments are designed to overcome the obstacles of size and flexibility while maintaining the ability to inflate and deflate rapidly, as controlled by an operator.

Single-Lumen Balloon Microcatheters with Pushwire-Bearing Sealing Rings

FIGS. 1A-1B and 3A-3B illustrate unique assemblies, in accordance with some embodiments of the present invention, including a sealing ring 104 mounted on a pushwire 106 and a balloon 100 mounted on a microcatheter 102, which provides enhanced navigability and allows for the delivery of the capture member 108 at the location of the clot. Clots tend to lodge in the Middle Cerebral Artery, where the vasculature is particularly tortuous. Current single-lumen balloon microcatheters cannot be used to deliver stent-based clot capture members because their mode of action is incompatible with stent delivery. Current single-lumen balloon microcatheters have a seal at the distal end that exactly fits the diameter of the appropriate guidewire. Therefore, this distal seal on current single lumen balloon microcatheters would interfere with stent-based clot capture members attempting to exit the microcatheter's distal end.

The sealing ring 104 assembly, positioned at the distal end of the pushwire 106, but before the clot capture member 108, allows for a clot capture member to be compatible with a balloon microcatheter. The ring allows for a sealing region (b) with increased diameter, so that the reperfusion member has ample space to pass through the sealing region without risking jamming the assembly. The ring completes the seal upon entering the sealing region. Therefore the ring enables the narrow sealing region to be wider than the diameter of the pushwire.

The preferred length of the sealing ring is approximately 2 mm. However, different dimensions for the sealing ring may be used (e.g., from approximately 1 mm to 5 mm in length). The diameter of the sealing ring is preferred to be the same as the inner diameter of the narrower part (b) of the microcatheter (at the distal end). It is anticipated that matching diameters will provide adequate sealing while minimizing the risk of assembly jamming. However, different dimensions for the sealing ring may be used (e.g. from 0.010" to 0.030" in diameter).

The sealing ring can be attached to the pushwire in many ways. The preferred method is swaging. Interference fitting and soldering are examples of other methods that may be used. In the preferred embodiment the sealing ring is composed of the same material as that of the pushwire. This material is preferred to be stainless steel, although other materials, such as Platinum—Tungsten alloys, may be used.

An electro-active polymer may be used for the sealing ring. The passage of electric current through the pushwire will reversibly increase the volume of the sealing ring, including its diameter. When the sealing ring expands, it contacts the walls of the microcatheter and creates a seal. When using an expandable sealing ring, a narrower distal region (b) for the microcatheter may not be needed.

There are numerous ways that a sealing ring on the pushwire can be used to create a seal that will permit the capture member to pass through as well as facilitate postconditioning. The embodiments above are only examples.

The preferred embodiment is a microcatheter with a single-walled balloon operated in conjunction with a pushwire-bearing a sealing ring. The profile of the microcatheter narrows 120 at the distal end, such that when the microcatheter is mounted on the pushwire, the sealing ring only creates a seal when the sealing ring is in the narrower region (b) of the microcatheter.

A double lumen catheter, having a separate lumen for the inflating fluid, would not need a seal around the surface of the pushwire. The second lumen for the balloon-inflating fluid would be within the walls of the microcatheter itself. Even without supports (e.g. in a floating double lumen design), both tubes are advanced simultaneously making the entire assembly more rigid.

The sealing ring allows for the saline solution, pushwire, and capture member to share a single lumen. In the embodiment shown FIGS. 1, 2A-B, there is space 126 between the pushwire and the luminal wall of the microcatheter to allow the inflating solution to travel through and inflate the balloon. Additionally, this space ensures reduced friction between the clot capture member and the microcatheter, during the translation of one with respect to the other. The sealing ring is positioned proximally to the capture member. The balloon microcatheter has a locally double lumen, at the locus of the balloon 100 (the membrane of the balloon being a lumen)—but a single-wall everywhere else. The inner lumen of the microcatheter bears inflating holes 122 (two holes in the embodiment shown) that connect the lumen of the balloon to the inner layer, to let the inflating fluid reach the cavity of the balloon. When translated into the narrower portion of the microcatheter, the sealing ring creates a seal that prevents the saline solution from flowing passed the sealing ring and freely out of the distal end of the microcatheter. Once the sealing ring 104 is advanced into the narrower portion of the microcatheter (b), pumping saline solution through the proximal end of the microcatheter will result in the inflation of the balloon.

As noted previously, the sealing mechanism is on the pushwire and not protruding from the inner wall of the catheter, and here we detail why it is preferred. Had it been on the microcatheter, the capture member would need to pass through the seal and might become jammed in the process. In other words, such a design would be problematic because in order to prevent the inflating solution from flowing out the distal end of the microcatheter, the lumen of the microcatheter would need to be flush with the pushwire, at some location distal to the balloon. This seal around the pushwire would interfere with the translation of the capture member.

The sealing ring is preferred to be rounded on both the proximal and distal ends to promote ease of entering the narrower portion of the microcatheter as well as re-entering the microcatheter. The sealing ring would only need to re-enter the microcatheter if the microcatheter is pulled too far away (e.g. beyond the proximal end of the sealing ring) from the capture member during the procedure. However, it is suggested that the microcatheter cover the sealing ring at all times. That is to say that the operator should not pull the microcatheter proximally to the extent that the distal 118 end of the microcatheter is proximal to the sealing ring 104.

The end of the microcatheter does not widen in the preferred embodiment (although this might make it easier for the sealing ring to be put back within the microcatheter, should it fall out) because such a widening of the distal end of the microcatheter would hamper navigability of the microcatheter.

The preferred diameter shown of the pushwire is 0.010". However, pushwires with diameters ranging from 0.008" to 0.018" may be used.

Microcatheters Compatible with Pushwire-Bearing Sealing Rings

In the preferred embodiment, the inner diameter of the microcatheter (excluding the narrower region at the tip) is greater that the diameter of the sealing ring.

The inner diameter throughout the microcatheter may be the same as the diameter of the sealing ring; however this is not the preferred embodiment.

Increasing the inner diameter of the microcatheter slightly, in the preferred embodiment, will serve to prevent the fluid from being pushed forward e.g. such as is a plunger-barrel assembly, and more importantly to reduce friction between the microcatheter and the sealing ring. This friction could be meaningful given that the sealing ring would encounter it throughout its journey through the microcatheter and especially given the tortuous curves that the assembly will take. The microcatheter will have this increased diameter from the proximal end until near the distal end, where the diameter will shrink 120 to conform to the sealing ring.

In FIGS. 1, 2A-B, the inner lumen of the microcatheter narrows at the tip. This creates a seal only when the sealing ring is within the narrowed portion (b) of the lumen. The narrowed region may be at the last few centimeters of the tip, start from after the inflating holes 122, or in the last centimeter from the distal end. A slightly longer narrowed area provides for greater position flexibility for the microcatheter (relative to the clot) while being able to operate the balloon.

The length of the sealing area (b)—the portion of the microcatheter that is narrower and thereby creates a seal when the sealing ring is inside—is less than the length of the pushwire between the distal end of the sealing ring and the proximal end of the capture member (a). This allows for the capture member to be fully released, while affording the operator the option to either have a seal or not have a seal. Without a seal, a bolus of contrast agent can be injected through the microcatheter and be released through the distal end of the microcatheter. Compounds to facilitate clot removal, accelerate healing of the blood vessel, minimize reperfusion injury etc. may be delivered through the lumen of the microcatheter to the area of the clot/infarct region. When the seal is made, the balloon can be inflated. An additional constraint/consideration is that the distance between the balloon and the capture member should be short in order to minimize the chance of interference by a collateral artery during postconditioning. If another blood vessel were to intersect the occluded artery, between the clot and the balloon, then the balloon would not be able to cut off blood supply entirely during postconditioning. In other words the collateral blood vessel would not be blocked and continue supplying blood even when the balloon was fully inflated. In the preferred embodiment shown, (a) is approximately 8 mm and (b) is approximately 5 mm.

Specifications follow for the preferred embodiment shown in FIGS. 1, 2A-B. However a range of specifications may be used.

The wall thickness of the microcatheter is 85 µm.

In the wider part of the microcatheter, the gap 126 between the pushwire and the inner lumen of the microcatheter—if the pushwire is centered within the microcatheter—is 150 µm. However, this gap may range from 50 µm to 300 µm.

The inner diameter of the wider portion of the microcatheter is approximately 0.018 inches. However microcatheters having a range of diameters, for example, 0.014 inches to 0.021 inches, may also be used.

In the narrower part of the microcatheter, the gap 128 between the pushwire and the inner lumen of the microcatheter—if the pushwire is centered within the microcatheter—is 100 µm. However, this gap may range from 30 µm to 280 µm.

The preferred inner diameter of the narrower portion of microcatheter is 0.002" less than the inner diameter of the wider portion of microcatheter.

Extrusion is the preferred method to manufacture the microcatheter.

FIGS. 4A-4D illustrate steps for using assemblies with a single-lumen balloon microcatheter and a pushwire-mounted sealing ring in accordance with some embodiments of the present invention. When the sealing ring is in a first region 400 of the microcatheter, the balloon cannot inflate, fluid can flow through the microcatheter and into the blood vessel, and the capture member is constrained. When the microcatheter is translated proximally so that the sealing ring is in a second region 402 of the microcatheter, the balloon cannot inflate, fluid can flow through the microcatheter and into the blood vessel, and the capture member is partially constrained. When the microcatheter is translated further proximally so that the sealing ring is in a third region 404, the balloon cannot inflate, fluid can flow through the microcatheter and into the blood vessel, and the capture member is fully deployed. When the microcatheter is translated even further proximally so that the sealing ring is in fourth region 406, the balloon can inflate.

Figure 5:
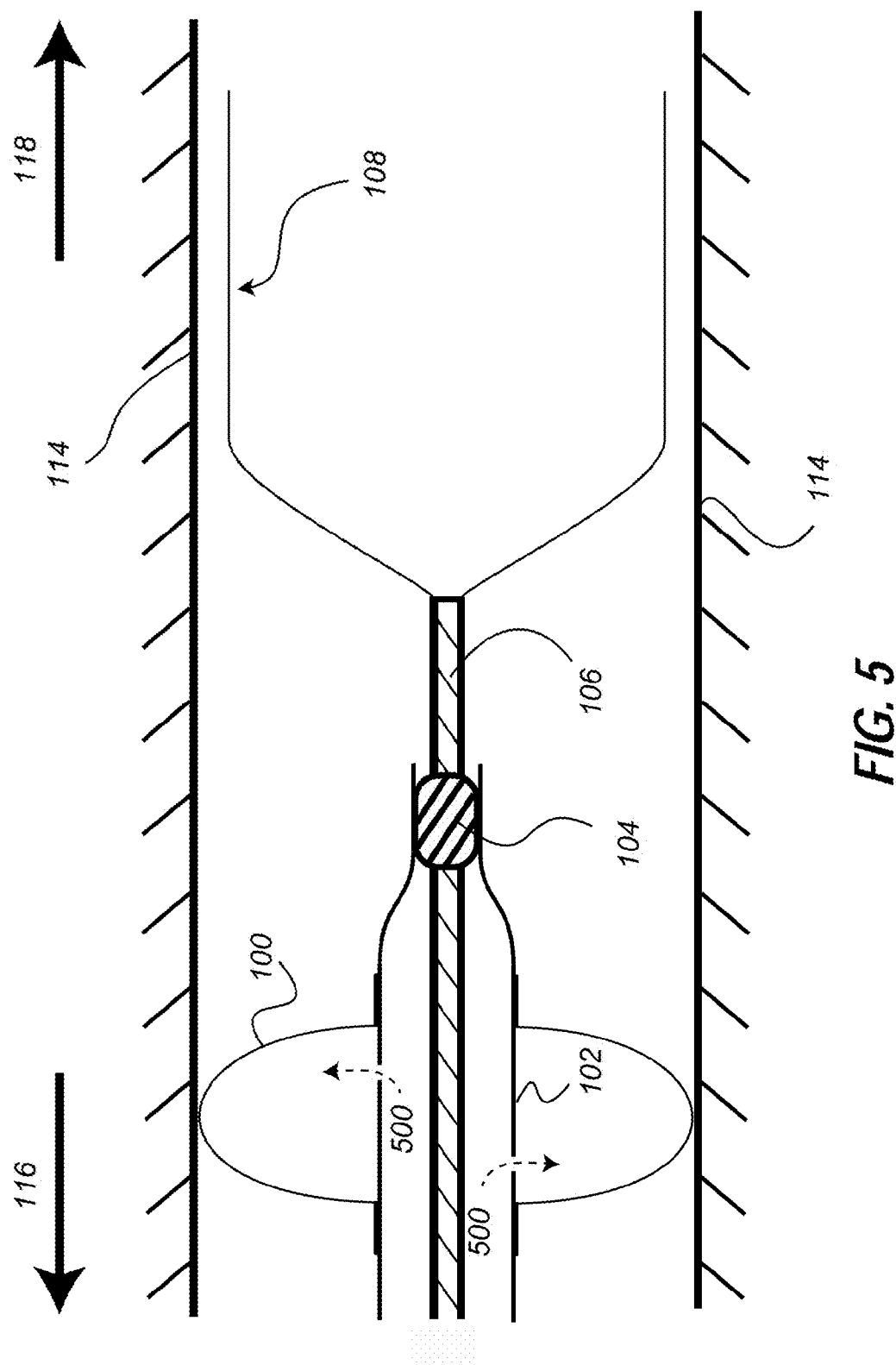

FIG. 5 illustrate steps for using assemblies with a single-lumen balloon microcatheter and a pushwire-mounted sealing ring in accordance with some embodiments of the present invention While the sealing ring is in region 4, inflating fluid 500 can be pumped into the microcatheter and will inflate the balloon. Fluid will not freely pass from the microcatheter into the blood vessel, and the capture member is fully deployed.

This slightly wider microcatheter also creates an ideal channel to deliver fluids to the infracted tissue in region of the clot and/or the clot itself. One such fluid is contrast agent. Others include agents to treat reperfusion injury or help otherwise at the site of the clot. Tissue plasminogen activator (tPA) could also be applied locally—reducing the systemic risks of bleeding—and in lower overall quantities. Agents that may minimize reperfusion injury include cyclosporine, calpain inhibitors, sodium-calcium Na+/Ca2+ exchange inhibitors, monoclonal antibodies, temperature reducing agents, or agents that slow cell metabolism. Agents that may aid in removing a clot include tissue plasminogen activator and other agents that aid in dissolving, dislodging, or macerating clots. Agents that may otherwise benefit the patient's condition include pharmaceuticals or compounds commonly used for treating clots, preventing restenosis, intravascular device coatings such as vasodilators, namodopene, sirolimus, paclitaxel, agents that promote the entanglement or attachment of a clot with a clot capture member such as fibronectin. The preferred embodiment will therefore provide an opportunity to use drugs that may help lessen the ischemic and reperfusion injuries and/or speed recovery.

Figure 6:
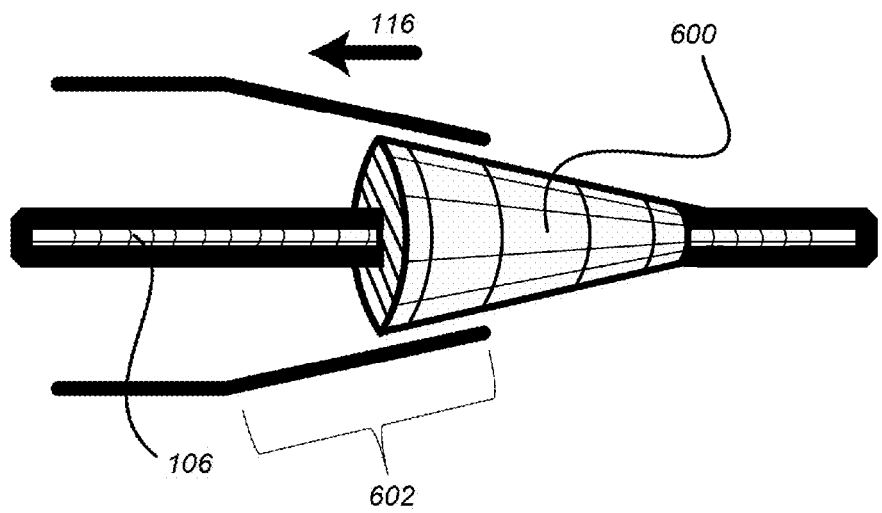
FIG. 6 illustrates a sealing ring with a conical shape and a complementary microcatheter in accordance with some embodiments of the present invention.

The sealing ring may come in various shapes and dimensions. The sealing ring need not be shaped so as to resemble a cylinder with a substantially circular base. As shown in FIG. 6, the sealing ring 600 may be shaped as a cone in accordance with some embodiments of the present invention. In this cone shape, it may be configured to fit (either partially or fully) into a corresponding narrow section 602 of the microcatheter.

Figure 7A:
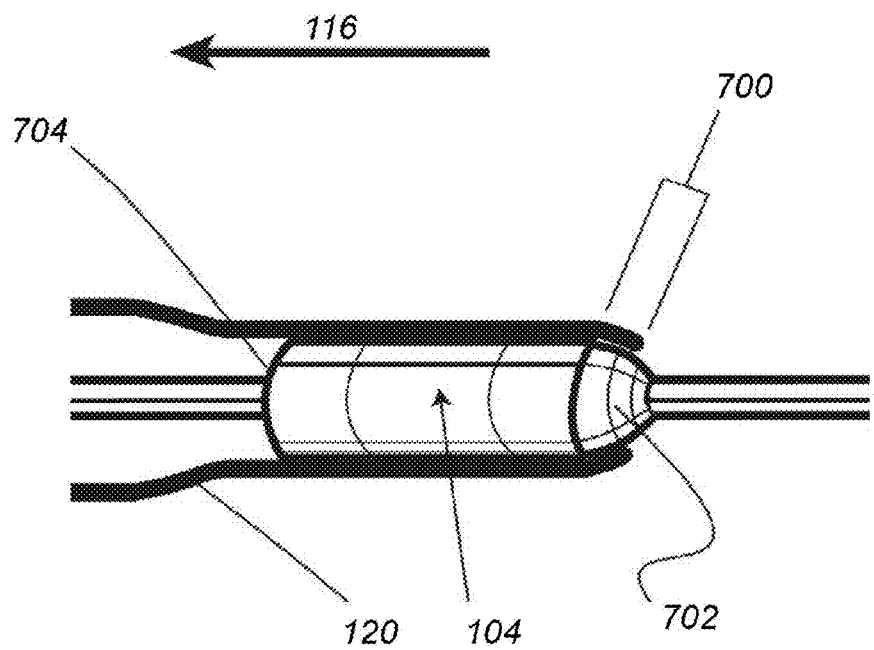
FIGS. 7A-7B illustrate alternative microcatheter designs for preventing a sealing ring from advancing beyond the distal end of the microcatheter in accordance with some embodiments of the present invention.
Figure 7B:
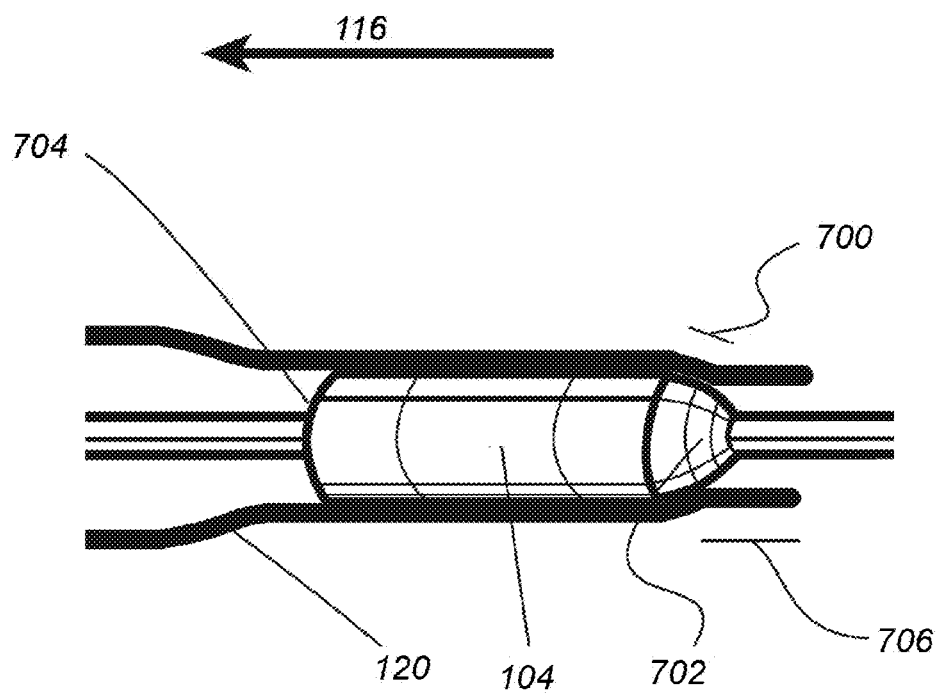

FIGS. 7A-7B illustrate, according to some embodiments, alternative microcatheter designs for preventing the sealing ring 104 from advancing beyond the distal end of the microcatheter. In FIG. 7A, the distal end of the microcatheter 700 tapers after the sealing region. In FIG. 7B, an additional region 706 with a diameter be too narrow to permit passage of the sealing ring 104 further stabilizes the blockage, ensuring that the sealing ring will be less likely to pass through even if force is exerted. The sealing ring may be designed to not fully enter into a sealing region but instead for only the end (or the distal portion of the sealing ring) to contact one or more narrowing regions of the microcatheter. The microcatheter may have either sharp or rounded edges on one or more sides, and the slope of the edges may vary. The microcatheter diameter may vary linearly, sharply, or gradually. The narrowing regions of the microcatheter need not be manufactured contiguously. For example, a tube with a smaller diameter than the microcatheter (or another ring) may be attached within the microcatheter (in effect, narrowing the lumen of a distal portion of the microcatheter). Another example is where the distal end of the balloon wraps around and into the distal end of the microcatheter to create the narrower sealing (or ring stopping) portion.

Balloons Compatible with Pushwire-Bearing Sealing Rings

In all embodiments herein having a balloon, the membrane of the balloon may be constructed from various materials. Polypropylene is preferred but other materials may be used such as, thermoplastic polymers, elastomeric silicones, latexes, other polymers or a blend thereof. An example is ENGAGE® (Dow Chemical). To reliably occlude while not damaging the artery, the balloon is soft, compliant and operated under a range of low pressures. The balloon may occlude the vessel at inflation pressures ranging from 0.1 to 5 atm. The balloon is preferred to be one-size-fits-all-cerebral-vessels with balloon diameters ranging from 1 to 5 mm in the inflated state. Alternatively, various microcatheters may be manufactured with balloons of different sizes to accommodate a range of occluded vessel diameters. The target diameters of the different sized balloons may be 1 to 5 mm (different sizes for different diameter arteries). The length of the balloon 100 is preferred to be 10 mm (short for navigability). However, a range of balloon lengths may be used (for example up to 30 mm).

The balloon may be coated with various coatings to reduce friction between the balloon and the vessel and also to avoid adhesion of thrombus. For example, a hydrophilic coating such as polytetrafluoroethylene, is preferred.

Radiopaque marker-bands FIG. 1, 124 are preferred to be placed near the extremities of the balloon. It is preferred to place two marker-bands, one near the proximal end of the balloon and one near the distal end. In the preferred embodiment FIG. 1, the marker-bands are around the microcatheter, but within the inner lumen of the balloon. Alternatively, the marker-bands may be embedded within the plastic wall of the microcatheter. Radiopaque materials may also be incorporated within the material of the balloon membrane, or used to coat the balloon. The radiopaque materials will aid the operator in seeing the position, state of expansion, and rate of expansion of the balloon.

Figures 8A, 8B:
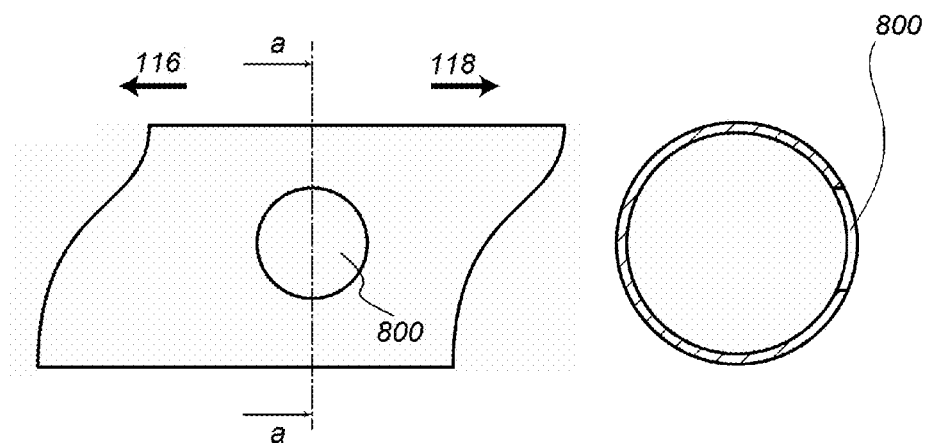
FIGS. 8A-B and 9 illustrate alternative passage shapes designed for the flow of inflating fluid between a catheter and an inflatable flow modulation member in accordance with some embodiments of the present invention.
Figure 9:
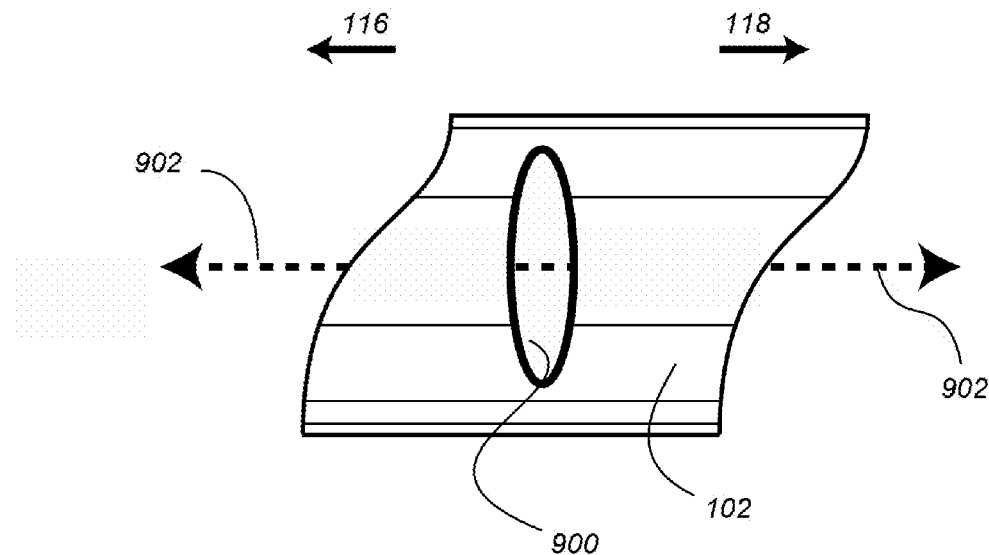

FIGS. 8-9 illustrate a passage for the flow of inflating fluid between a catheter and an inflatable flow modulation member in accordance with some embodiments of the present invention. In FIG. 8, this passages or inflating hole 122 is cylindrical with a circular base 800 and a diameter of, for example, 100 μm. Other diameters may also be used including, but not limited to, the range of 30 μm to 200 μm. FIG. 9 illustrates an alternative embodiment, in which an inflating hole is cylindrical, but with an elliptical base 900, so that the smallest diameter is parallel to the central axis 902 of the microcatheter 102 (so as to reduce the likelihood of the capture member jamming in thean inflating hole). The dimensions of the inflating hole shown in FIG. 9 are 30 μm at the smallest diameter and 100 μm at the largest diameter. In other embodiments the shape and/or size of the base may vary. The inflating holes may be cut into the microcatheter or catheter using methods including, but not limited to, electron beam drilling, laser drilling, and classical machining.

The balloon is attached to the microcatheter in the attachment regions 130 on either side of the inflating membrane. The attachment regions are contiguous bands around the microcatheter. The attachment regions keep the inflating solution from flowing out of the balloon. Many methods may be used to attach the balloon to the microcatheter (e.g. fusion bonding, ultrasonic welding, solvent bonding, induction welding, and dielectric welding).

Embodiments that utilize programmed flow modulation may be used to standardize operators' work and/or to automatically detect and adjust the pressure in the flow modulation balloon to exert the desired pressure on the blood vessel walls. Pressure sensing capabilities make it easier to inflate the balloon according to the varying radii of different blood vessels. Thus, a balloon flow modulation system according to some embodiments may be more precise and responsive, may require less work and judgment on the part of an operator, and may keep detailed treatment records.

A multi-port adapter (e.g., a dual port adaptor) may be attached to the proximal end of the conduit for the inflating fluid (for example a balloon microcatheter). The adapter has a port for the endovascular devices, used to access the lumen of the microcatheter, as well as a port for attaching a removable pressure transducer. The transducer is either manually operated (e.g. by a syringe) or by an automatic pump (e.g. peristaltic pump). The pressure transducer will inflate and deflate the balloon to create postconditioning (sequence of blocking and restarting blood flow).

The pressure transducer apparatus could be, for example, peristaltic pumps such as the Ismatec ICC 3 Channel 8 Roller Peristaltic Pump (Cole Parmer, Ill., USA) or the mph micropump (Bartels, Munich, Germany). The pump should have a flow rate superior to 5 mL per minute in order to inflate the balloon in less than 10 seconds.

A preprogrammed (or programmable) electronic control system is preferred to control the cycles of the pump according the desired postconditioning protocol. The electronic control system is preferred to be a freestanding small chip. However, various types of computers and electronics may also be used. Pressure data may be collected, preferably by inserting a pressure sensing probe (such as a manometer) into a third port at the proximal end of the conduit for the inflating fluid (for example a balloon microcatheter). This pressure data is preferred to be processed by the electronic system. If at any time the pressure exceeds a threshold that may compromise the mechanical integrity of the balloon, the electronic system will cause the pump to remove inflating fluid from the balloon and reduce pressure.

Along with saline solution, contrast agent may be part of the inflating solution so that the inflation of the balloon may be observed with angiography.

A subsystem may include pneumatic and/or hydraulic parts. The balloon may be deflated quickly via withdrawing a piston, opening a valve, or using a vacuum.

Methods of Using Pushwire-Bearing Sealing Rings

Figure 10A:
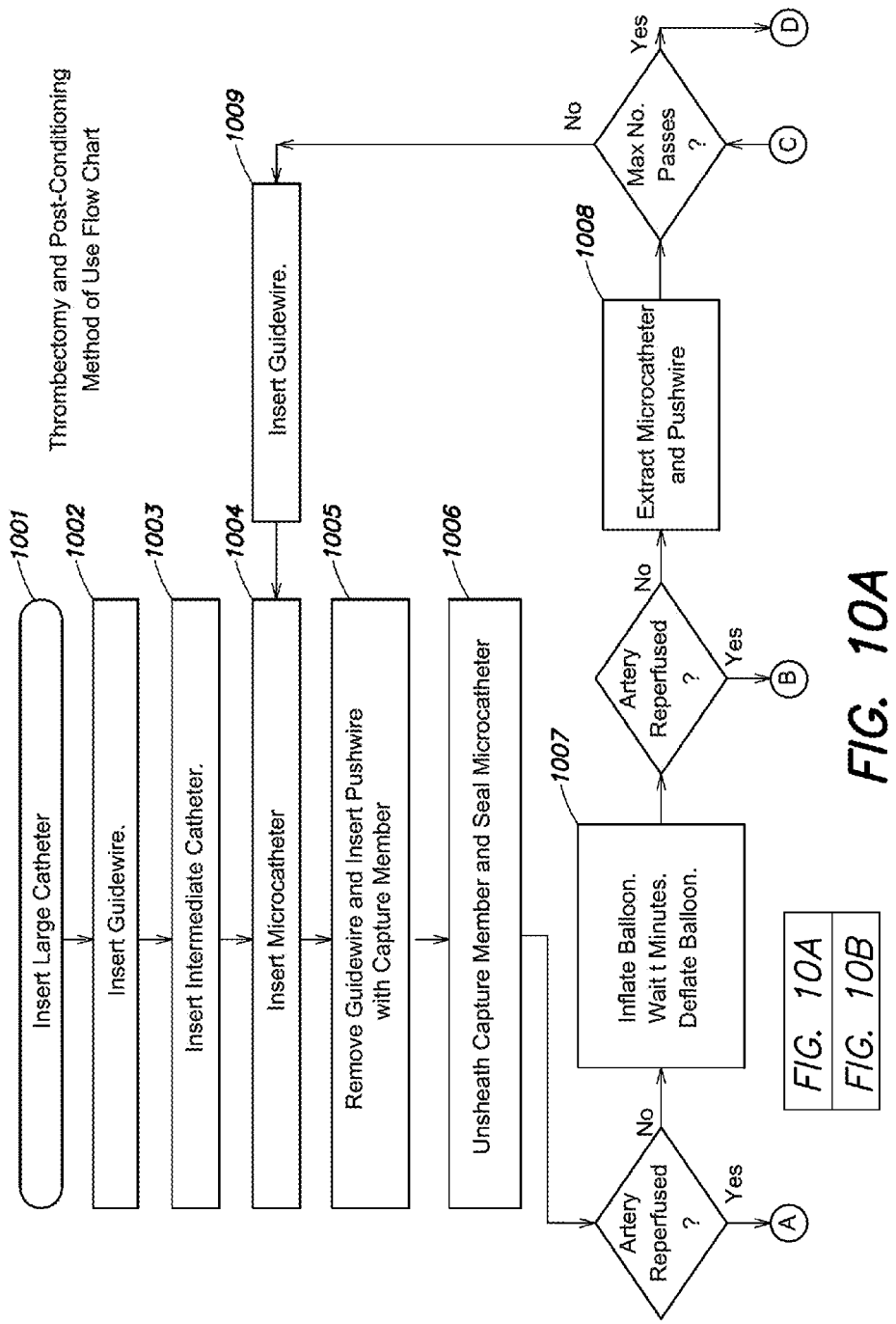
FIGS. 10A-B is a method flow chart for performing postconditioning and mechanical thrombectomy in accordance with some embodiments of the present invention.
Figure 10B:
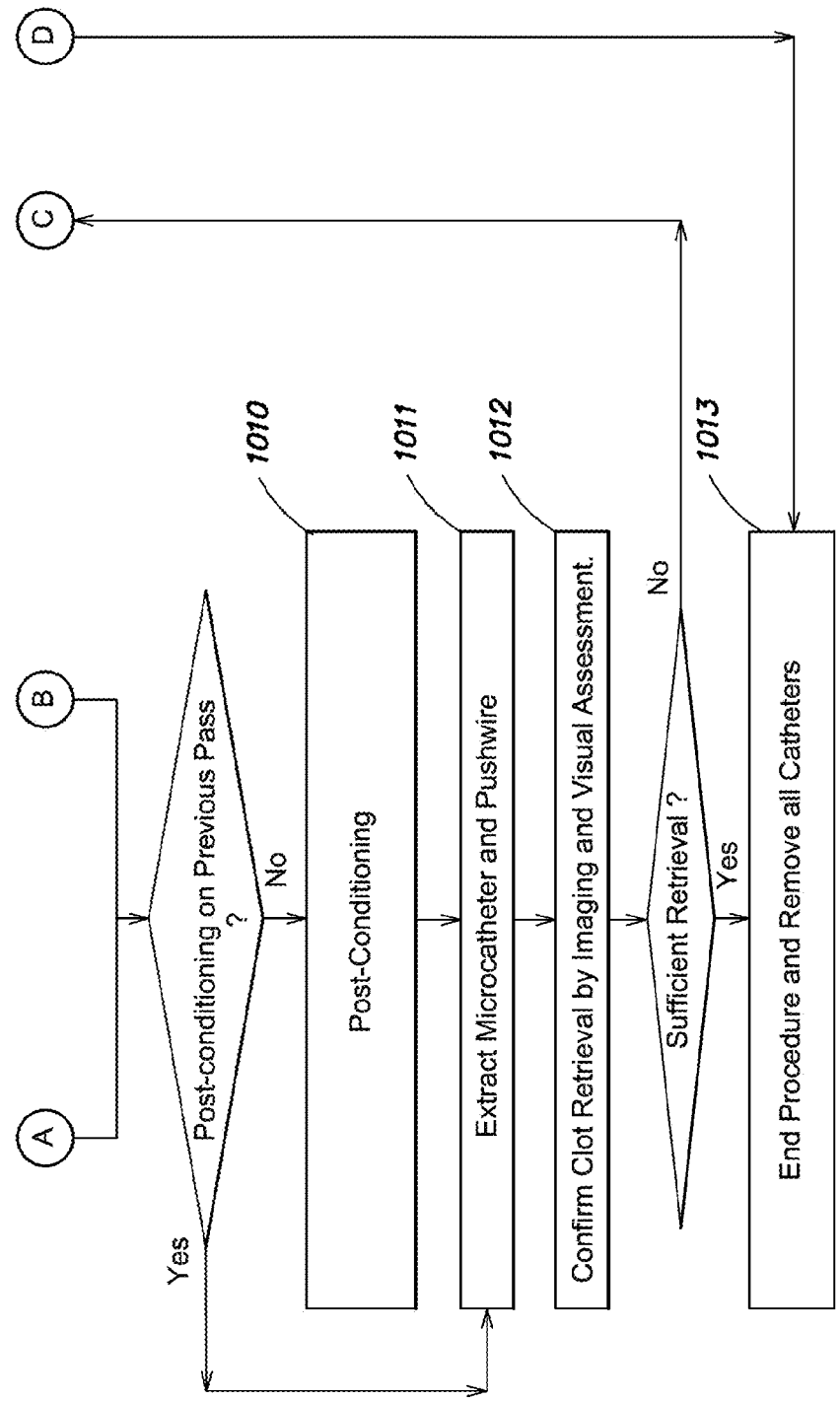

FIG. 10 is a process flow chart for performing postconditioning with mechanical thrombectomy in accordance with some embodiments of the present invention. For example, the steps in FIG. 10 may be applied to assemblies with a single-lumen balloon catheter and a pushwire-bearing sealing ring.

In step 1001, a large catheter (e.g., a 6 French catheter) is inserted and guided, for example, from the femoral artery to the neck. In step 1002, a guidewire is inserted through the large catheter and navigated so that its distal end is at a position distal to the location of the clot in, for example, a cerebral artery.

In optional step 1003, an intermediate catheter (e.g., a 5 French catheter) is inserted over the guidewire and advanced so that its distal end is at a position (e.g., the sphenoidal (M1) segment of the middle cerebral artery (MCA)) that is closer to the clot than the distal end of the large catheter. In the event of subsequent passes, an intermediate catheter saves the time required for navigating a new guidewire from the distal end of the larger catheter a position distal to the location of the clot.

In step 1004, a microcatheter is inserted over the guidewire and advanced so that its distal end is at a position distal to the clot. The microcatheter has a distal region in which its internal diameter decreases. The microcatheter may but need not advance any further than the distal end of the guidewire. In step 1005, the guidewire is removed from the microcatheter and replaced with a pushwire. The pushwire has a clot capture member coupled to its distal end and a sealing ring proximal to the clot capture member. The clot capture member has a self-expanding region adapted for engaging with a clot (i.e., an "active region"). The active region of the clot capture member should be advanced within the microcatheter so as to be adjacent to the clot. Thus, 1006, the active region will expand and engage with the clot. During all passes with the clot capture member, the microcatheter should be sufficiently retracted so that the sealing ring coupled to the pushwire enters the narrow distal region of the microcatheter and creates a seal within the microcatheter lumen around the pushwire for retaining inflating fluid in the microcatheter.

Following step 1006, the status of reperfusion should be assessed and the elapsed time tracked. The reperfusion status may be assessed by, for example, injecting a contrast agent (e.g., a bolus of radiopaque solution) through the large catheter and performing angiography to view the perfusion of the contrast agent. Suitable contrast agents may include, but are not limited to, lothalamate meglumine, diatrizoate meglumine, and other iodine-containing solutions.

In step 1007, if the blood vessel has not been sufficiently reperfused, then inflating fluid is pumped into the single microcatheter lumen, thus inflating the flow modulation member and occluding the blood vessel. A determined period of "wait" time t (e.g., 5 minutes) is allowed so that the clot capture member may expand into and engage the clot. After wait time t, the flow modulation member is deflated and the status of reperfusion is assessed again. In step 1008, if the blood vessel has not been adequately reperfused, then the microcatheter and pushwire are removed. If a predetermined maximum number of passes have not yet been completed, a new pass is initiated in step 1009 with the insertion of a new guidewire. Steps 1004-1009 are repeated in subsequent passes until either (1) the blood vessel is sufficiently reperfused, or (2) the predetermined maximum number of passes have been completed.

If the blood vessel is sufficiently reperfused after step 1006 or step 1007, postconditioning will be performed using the flow modulation member unless postconditioning was performed on a previous pass. If reperfusion is sufficient and postconditioning has not been performed on a previous pass, the flow modulation member (i.e., a balloon) is inflated and deflated in step 1010 according to a determined series of one or more postconditioning cycles. Preferred examples of postconditioning cycles will be described in greater detail below.

According to some embodiments of the present invention, the balloon is inserted with, attached to and flush with the external wall of, the microcatheter. The balloon may be inflated and deflated by either manual or automatic pumping of inflating fluid in and out of the microcatheter lumen, which is continuous with the balloon lumen via inflation holes. When inflating fluid is pumped through the microcatheter, it flows through the inflation holes in the catheter lumen wall and into the balloon lumen. The balloon membrane expands against the blood vessel, blocking a substantial portion of the vessel's lumen. In a preferred embodiment, the balloon membrane contacts the inner lumen of the blood vessel to create a complete occlusion of blood flow. The balloon membrane is flexible so that it will conform to the blood vessel's walls. By having an blood flow-occluding balloon in place, a stable hemodynamic environment is created, which helps to minimize the risk of distal embolization. In some embodiments, this increasing the benefits of postconditioning by controlling when reperfusion first occurs, so that postconditioning may be performed from the onset of reperfusion.

Upon removal of inflating fluid from the microcatheter, the balloon also empties (i.e., deflates) and gradually resumes its former shape, once again becoming flush with the external wall of the microcatheter. With deflation, the occlusion is gradually removed and the blood flow gradually restored.

If reperfusion is sufficient but postconditioning has already been performed on a previous pass, the microcatheter and pushwire are removed from the body. In a given pass, if less than wait time t has elapsed since the clot capture member was unsheathed in step 1006, the microcatheter and pushwire should not be removed. If and when wait time t elapses, the microcatheter and pushwire are removed in step 1011. To simultaneously remove the microcatheter and pushwire, an operator may hold the proximal ends of the pushwire and microcatheter together and translate them proximally until they are completely withdrawn from the body in accordance with some embodiments. The clot capture member is not resheathed in the microcatheter during its exist from the body, but it does pass, along with the microcatheter and pushwire, within and through the intermediate catheter (if present) and the larger catheter. According to further embodiments, the intermediate and/or larger catheters remain in place while the microcatheter and pushwire are removed from the body. Optionally, suction may be applied through the large catheter to limit the dispersion of secondary emboli.

In step 1012, an operator determines whether clot material has been sufficiently removed by the clot capture member. The status of reperfusion may inform this inquiry. Thus, in some embodiments, the status of reperfusion is assessed by, for example, injecting a contrast agent through the large catheter and performing angiography to view the perfusion of the contrast agent. In some embodiments, the clot capture member itself is inspected (e.g., visually) to determine whether the retrieved clot material is sufficient. Sufficiency may depend on numerous factors including, but not limited to, changes in perfusion.

Following step 1012, if a sufficient amount of clot material has been retrieved, as evidenced in some embodiments by the status of reperfusion, the procedure is completed and any remaining catheters are removed from the body according to step 1013. However, if none or an insufficient amount of clot material has been retrieved, and if a predetermined maximum number of passes have not yet been completed, a new pass is initiated in step 1009 with the insertion of a new guidewire. Steps 1004-1009 are repeated in subsequent passes until either (1) a sufficient amount of clot material has been retrieved, or (2) the predetermined maximum number of passes have been completed.

Figure 11:
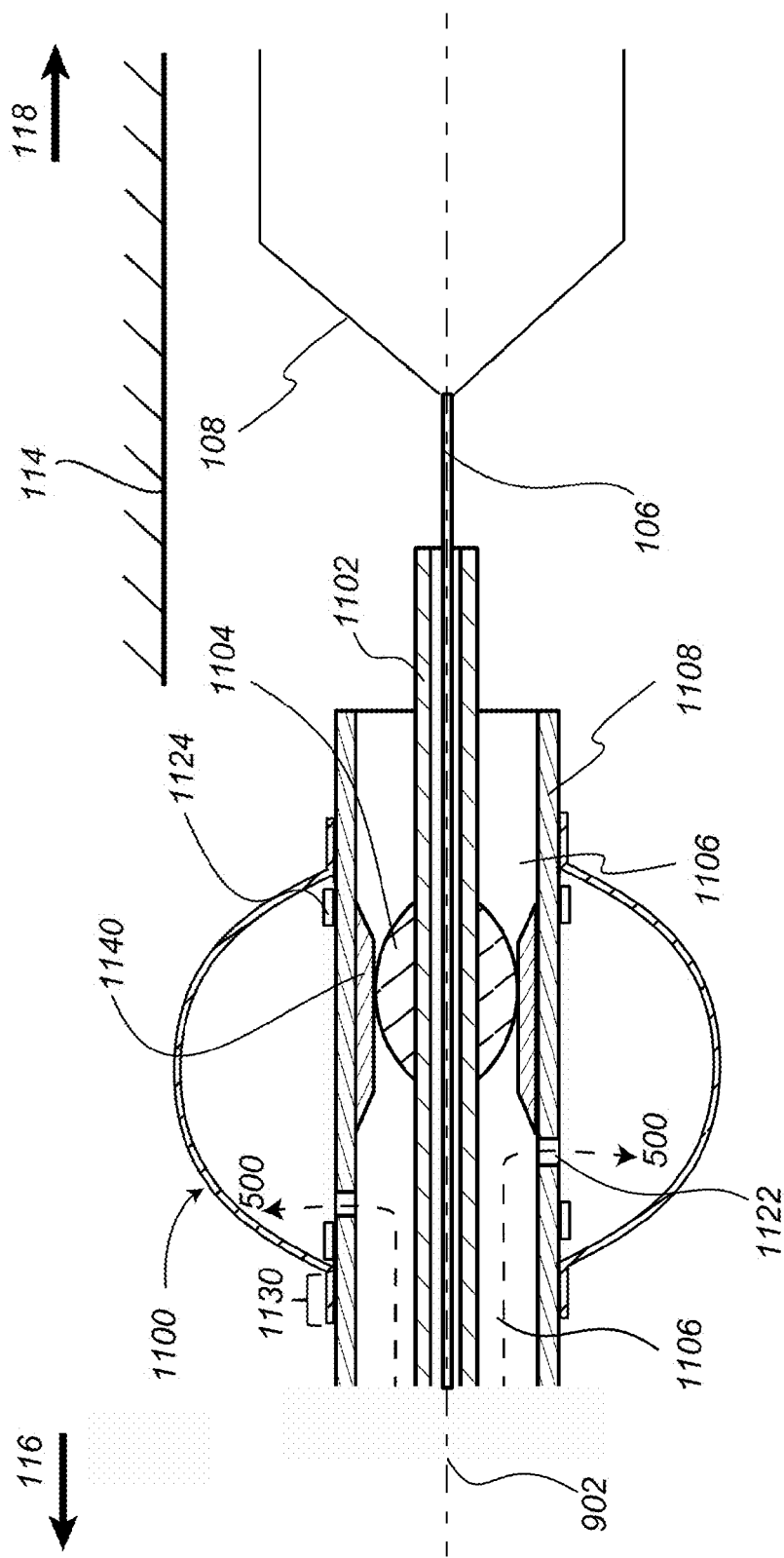
FIG. 11 illustrates a sealing ring system with an intermediate balloon catheter in accordance with some embodiments of the present invention.

Intermediate Single-Lumen Balloon Catheters with Microcatheter-Bearing Sealing Rings The use of a movable seal disposed within a lumen that has a sealing region is certainly applicable beyond the pushwire/microcatheter context. In FIG. 11, for example, a rounded sealing ring 1104 is attached to a microcatheter. The sealing region 1140 is on the inner lumen of an intermediate catheter 1108. The membrane for the balloon 1100 attaches to the intermediate catheter 1108 in the attachment regions 1130. When the rounded sealing ring 1104 is placed in the sealing region 1140 of the intermediate catheter, defined by a polymeric tube that may be made from the same material as the intermediate catheter (a different material may also be used) that creates a narrower lumen, inflating fluid 500 pushed through the lumen of the intermediate catheter 1108 will flow through the inflating holes 1122.

The embodiment shown in FIG. 11 is an assembly composed of a sealing ring 1104 mounted on a microcatheter 1102 and a single lumen intermediate catheter 1108, which provides enhanced navigability and allows for the delivery of the capture member 108 at the location of the clot. Clots tend to lodge in the Middle Cerebral Artery, where the vasculature is particularly tortuous. Using a sealing ring design eliminates the need for an additional lumen on the intermediate catheter and therefore increases flexibility.

The preferred length of the sealing ring is 4 mm. However, different dimensions for the sealing ring may be used (e.g. from 2 mm to 10 mm in length). The diameter of the sealing ring is preferred to be the same as the inner diameter of the narrower region of the intermediate catheter. It is anticipated that matching diameters, 0.046", will provide adequate sealing while minimizing the risk of assembly jamming. However, different dimensions for the sealing ring may be used (e.g. from 0.0350" to 0.055" in diameter).

The sealing ring can be attached to the microcatheter in many ways, for example: solvent bonding, gluing and interference fitting. In the preferred embodiment the sealing ring is composed of the same material as that of the microcatheter; however, other materials may be used.

The insert for the narrowing of the lumen can be attached to the intermediate catheter in many ways, for example: solvent bonding and interference fitting. In the preferred embodiment the narrowing of the lumen is composed of the same material as that of the microcatheter; however, other materials may be used. The intermediate catheter 1108 and the sealing region insert 1140 may be manufactured as one part. In this case, the intermediate catheter would be extruded at the desired diameter, for example 4 Fr inner diameter. The narrower region may be created by pinching or heat-forming such that the both the inner and outer diameter of the intermediate catheter may be locally reduced simultaneously.

There are numerous ways that a sealing ring on the microcatheter can be used to create a seal that will permit the clot to pass through the intermediate catheter as well as facilitate postconditioning. The embodiments above are only examples.

The sealing ring allows for both the saline solution and microcather to share a single lumen. In the embodiment shown FIG. 11, there is space 1106 between the microcatheter and the luminal wall of the intermediate catheter 1108 to allow the inflating solution to travel through and inflate the balloon. Additionally, this space ensures reduced friction between the clot capture member and the microcatheter, during the translation of one with respect to the other. The sealing ring may positioned proximally to the portion of the microcatheter that will slide through the clot before deploying the capture member (e.g. 25 mm proximal to the distal tip of the microcatheter). The inner lumen of the intermediate catheter bears inflating holes 1122 (two holes in the embodiment shown) that connect the lumen of the balloon to the inner lumen 1106 of the intermediate catheter, to let the inflating fluid reach the cavity of the balloon. When translated into the narrower portion of the intermediate catheter, the sealing ring creates a seal that prevents the saline solution from flowing passed the sealing ring and freely out of the distal end of the intermediate catheter. Once the sealing ring 1104 is advanced into the narrower portion of the intermediate catheter 1140, pumping saline solution through the proximal end of the intermediate catheter will result in the inflation of the balloon.

The sealing ring is preferred to be rounded to promote ease of entering the narrower portion of the intermediate catheter. By only contacting at one point, friction is minimized and the microcatheter can pass through the intermediate catheter without jamming. The sealing ring would only need to re-enter the intermediate catheter if the microcatheter is pushed too far away (e.g. beyond the distal end of the intermediate catheter).

The end of the intermediate catheter may be the same diameter as the non-sealing areas of the intermediate catheter, as is illustrated in this embodiment. Having a wider lumen allows the clot to be drawn into the intermediate catheter (along with the capture member) with less potential for resistance.

The preferred outer diameter shown of the microcatheter is 2.3 Fr. However, microcatheter with diameters ranging from 1.5 Fr to 3 Fr may be used.

Intermediate Catheters Compatible with Microcatheter-Bearing Sealing Rings

The inner diameter throughout the intermediate catheter may be the same as the diameter of the sealing ring; however this is not the preferred embodiment.

The narrowed region may be 4 mm long and its center located 22 mm from the distal end of the intermediate catheter. The region of the microcatheter distal to the sealing ring 1104 has sufficient length so as to not let the sealing ring interfere with the clot when positioning the microcatheter adequately before positioning the capture member adjacent to the clot.

Specifications follow for the preferred embodiment shown in FIG. 11. However a range of specifications may be used:

The wall thickness of the intermediate catheter is 100 μm.
In the wider part of the intermediate catheter, the gap 1106 between the outer diameter of the microcatheter and the inner diameter of the intermediate catheter—if the microcatheter is centered within the intermediate catheter—is 283 μm. However, this gap may range from 150 μm to 400 μm.
The inner diameter of the wider portion of the intermediate catheter is 4 Fr. However intermediate catheters having a range of diameters, for example 3 Fr to 5 Fr, may also be used.

This slightly wider intermediate catheter also allows for two ideal channels to deliver fluids to the infarcted tissue, in region of the clot and/or the clot itself. With both channels, medicine can reach this infarct area both during and in between clot retrieval passes. When the ring is not in the sealing region, both channels are available. Alternating applications of different medications may be used. One such fluid is contrast agent. Others include agents to treat reperfusion injury or help otherwise at the site of the clot. Tissue plasminogen activator (tPA) could also be applied locally—reducing the systemic risks of bleeding—and in lower overall quantities. Agents that may minimize reperfusion injury include cyclosporine, calpain inhibitors, sodium-calcium Na+/Ca2+ exchange inhibitors, monoclonal antibodies, temperature reducing agents, or agents that slow cell metabolism. Agents that may aid in removing a clot include tissue plasminogen activator and other agents that aid in dissolving, dislodging, or macerating clots. Agents that may otherwise benefit the patient's condition include pharmaceuticals or compounds commonly used for treating clots, preventing restenosis, intravascular device coatings such as vasodilators, namodopene, sirolimus, or paclitaxel. The preferred embodiment will therefore provide an opportunity to use drugs that may help lessen the ischemic and reperfusion injuries and/or speed recovery.

The sealing ring may come in various shapes and dimensions. The sealing ring need not be shaped so as to resemble an ellipsoid with a hole through the center for the microcatheter. Indeed, it may be of numerous shapes.

Balloons Compatible with Intermediate Catheter-Bearing Sealing Rings

This balloon may be longer than the balloon for the single lumen microcatheter with sealing ring. In this embodiment, the proximal end of the balloon would be located 29 mm from the distal end of the intermediate catheter, such that it begins proximal to the location of the sealing holes and extends up to the distal end of the intermediate catheter. Note that the inflation holes should be proximal to the sealing region. In the embodiment shown the inflation holes are located 26 mm from the distal end of the intermediate catheter. Positioning the inflation holes toward the proximal end of the balloon and having a longer balloon, allows the sealing region to be far enough away from the distal end of the intermediate catheter so that it does not interfere with the clot upon retrieval. A major advantage of having the balloon extend to the distal tip of the intermediate catheter is that the distance between the balloon and the capture member should be short in order to minimize the chance of interference by a collateral artery during postconditioning. If another blood vessel were to intersect the occluded artery, between the clot and the balloon, then the balloon would not be able to cut off blood supply entirely during postconditioning. In other words the collateral blood vessel would not be blocked and continue supplying blood even when the balloon was fully inflated.

In all embodiments herein having a balloon, the membrane of the balloon may be constructed from various materials. Polypropylene is preferred but other materials may be used such as, thermoplastic polymers, elastomeric silicones, latexes, other polymers or a blend thereof. An example is ENGAGE® (Dow Chemical). To reliably occlude while not damaging the artery, the balloon is soft, compliant and operated under a range of low pressures. The balloon may occlude the vessel at inflation pressures ranging from 0.1 to 5 atm. The balloon is preferred to be one-size-fits-all-cerebral-vessels with balloon diameters ranging from 1 to 5 mm in the inflated state. Alternatively, various intermediate may be manufactured with balloons of different sizes to accommodate a range of occluded vessel diameters. The target diameters of the different sized balloons may be 1 to 5 mm (different sizes for different diameter arteries). The length of the balloon 1100 is preferred to be 30 mm (to allow a sufficient wide-diameter lumen at the distal tip of the intermediate catheter). However, a range of balloon lengths may be used (for example up to 50 mm).

The balloon may be coated with various coatings to reduce friction between the balloon and the vessel and also to avoid adhesion of thrombus. For example, a hydrophilic coating such as polytetrafluoroethylene, is preferred.

Radiopaque marker-bands FIG. 11 1124 are preferred to be placed near the extremities of the balloon. It is preferred to place two marker-bands, one near the proximal end of the balloon and one near the distal end. In the preferred embodiment FIG. 11, the marker-bands are around the intermediate catheter, but within the inner lumen of the balloon. Alternatively, the marker-bands may be embedded within the plastic wall of the intermediate catheter. Radiopaque materials may also be incorporated within the material of the balloon membrane, or used to coat the balloon. The radiopaque materials will aid the operator in seeing the position, state of expansion, and rate of expansion of the balloon.

The inflating holes 1122 are cylindrical holes with a circular FIG. 5 500 base and a diameter of 150 µm. A range of diameters may also be used (e.g. from 100 µm to 400 µm). The inflating holes may be cut into the microcatheter or catheter using electron beam drilling, laser drilling, classical machining or other methods.

The balloon is attached to the microcatheter in the attachment regions 1130 on either side of the inflating membrane. The attachment regions may be contiguous bands around the intermediate catheter. The attachment regions keep the inflating solution from flowing out of the balloon. Many methods may be used to attach the balloon to the intermediate catheter (e.g. fusion bonding, ultrasonic welding, solvent bonding, induction welding, and dielectric welding).

Other Single-Lumen Balloon Catheter Embodiments of a Flow Modulation Member

Figure 12:
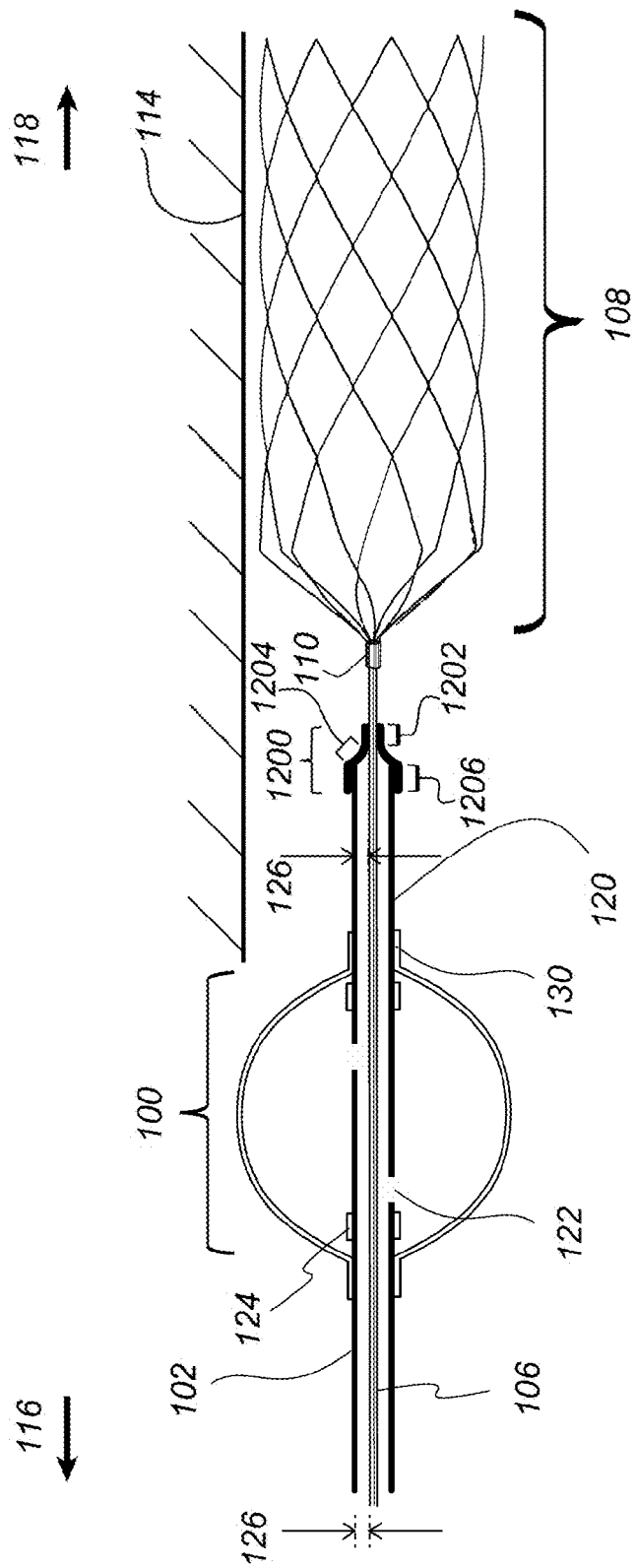
FIGS. 12-13 illustrate sealing tip designs for assemblies with a single-lumen balloon catheter in accordance with some embodiments of the present invention.

Alternatively, the lumen of the microcatheter may be tapered at its distal tip such that the distal tip creates a seal against the pushwire (herein referred to as a "sealing tip"). FIG. 12 illustrates a microcatheter with a sealing tip according to some embodiments of the present invention. The sealing tip 1200 may be constructed from an elastic material that can expand to accommodate the compressed capture member but then contract (facilitated by bending in region 1204), after the capture member passes through, to create a seal where the region of the flexible tip 1202 contacts the pushwire and allow for inflation of the balloon. The tip widens when pressed by the capture member. An example of such material is silicon rubber. The embodiment shown in FIG. 12 is but one example. In FIG. 12, the flexible tip 1200 is a single part that goes over and attaches, in region 1206, to the microcatheter. The tip is secured around the distal end of the microcatheter. FIG. 12 features a tip that extends beyond the distal edge of the microcatheter.

Figure 13:
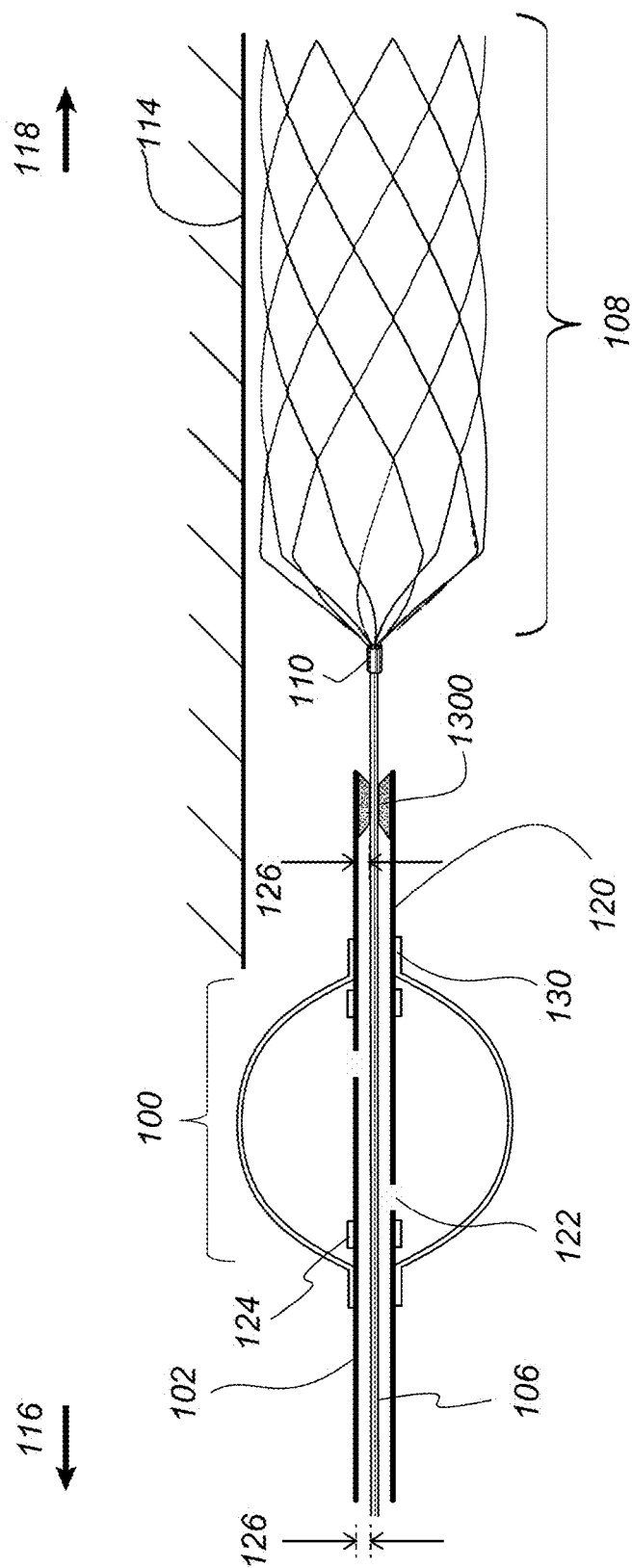

There are various ways to build a flexible tipped microcatheter. Two such embodiments are illustrated in FIGS. 12-13. FIG. 13 creates a flexible sealing region by having a spongy material 1300 inside of tip of the microcatheter. It compresses against the microcatheter walls to allow the capture member to pass through and then hugs the microcatheter to create a seal.

In flexible tipped embodiments, it is preferred to have a stent that is closed at the distal end, in order to present a focused insertion profile to the sealing tip.

Multiple-Lumen Balloon Embodiments of a Flow Modulation Member

Double-Lumen Balloon Microcatheters

A double lumen balloon microcatheter may be used in lieu of the single-lumen balloon microcatheter previously described. In this case, the profile of the inner lumen FIG. 14 1400 will be constant i.e. constant inner diameter. Here, the inflating solution 1404 would have its own dedicated lumen 1406 within the walls 1408 and 1410 of the microcatheter. The inflating solution would not come into contact with the pushwire 106 or capture member 108. Radiopaque markers 1424 delineate the extremities of the balloon.

Figure 14A:
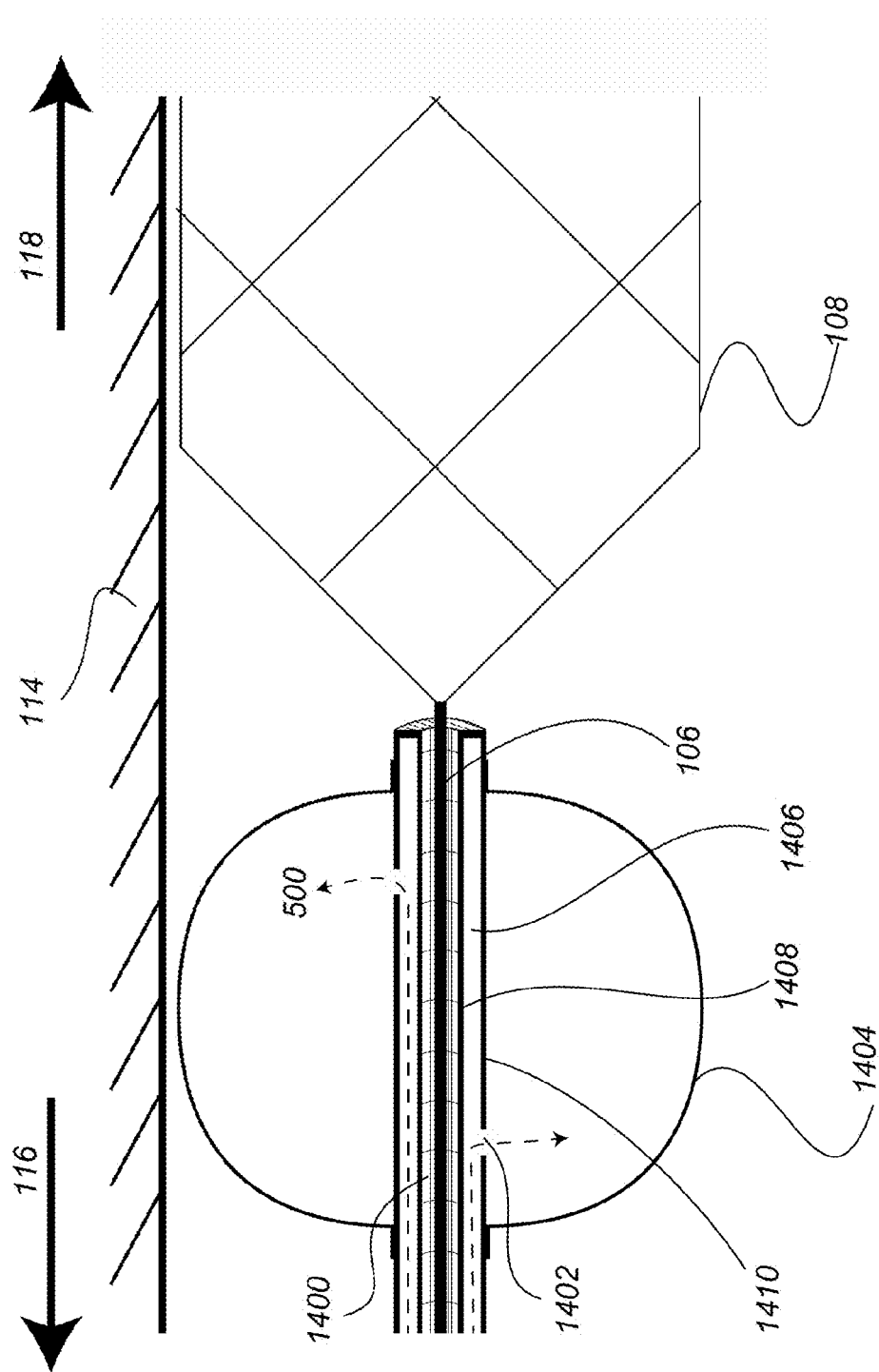
FIGS. 14A-14E illustrate a double-lumen balloon catheter in accordance with some embodiments of the present invention.
Figure 14B:
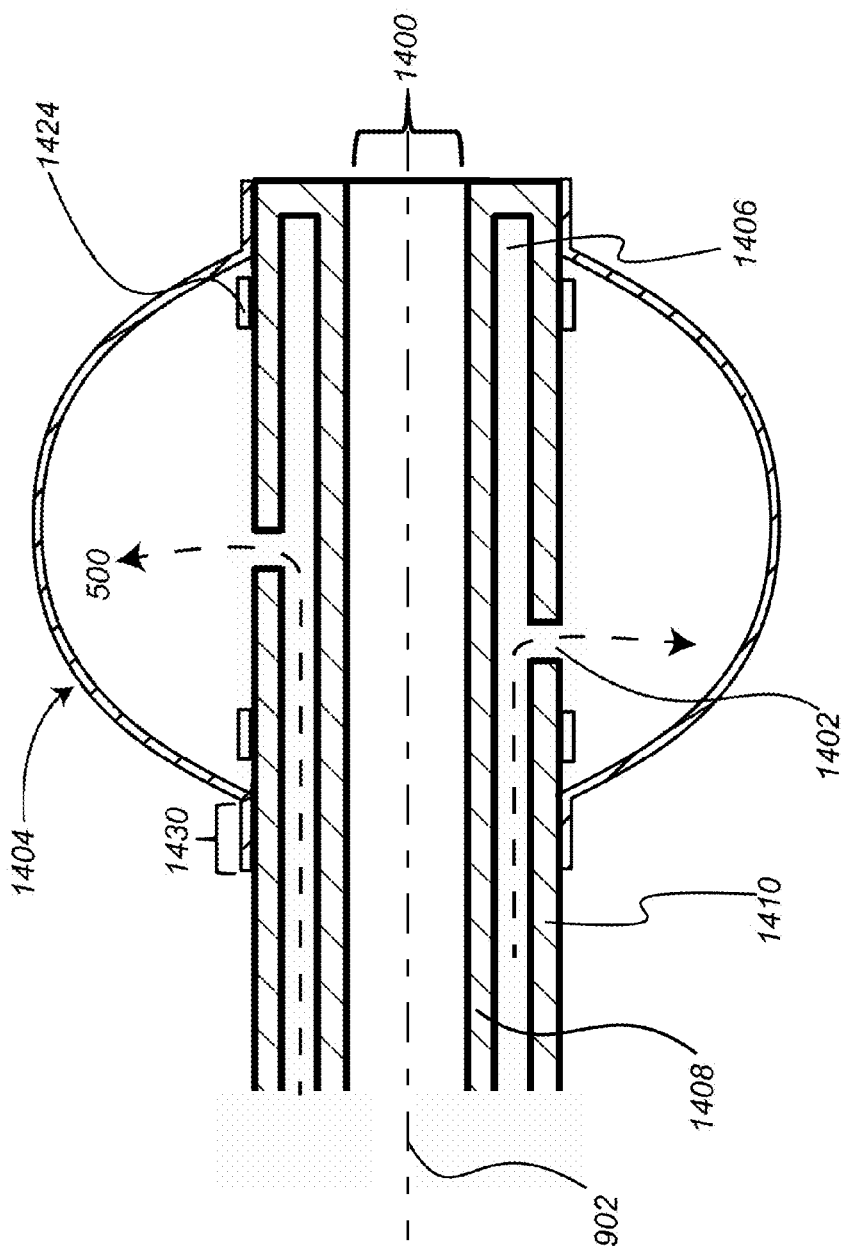
Figure 14C:
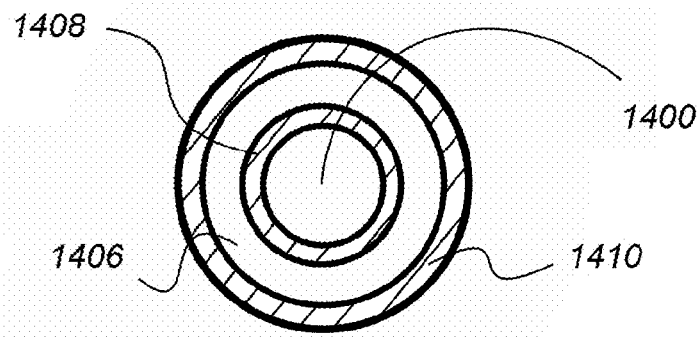
Figure 14D:
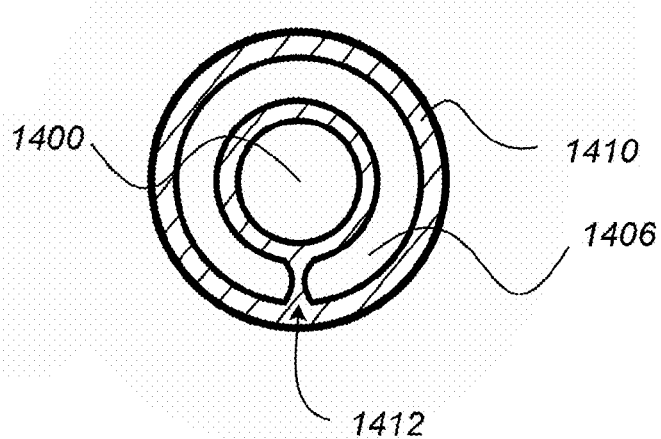
Figure 14E:
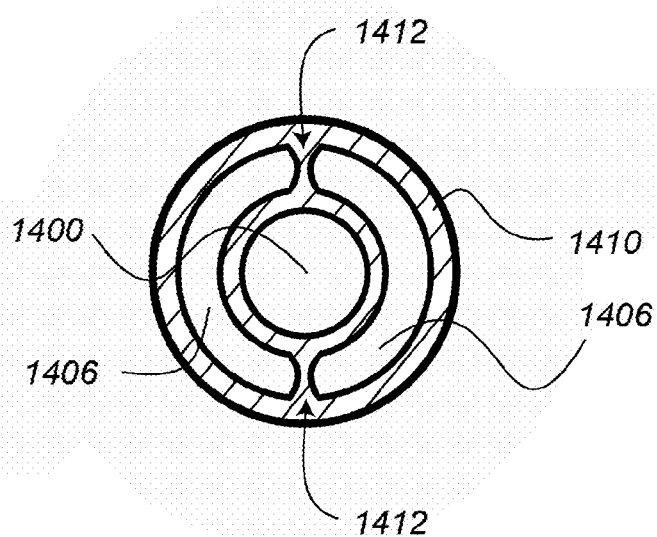

In the preferred embodiment for a double lumen balloon microcatheter FIGS. 14A-B, there are separate coaxial lumens FIG. 14C-E. The lumen for the inflating solution 1406 (herein referred to as "inflating lumen") in the embodiment shown is narrower than the lumen for the pushwire 1400. In the embodiment depicted in FIG. 14A-B, the diameter of the inner lumen is 0.018", the inner 1408 and outer 1410 walls are 85 µm thick, and the gap between the two walls is 50 µm. These dimensions are examples and may vary.

The outer diameter of the outer wall 1410 is preferred to be 0.035" but may vary from 0.021" to 0.050". Inflating holes 1402 in the outer wall 1410 of the microcatheter connect the lumen used for the inflating solution 500 to the balloon 1404. Rigidity in the longitudinal direction is important to avoid wrinkling (a unequal longitudinal translation between the two lumens, which may create a wavy surface). Therefore, there is a connection FIG. 14D 1412 between the two lumens. In other embodiments, the two lumens are largely free-floating FIG. 14C. They may be connected at the proximal and distal ends and/or connected intermittently (e.g. having a connection 1412 of length 2 mm repeatedly positioned once every 5 cm).

The intermittent connections serve to prevent wrinkling while minimizing rigidity. The intermittent connections need not be arranged in a parallel line with respect to the central axis. To have even rigidity in all directions the intermittent connections may be distributed in various patterns (e.g. random, helical, every 120 degrees etc.)

The intermittent connections may create by first manufacturing two separate tubes and then using induction welding to attached the outer tube to the inner tube at various points. In this case, the outer tube may be slightly deformed (e.g. pushed inward) at the locations where induction welding has been used.

In other embodiments, there are three or more separate lumens FIG. 14E.

The preferred method for manufacturing the double lumen balloon catheter is extrusion.

The method of inflation of the balloon on a double lumen catheter, manually or by pump, is more straightforward than in the single lumen-sealing ring embodiment. A pressure transducer is connected to one of the ports connected to the proximal end of the inflating lumen. Saline solution—or another inflating fluid, which may contain contrast agent—is pushed through the inflating lumen. As a consequence, the pressure of the inflating fluid increases, inflating fluid goes through the inflating holes, and the balloon inflates. No locking is required, as with the ring design, to enable inflation. The method for operation and postconditioning is similar to that for the other balloons described, such as the single-lumen balloon with a sealing ring, except there is no sealing ring and therefore a step to lock the sealing ring would not be needed.

Methods of Using Double-Lumen Balloon Microcatheters

The steps for using assemblies with a double-lumen balloon microcatheter are substantially similar to those described for assemblies with a single-lumen balloon microcatheter and a pushwire-mounted sealing ring in FIG. 10 in accordance with some embodiments of the present invention. One exception is that there is no sealing ring to be engaged with the inner walls of the catheter, and the balloon remains near the location of a clot (either inflated or deflated) between multiple passes.

According to some embodiments, methods of using an assembly with a double-lumen balloon microcatheter may include, but is not limited to, the following steps: (1)

inserting and navigating a 6 French catheter from an insertion point (e.g., the femoral artery) to the neck; (2) inserting and navigating a guidewire to a position proximal but close to a clot; (3) inserting and navigating a 4 French double-lumen balloon catheter through the 6 French catheter and over the guidewire to a position proximal to the clot; (4) pumping saline solution into a lumen of the balloon catheter balloon so that the balloon expands against the blood vessels walls to creates a partial or complete occlusion; (5) navigating the guidewire to a position Navigate the guidewire further, to a position distal to the clot.

Place the microcatheter over the guidewire and advance it to a position distal to the clot. The microcatheter is not expected to advance past the distal tip of the guidewire.

Remove the guidewire and replace it with a pushwire bearing the capture member and sealing ring. The active region of the capture member should be advanced so as to be adjacent to the clot. In other words, when unsheathed, the active region will expand and cover the entire length of the clot.

Unsheathe the capture member and wait, for example for five minutes, for the capture member to expand into the clot.

Inject a bolus of radiopaque solution through the 6 French catheter and assess the reperfusion status with angiography imaging. Perform only up to a certain maximum number of passes (e.g. 5 passes). If the maximum number of passes has been reached, then proceed to step 12 directly. [note: up to this point should be the same as for the umbrella]

If recanalization has occurred proceed to the next step—with postconditioning using the balloon on the double-lumen-catheter.

If recanalization has not occurred: removed pushwire and microcatheter from the body and go back to Step 2 and perform another pass.

The balloon may be inflated and deflated either by manually pumping inflating fluid in and out of the balloon or by using a pump to do it automatically. When fluid is pumped through the catheter and flows through the inflation holes and into the balloon, the balloon expands into the vessel blocking a greater portion of the vessel's lumen. When the balloon is filled sufficiently, it touches the inner lumen of the vessel and creates a complete occlusion. The balloon is flexible so that it will conform to the blood vessel's walls. As inflating fluid is removed from the microcatheter, the balloon empties, gradually resuming its former shape as flush with the microcatheter. Upon deflation, the occlusion is gradually removed and flow restored.

Pull the capture member (and microcatheter simultaneously) into the double-lumen-catheter and out of the body. Note that the capture member is not resheathed during its exit from the body. Optional: suction through the 6 French catheter and/or double-lumen-catheter can be used to limit the dispersion of secondary emboli.

If the maximum number of passes has NOT been reached, then proceed with step 13.

If the maximum number of passes has been reached, then proceed with step 10.

Insert the guidewire through the 6 French catheter and navigate the guidewire to a position proximal and close to the clot.

Intermediate Double-Lumen Balloon Catheters

Figure 15A:
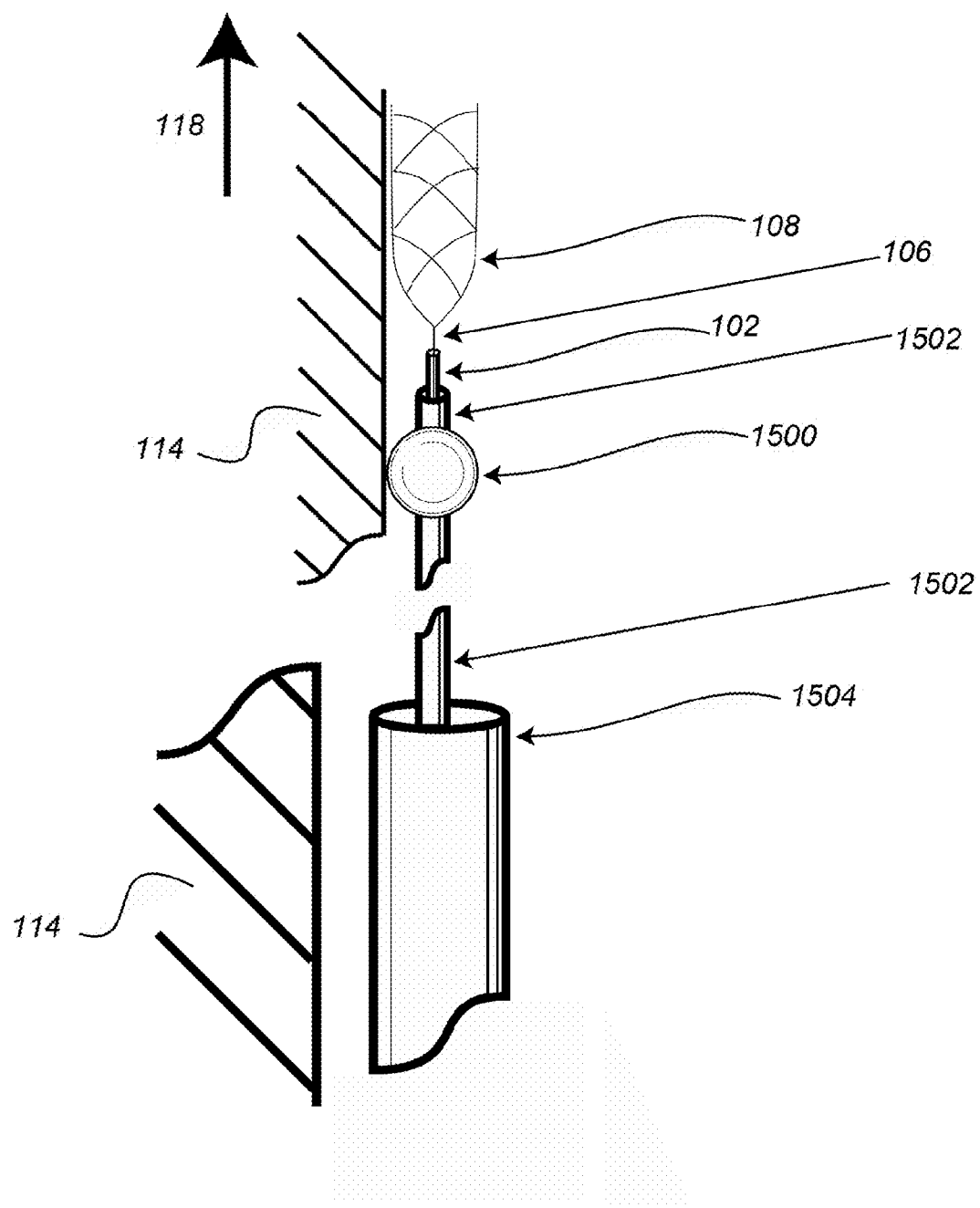
FIGS. 15A-15B illustrate an intermediate double-lumen balloon catheter in accordance with some embodiments of the present invention.
Figure 15B:
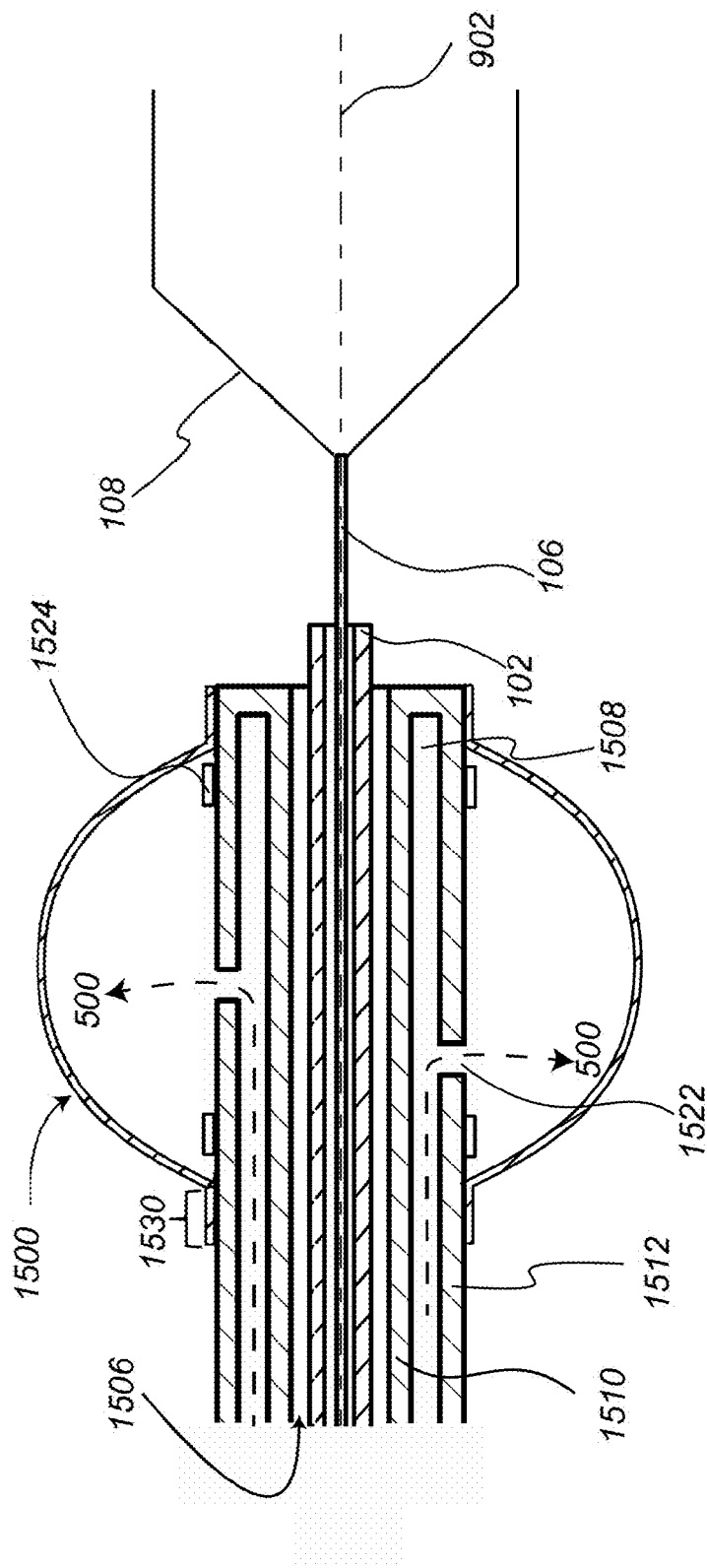

An additional way of using a balloon for postconditioning is to use an additional catheter FIG. 15A-B 1502 disposed between the microcatheter 102 and the large catheter (e.g. size 6 French guide catheter) 1504. This additional catheter 1502 may be a double lumen balloon catheter (herein referred to as "intermediate double lumen catheter"), and may be of size 5 French. The intermediate double lumen catheter may be any number of sizes, but is likely to range from 3 French to 5.5 French. The intermediate double lumen catheter depicted in FIG. 15 bears balloon 1500. The balloon is attached to the microcatheter in the attachment region 1530 on either side of the inflating membrane and is delineated by radiopaque markers 1524. However, intermediate single lumen catheters, which may or may not have a balloon, may also be used. Flexibility is an important characteristic for this intermediate double lumen catheter, to allow it to pass through the torturous curves of cerebral vessels. Reperfusion would be performed in cycles by using an inflating solution. It would be controlled by a syringe or pump, similarly to the balloon described in other sections of this document.

The large catheter 1504 is able to advance up to the internal carotid artery at the distal portion of the neck. The intermediate double lumen catheter 1502 would enter smaller tortuous arteries, such as the MCA, to conduct postconditioning as close to the location of the clot as possible, using a balloon near the distal end of the intermediate catheter 1500.

The intermediate double lumen catheter 1502 would be within the intermediate double lumen catheter and deploy the pushwire 106 and capture member 108. The profile of the inner lumen 1506 will be constant i.e. constant inner diameter. Here, the inflating solution 500 would have its own dedicated lumen 1508 within the walls 1510 and 1512 of the intermediate double lumen catheter. The inflating solution would not come into contact with the pushwire 106 or capture member 108.

In the preferred embodiment for an intermediate double lumen catheter FIGS. 15A-B, there are separate coaxial lumens (similar to FIG. 12C). The lumen for the inflating solution 1508 (herein referred to as "inflating lumen") in the embodiment shown is narrower than the lumen for the microcatheter 1506. Connectors 1526 may attach the walls of the two lumens. In the embodiment depicted in FIG. 15A-B the diameter of the inner lumen 1506 is 0.026", the inner 1510 and outer 1512 walls are 100 μm thick, and the gap between the two walls is 100 μm. These dimensions are examples and may vary.

The outer diameter of the outer wall 1512 is preferred to be 0.050" but may vary, for example, from 0.040" to 0.070". Inflating holes 1522 through the outer wall 1512 of the intermediate double lumen catheter connect the lumen used for the inflating solution 1504 to the balloon 1506.

Other Multiple-Lumen Balloon Catheter Embodiments of a Flow Modulation Member

Figure 16:
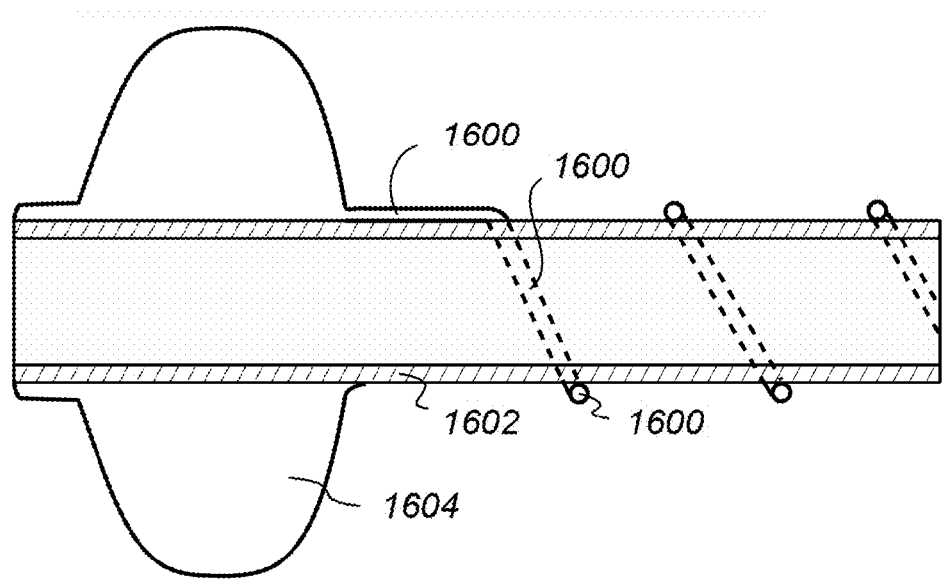
FIGS. 16-17 illustrate a balloon catheter with multiple lumina in accordance with some embodiments of the present invention.

In some balloon flow modulation systems, a conduit for balloon-inflating liquid (e.g. a saline solution) or gas is attached to the expandable balloon, and may be threaded through or alongside the microcatheter or incorporated into the walls of the microcatheter itself. According to some embodiments, a thinner and more flexible tube for the inflating-fluid runs along the outside of the microcatheter. The tube may run alongside the microcatheter according to a helical, straight, or other pattern, and the tube may either be unattached or attached (loosely, strongly, or just at points) to the microcatheter. FIG. 16 illustrates a balloon 1604 fed by an inflating-fluid tube 1600, which is wrapped around the outside of a microcatheter 1602 in a helical pattern.

Figure 17:
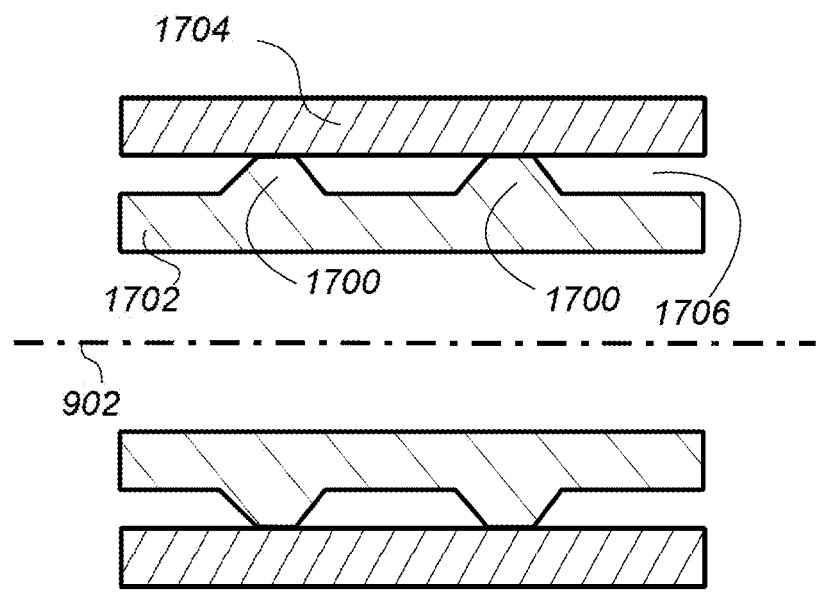

According to some embodiments, a conduit for the inflating-fluid is created as a hollow space within the walls of the microcatheter. The conduit may run inside the microcatheter walls according to a helical, straight, or other pattern. In preferred embodiments, a helical pattern—winding around the central longitudinal axis 902 of the microcatheter—is used for the conduit or any aspects that add to microcatheter rigidity (e.g., posts). FIG. 17 illustrates a microcatheter with a hollow space 1706 between its outer walls 1704 and its inner walls 1702, held open for the passage of inflating fluid by posts 1700. Posts may be of different widths. In certain embodiments, the posts are so wide that they connect to each other, and one continuous tubular or rectangular conduit winds between the inner and outer walls of the microcatheter in a helical pattern.

According to some embodiments, a separate microcatheter may carry the inflating fluid through its central lumen (without a guidewire inside). In these embodiments, the flow modulation balloon may be located anywhere in the blood vessel and may not be attached to the same microcatheter and guidewire that deliver a clot capture member.

The flow modulation member may be positioned in various locations relative to the microcatheter, guidewire, clot, and clot capture member. According to some embodiments, a balloon may be deployed (i.e., inflated) from or attached to a point proximal to the distal end of the microcatheter, the distal end of the microcatheter, on the guidewire proximal to the clot capture member, the distal end of the clot capture member, or the distal end of the guidewire. Unlike other embodiments of the flow modulation member, a balloon does not need to be re-sheathed, just deflated. Because the distal end of the microcatheter is not needed for re-sheathing, the flow modulation balloon may be deployed either proximally or distally to the clot. If the balloon is positioned on an extension of the clot capture member or the guidewire, distal to the clot, the balloon could also prevent the clot or emboli from being left behind or traveling to another vascular site when a clot capture member is pulled out of the body.

Catheter-Constrained Embodiments of a Flow Modulation Member

The flow modulation member may be self-expanding and attached to the pushwire proximal to the capture member. In these embodiments, the flow modulation member is deployed by translating the microcatheter so as to unsheathe the flow modulation member. To create cycles, flow is restored by resheathing the flow modulating member with the microcatheter.

Figure 18A:
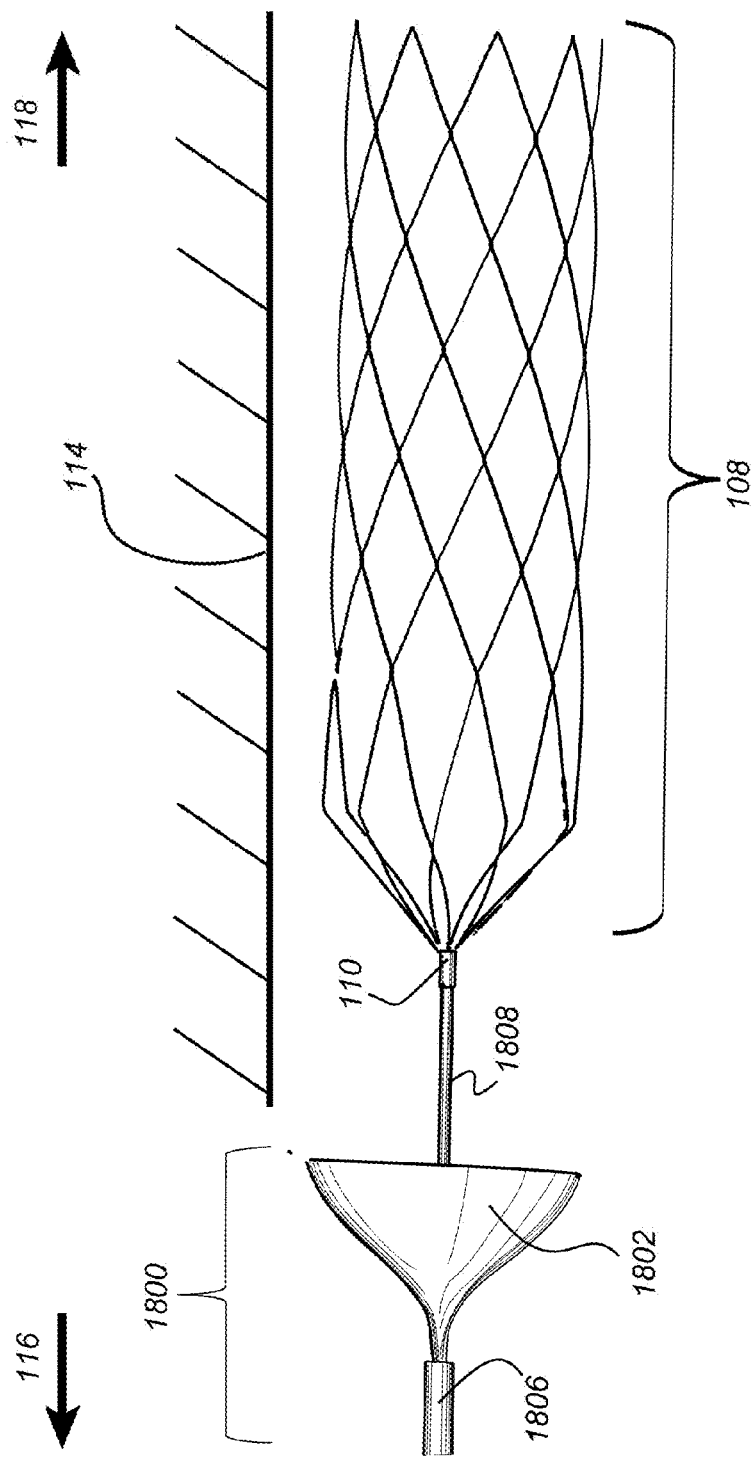
FIGS. 18A-18C illustrates an umbrella-like flow modulation member in accordance with some embodiments of the present invention.
Figure 18B:
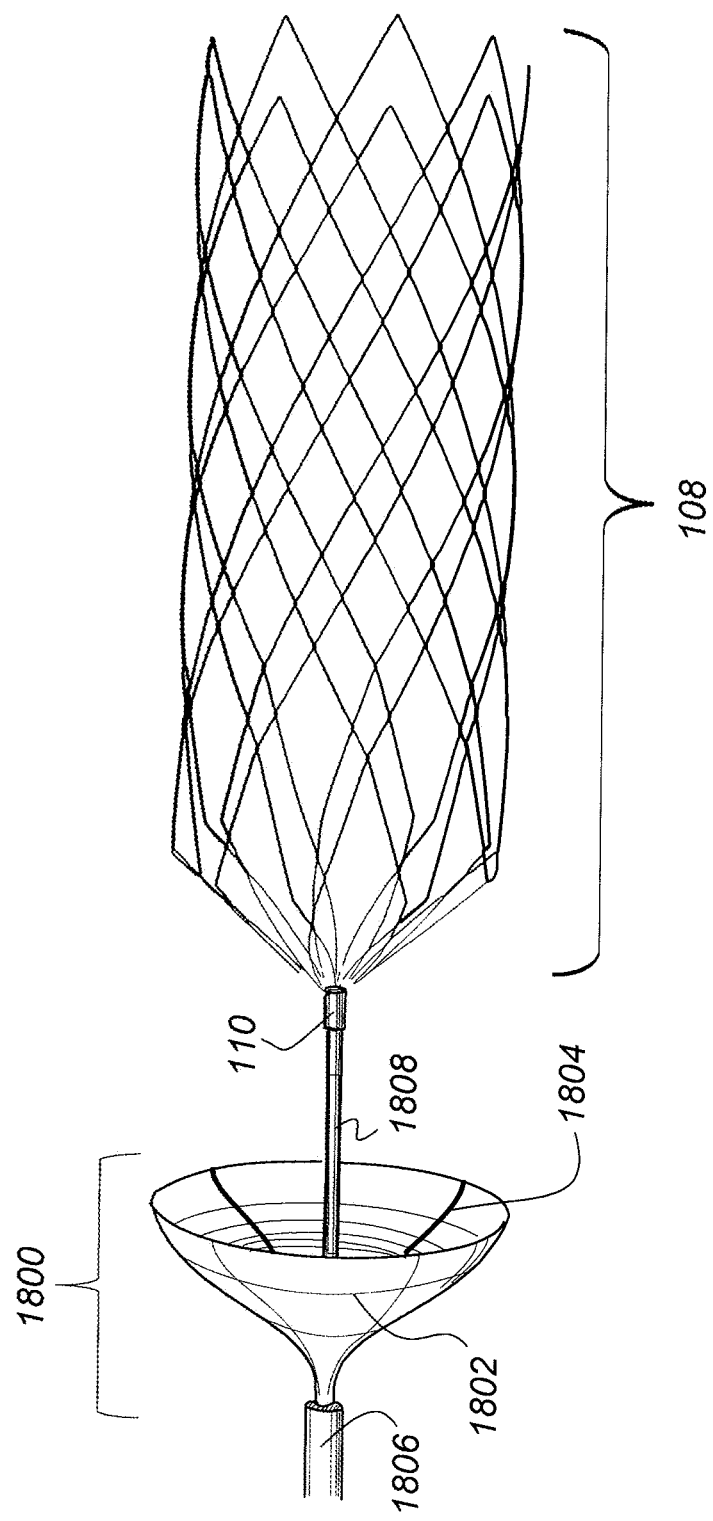
Figure 18C:
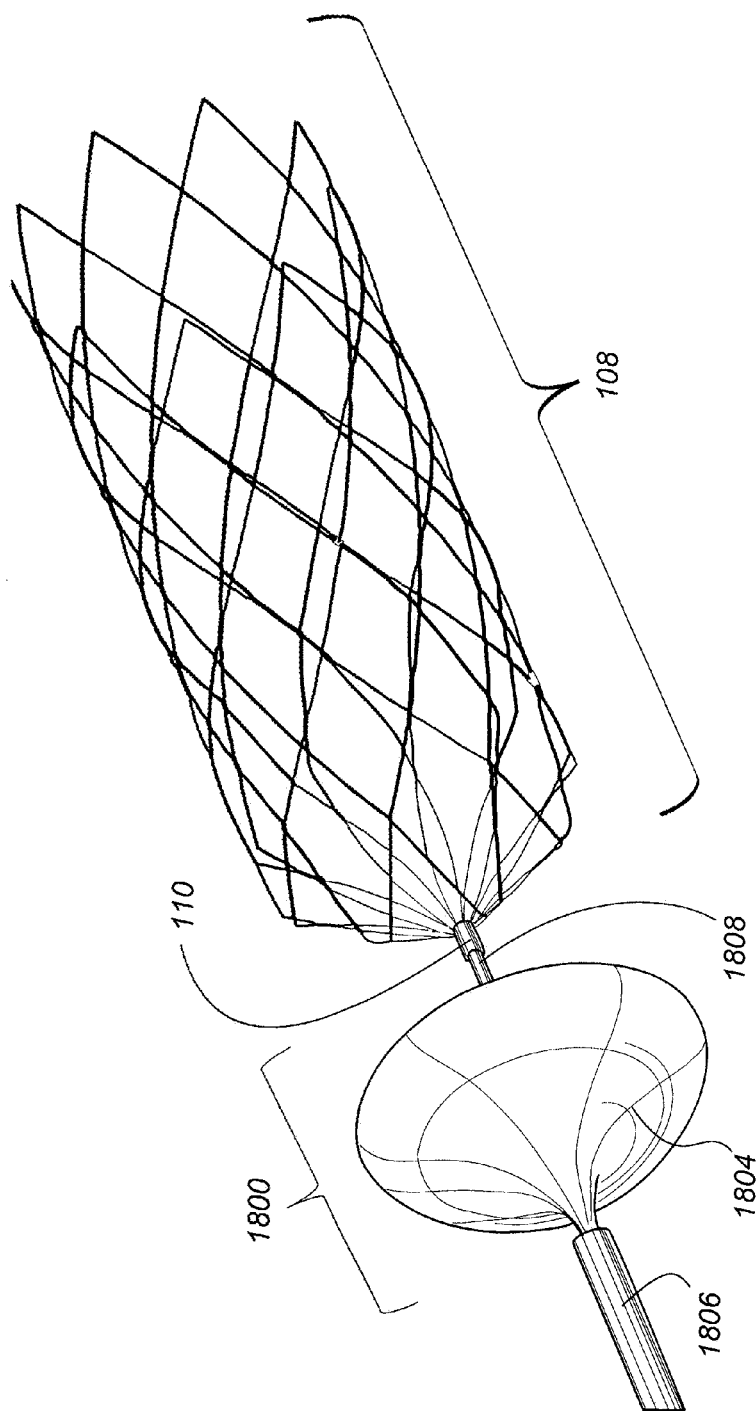

According to some embodiments, the flow modulation member features an umbrella-like shape. FIGS. 18A-C illustrates an embodiment of an umbrella-like flow modulation member 1800 in a fully expanded state with views from three different angles. The microcatheter 1806 has been translated proximally along the pushwire 1808 to release the flow modulation member 1800. The proximal portion of the flow modulation member 1800 exits the distal end of the microcatheter 1806 while the distal portion of the flow modulation member 1800 contacts the luminal walls 114 of the blood vessel to occlude blood flow from the proximal direction 116. The flow modulation member 1800 has struts 1804 to support a blood-flow-occluding membrane 1802. A simplified version of a clot capture member 108 is attached to the pushwire 1808 distal to the flow modulation member 1800.

In the embodiment shown in FIGS. 18A-C, the flow modulation member 1808 is designed with a strut length of 1.4 mm for blood vessels with a radius of 1 mm, and is positioned with the location of its proximal strut ends 10 mm proximal to the base of the clot capture member. Generally, the distance between the location of a flow modulation member's proximal strut ends and the base of a clot capture member may range anywhere from several centimeters to none (e.g., overlapping).

Frames and Struts

Figure 19:
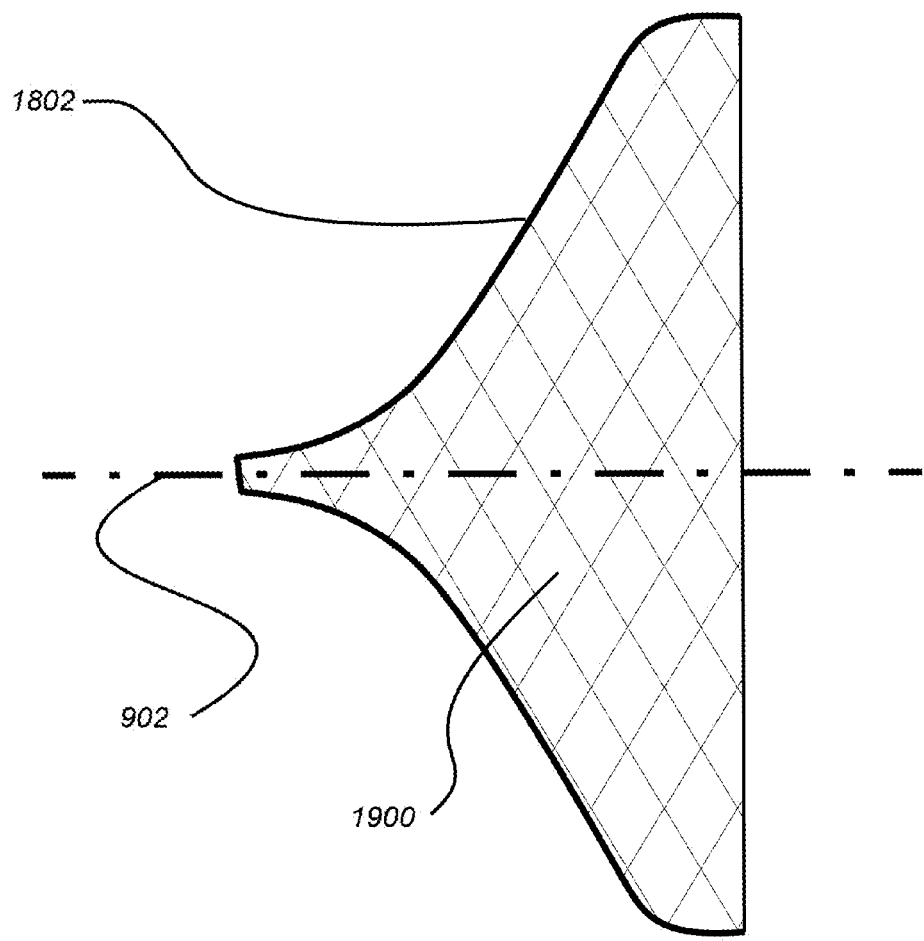
FIG. 19 illustrates an umbrella-like flow modulation member having primary struts encased within a membrane in accordance with some embodiments of the present invention.

In accordance with certain embodiments, one or more struts form the frame of the flow modulation member. In an umbrella-like flow modulation member, struts generally exert a force to expand latitudinally and may spread the occlusion membrane across the blood vessel aperture. Structures, geometries, patterns, and numbers of struts in a flow modulation member may be varied to achieve a desired force of expansion, flexibility, and ease of re-sheathing. To optimize the opening and closing trajectory, force against the blood vessel wall, resistance against blood flow, and degree of occlusion, the flow modulation member may have a different number of primary struts, secondary struts, and non-linear geometries. FIG. 19 illustrates an embodiment of an umbrella-like flow modulation member expanded latitudinally from the central longitudinal axis 902 with an occlusion membrane 1802 supported by a lattice pattern of struts 1900. However, the density of lattice pattern of struts 1900 may hinder the ease of re-sheathing the flow modulation member.

Figure 20:
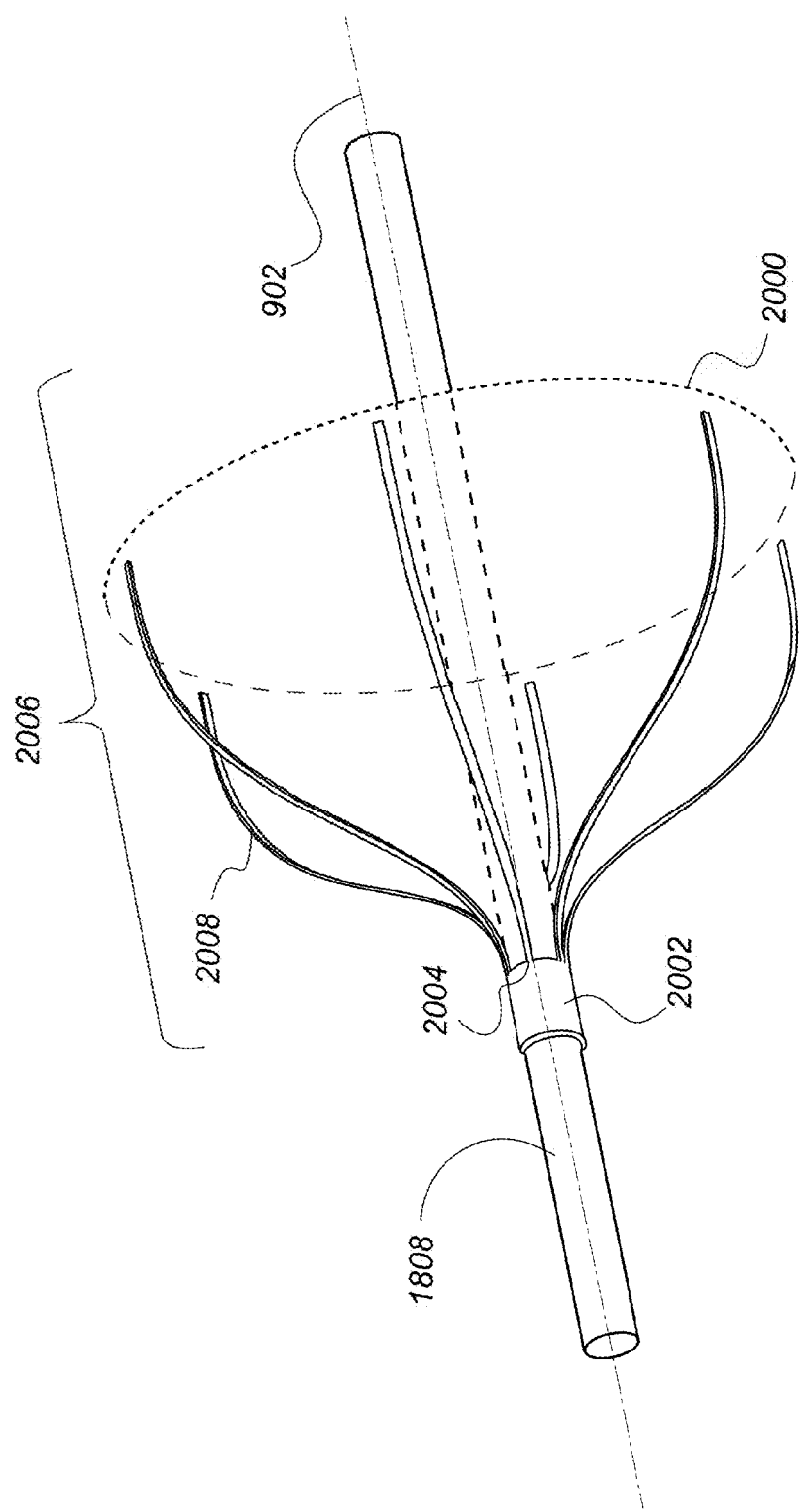
FIGS. 20-21 illustrate an umbrella-like flow modulation member, with its primary struts encased within a membrane, from a cross-sectional view perpendicular to the central longitudinal axis in accordance with some embodiments of the present invention.
Figure 21:
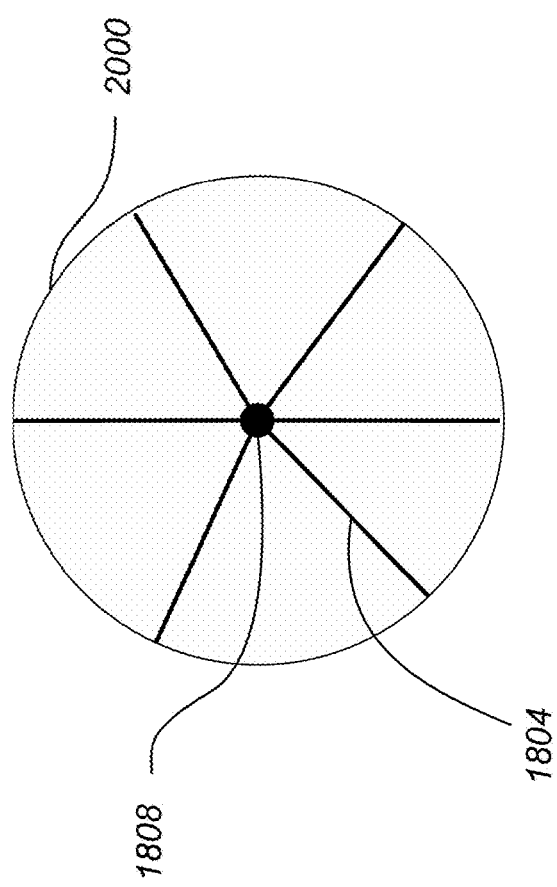

According to a preferred embodiment, FIGS. 20 and 21 illustrate two views of an umbrella-like flow modulation member 2006 with six primary longitudinal struts 2008. Although six primary struts are preferred, a smaller or larger number of primary struts may be used generally. In FIG. 20, the primary struts 2008 span the substantial length of the flow modulation member 2006, attaching at their proximal ends to a pushwire 1808 at connection 2004 to ring 2002, and running parallel to a plane of the central longitudinal axis 902 while expanding latitudinally. However, the edge of an occlusion membrane 2000 may extend past the distal ends of the primary struts 2008. As shown in FIG. 21, the outer circle is simply the distal edge of the occlusion membrane 2000.

In accordance with some embodiments, the form and curvature of the self-expanding primary struts must be sufficient to reach the targeted blood vessel wall with sufficient spring force to block blood flow when unsheathed from the microcatheter. FIGS. 22A-D illustrate four exemplary embodiments of primary strut curvature when the strut is in its natural expanded state from a view parallel to the central longitudinal axis. For each embodiment, a strut 1804 is shown between the central longitudinal axis 902 where it connects to pushwire 1806 and contacts the blood vessel wall 114.

Figure 22A:
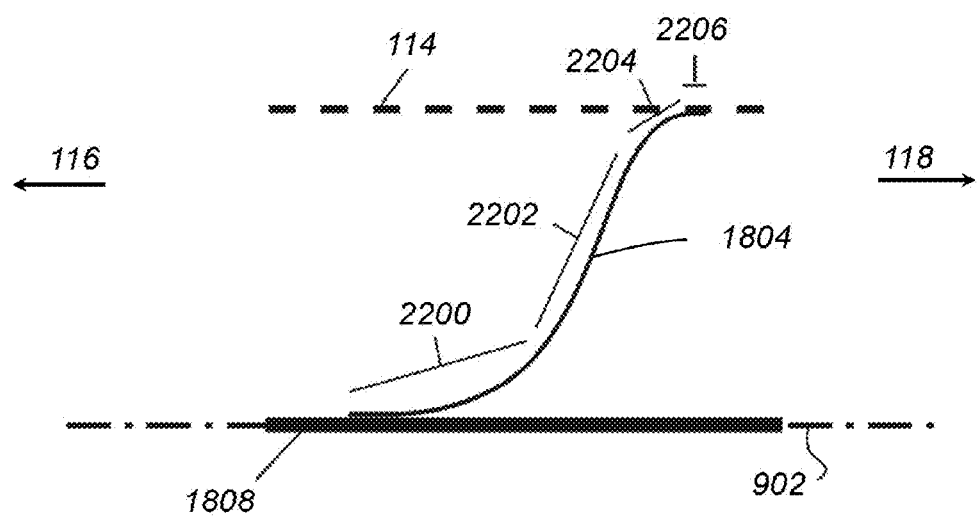
FIGS. 22A-22D illustrate strut curvatures of an umbrella-like flow modulation member in accordance with some embodiments of the present invention.

In the preferred embodiment of FIG. 22A, a first section 2200 of the strut 1804 curves with increasing slope away from the central axis 902, convex to the flow of blood. A second section 2202 of the strut 1804 is substantially straight and extends from the first curved section 2200. A third section 2204 of the strut 1804 continues from the second section 2202, concave to the flow of blood with decreasing slope relative to the central axis 902. A fourth section 2206 of the strut 1804 is substantially parallel to the central axis 902 and extends the third section 2204 until the strut is flush with the blood vessel wall 114. The fourth section 2206 increases the area of contact between the strut and the blood vessel wall, which further stabilizes the flow modulation member, thus strengthening its blood-flow-blocking capabilities by increasing the amount of force it can apply without damaging the blood vessel and surrounding brain tissue. Thus, the fourth section 2206 may allow an operator to perform postconditioning with greater speed and effectiveness.

Another advantage of the primary strut curvature shown in FIG. 22A is that the small slope of the first section 2200 (relative to the central longitudinal axis 902) provides finer control of the aperture of the flow modulation member because movement of the umbrella-like flow modulation member in and out of the microcatheter along the first section 2200 of the struts translates into a smaller difference in the area of the luminal latitudinal plane blocked by the member than if the same movement is made along the second section 2202.

Figure 22B:
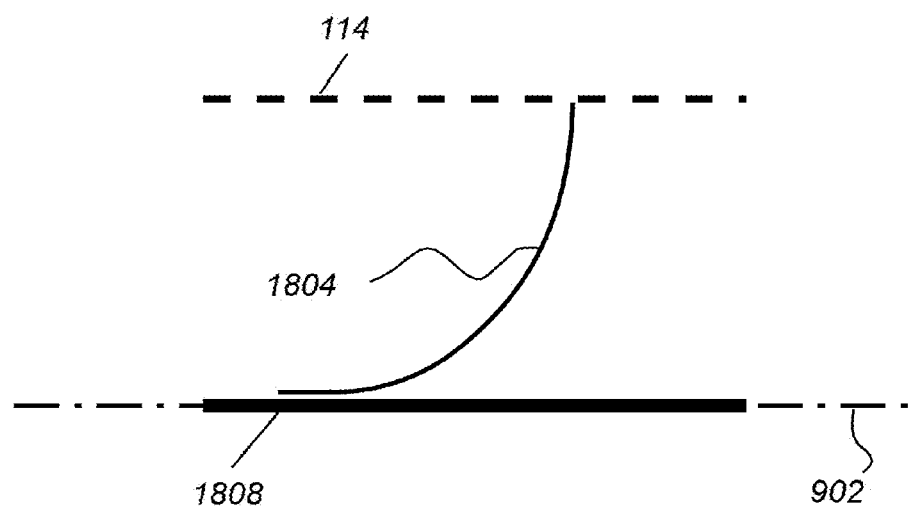
Figure 22C:
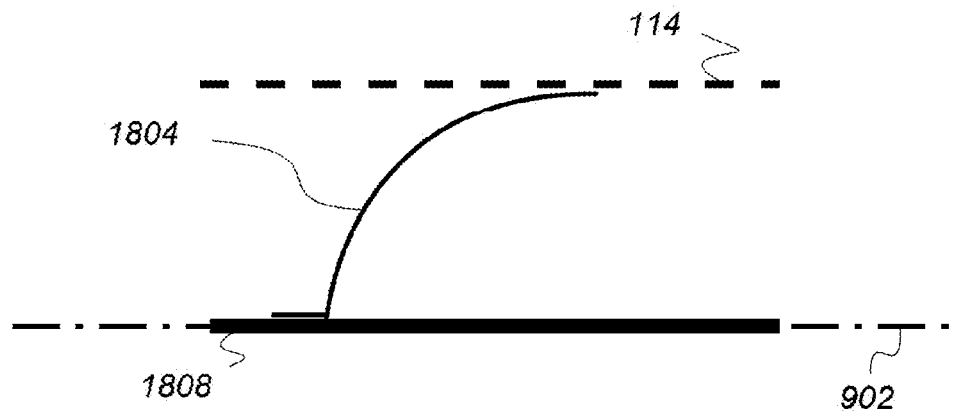
Figure 22D:
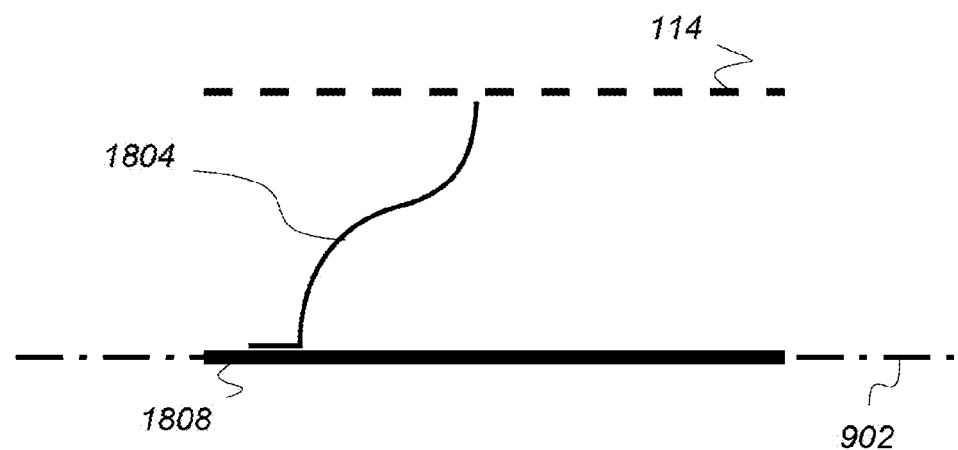

Other primary strut curvatures are contemplated. Generally, a convex umbrella surface is more stable than a concave umbrella surface because blood flow pushing against a concave configuration has a greater propensity to collapse the umbrella. Embodiments of a flow modulation member with convex umbrellas surfaces tend to exert more radial force against the blood vessel wall as blood flows against them, therefore creating a tighter seal. For example, FIG. 22B illustrates a strut 1804 with one curved section of continuously increasing slope away from the central axis 902, convex to the flow of blood for greater stability. Meanwhile, FIG. 22C illustrates a strut 1804 with one curved section of continuously decreasing slope away from the central axis 902, concave to the flow of blood, useful perhaps for milder occlusion. FIG. 22D illustrates a strut 1804 with two curved sections, the proximal section continuously increasing in slope and convex to the flow of blood, the second distal section continuously decreasing in slope and concave to the flow of blood.

In accordance with most embodiments, the potential radius of an umbrella-like flow modulation member at its distal end, should be substantially similar to, or greater than, the radius of the targeted blood vessel. When fully deployed, the distal end of the flow modulation member is compressed by the blood vessel walls. This compression allows the flow modulation member to exert an outward radial force on the vessel walls. Thus, different sizes of flow modulation members are necessary to achieve the desired outward radial force for different sizes of blood vessels. For example, the flow modulation member's distal radius may range from 1 mm to 4 mm in its deployed state.

FIGS. 23A-B illustrate the angle between the central longitudinal axis 902, which is parallel to pushwire 1808, and a line 2304, or 2306 respectively, from the proximal junction to the distal end of a primary strut of a flow modulation member in, respectively, working state and resting state. The change in the angle results a residual outward radial force on the blood vessel walls 114. During working state, when the umbrella of the flow modulation member is constrained by blood vessel walls 114 at distal radius 2310, this angle is referred to as the working angle 2300. During resting state, when the umbrella of the flow modulation member is deployed but not constrained by blood vessel walls 114 at distal radius 2312, this angle is referred to as the set angle 2302. In most embodiments, the set angle is greater than the working angle. For example, the set angle 2302 in FIG. 23B may be 60 degrees, while the working angle 2300 in FIG. 23A may be 45 degrees. The appropriate umbrella length for a given blood vessel radius may be calculated from the set and working angles. Thus, the working angle 2300 and set angle 2302 may be used to determine the appropriate longitudinal extension in the working state 2308 and resting state 2314 of the umbrella along the central axis 902.

The extent of the latitudinal expansion of a flow modulation member for a given translation of a microcatheter is another consideration when determining the slope(s) and/or length(s) of the primary struts. In certain embodiments, a rapid expansion of an umbrella-like flow modulation member with minimal translation of the microcatheter may be desirable. In other embodiments, a more gradual expansion may afford greater control. The optimal rate of flow modulation member deployment, such as umbrella expansion, per pushwire translation may be varied depending on the procedure and status of the clot.

According to some embodiments, the resistance of a flow modulation member against blood flow and its outward radial force against the blood vessel wall varies at different points of its profile.

In some embodiments, a flow modulation member is designed so that the radial force changes over the course of the member's deployment, to minimize friction between the member and the blood vessel wall. For example, in certain embodiments, the radial force of an umbrella-like flow modulation member may decrease as the radius of the partially deployed umbrella approaches that of the blood vessel. In alternative embodiments, a fully expanded flow modulation member may not completely contact the blood vessel wall. According to some embodiments, an operator may choose not to deploy the flow modulation member to its full extent. In cases where a flow modulation member does not contact or loosely contacts the blood vessel wall, only partial occlusion may be achieved and some blood may flow around the member.

In accordance with certain embodiments, the cross-sections of the self-expanding struts may take various shapes and dimensions in order to reach the targeted blood vessel wall with sufficient spring force to block blood flow. FIGS. 24A-E illustrate five exemplary embodiments of primary strut cross-sections, including the depth 2400 and the width 2402. The depth 2400 of a strut is substantially parallel to a radial line 2404 from the central longitudinal axis 902 (along which the pushwire 1808 travels) to the blood vessel wall 114.

Figures 24A, 24B, 24C, 24D, 24E:
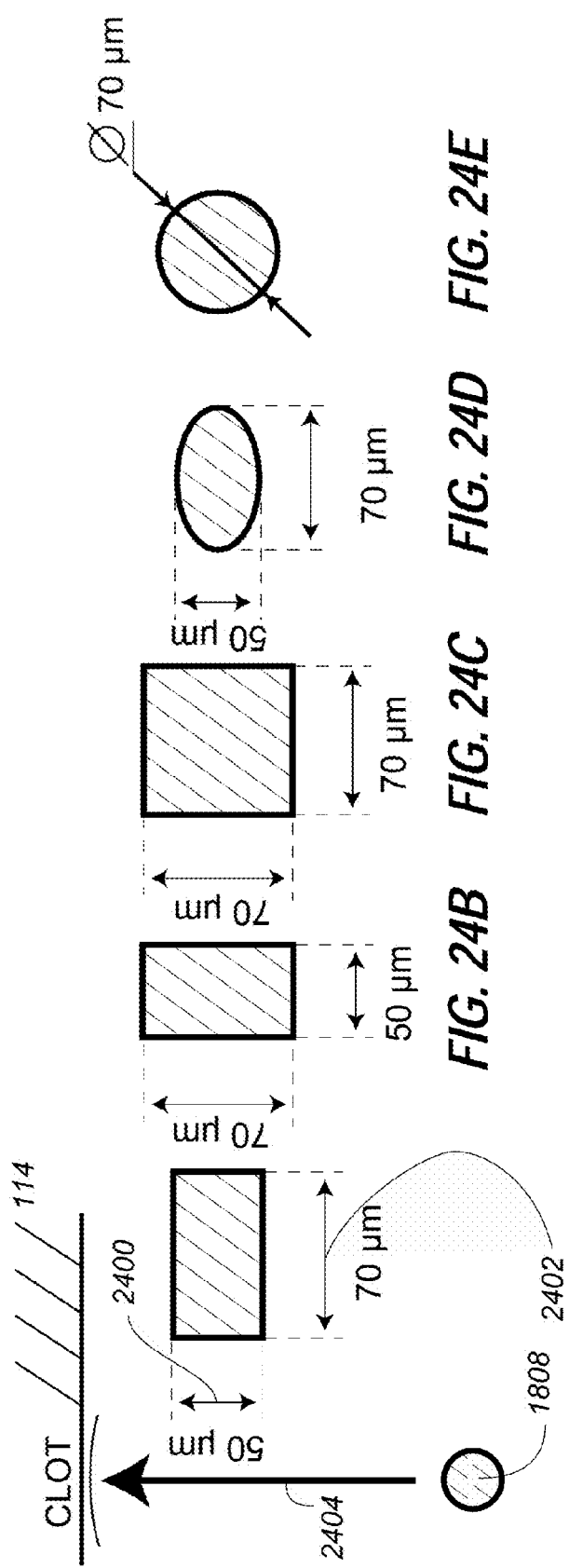
FIGS. 24A-24E are cross-sectional views of alternative primary strut designs for an umbrella-like flow modulation member in accordance with some embodiments of the present invention.

In the preferred embodiment of FIG. 24A, a rectangular cross-section of a strut is shown with a greater width 802 (70 µm) than depth 800 (50 µm), in order to increase the strut's ability to support an occlusion membrane. However, a greater depth 2400 may increase the ability of the struts to exert radial force. Therefore, a greater depth may be desired, as shown in FIG. 24B, where a rectangular cross-section of a strut is shown with a greater depth 2400 (70 µm) than width 2402 (50 µm). The square cross-section of a strut shown in FIG. 24C, with depth 2400 (70 µm) and width 2402 (70 µm), may be selected for both support and greater radial force. Generally, a square or rectangular cross-sectional shape may be easier to manufacture if cutting a strut from sheets, cones, or cylinders. Also, a square or rectangular cross-sectional shape may eliminate the need for electro-polishing to smooth the edges of a strut.

Other strut cross-sectional shapes are contemplated. For example, FIG. 24D illustrates a strut with an oval cross-section, having a greatest depth 2400 (50 µm) and greatest width 2402 (70 µm). Meanwhile, FIG. 24E illustrates a strut with a circular cross-section, having constant diameter (70 µm). In some embodiments of an umbrella-like flow modulation member, the shape and dimensions of a strut cross-section may even change across the length of the strut to achieve varying pressures and other characteristics at different points of the umbrella.

In accordance with preferred embodiments, the struts are made from nitinol. However, other shape-memory materials, shape-memory alloys, or super-elastic materials that exert pressure to expand to their set shape may be used. Such materials include, for example, nickel titanium alloy, stainless steel, or cobalt chromium alloys.

Different manufacturing methods may be used for the different types of struts. Struts may be formed out of a single piece of material or made from different pieces and assembled together. A single piece of material is preferred, when readily manufacturable, because it simplifies the attachment process and may afford greater structural integrity. Laser cutting may be used to manufacture the struts. For example, the struts may be cut from a cone that has an envelope similar to the desired expanded shape of an umbrella-like flow modulation member and a thickness as close as possible to the depth desired for the strut cross sections. Alternatively, the struts may be cut from a flat sheet of material or from a sheet of material that has been bent to the desired curvature of the struts. A substantially flat sheet of material will generally result in struts with rectangular cross sections.

Electropolishing may or may not be needed, but may be used, in combination with the other methods described, to round the edges of individual struts to achieve oval or circular cross sections like those shown in FIGS. 24D and 24E respectively. In other embodiments, struts with oval or circular cross sections may be achieved by using thin wires. Likewise, bending and heat-setting may or may not be used, in combination with the other methods described, to form and perfect the curvature of the struts.

Figure 25D:
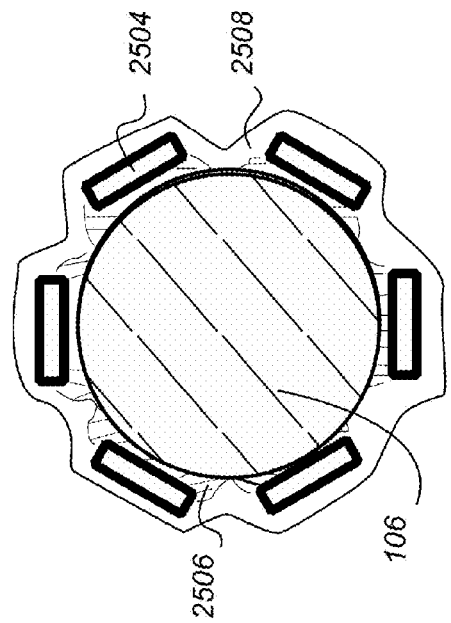
FIGS. 25A-25D illustrate an umbrella-like flow modulation member in accordance with some embodiments of the present invention.

In some embodiments, the primary struts of an umbrella-like flow modulation member may be cut from a single piece of material. The embodiment shown in FIG. 25A illustrate how this continuous piece has a ring-base 2502 at its proximal end. This ring-base 2501 is placed over and attached to the pushwire 106. According to some embodiments, a ring-base is attached to the pushwire via thermal interference fitting. To use thermal interference fitting, the ring-base is made initially with a diameter too small to fit over the pushwire. When heated, the ring-base expands so it can be placed over the pushwire. As it cools, the ring-base tightens around the pushwire to create a firm attachment. Alternatively, the pushwire may be cooled to a low temperature such that the pushwire's diameter decreases. In this case, the ring-base would be manufactured at its final diameter. The ring-base is placed onto the cooled pushwire. As the pushwire expands to its normal diameter (at room temperature), it creates a firm attachment with the ring-base.

Figure 25B:
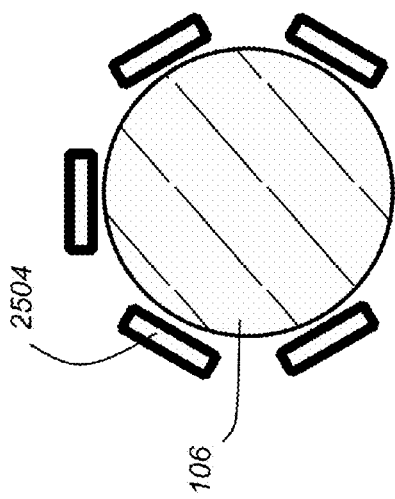
Figure 25C:
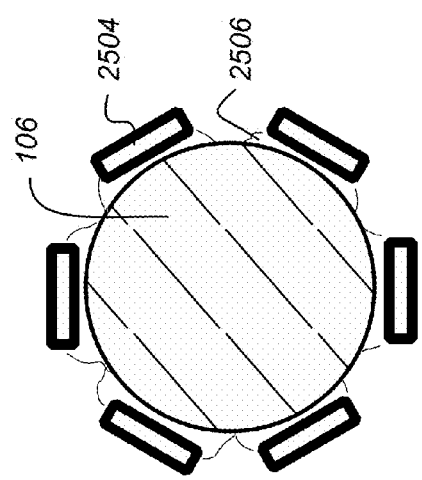
Figure 25A:
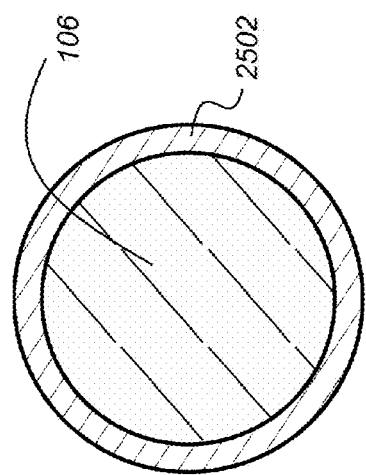

If the primary struts are made from separate parts, as shown in FIG. 25B, the proximal ends of the struts 2504 must be securely attached to the pushwire 106. The struts 2504 may be attached in any number of ways including but not limited to: welding the struts directly to the pushwire, soldering the struts directly to the pushwire (using, for example, platinum solder), or attaching the struts to a metal or plastic ring, which is either first or subsequently attached to the pushwire. The embodiment shown in FIG. 25C illustrates how the struts 2504 are attached to the pushwire 106 with solder 2506.

In further embodiments, a sleeve or a low-profile ring may be placed on top of the various attachment junctions to promote smooth deployment and retrieval and to relieve strain on the attachments. FIG. 25D illustrates how a sleeve 2508 may be attached to the pushwire 106 with solder 2506 to cover the proximal ends of struts 2504. A sleeve may be made of a heat-shrinkable material such as polyethylene terephthalate, nylon, or another polymer or elastic material. Adhesive, molding, press-fitting, interference fitting, curing, epoxy, or other attachment methods or combinations thereof may also be used to attach a sleeve.

Figure 26:
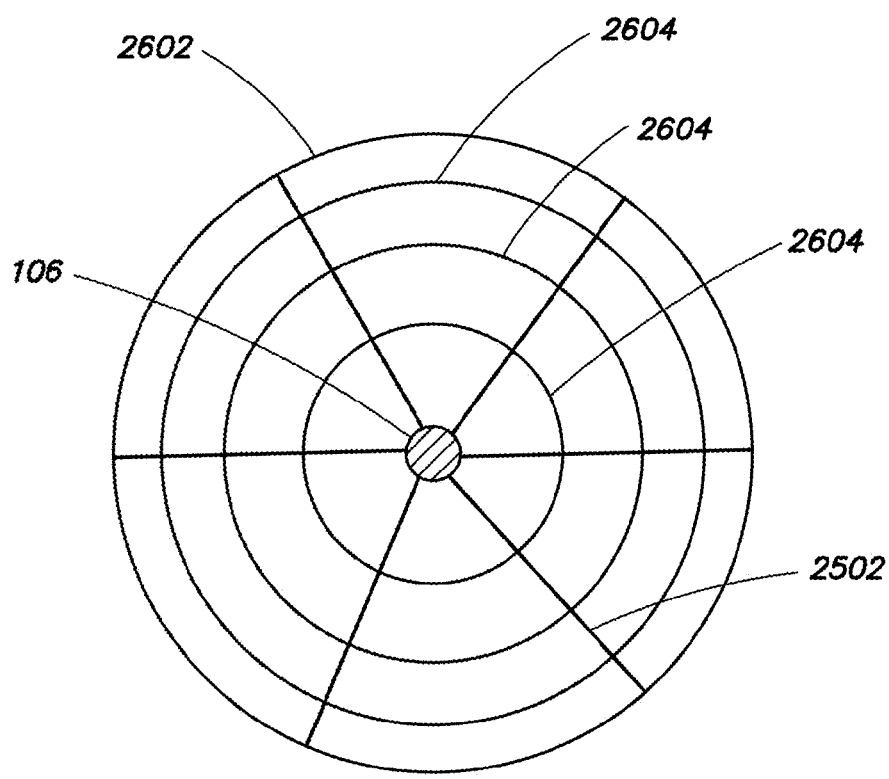
FIGS. 26-28 illustrate various strut and membrane designs for an umbrella-like flow modulation member in accordance with some embodiments of the present invention.
Figure 27:
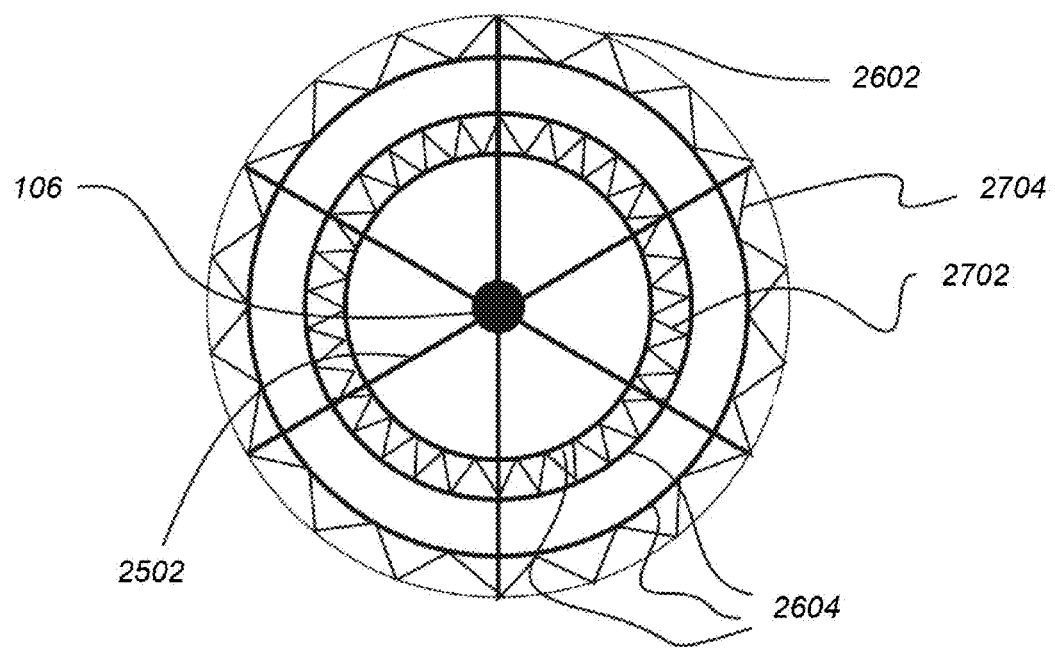

According to some embodiments, a flow modulation member may incorporate secondary struts. The objectives of using secondary struts may include increasing pressure against blood flow at desired areas of the member, supporting a membrane of the member, and providing a closer fit between the member and blood vessel walls. For example, latitudinal struts around the distal end of an umbrella-like flow modulation member and/or latitudinal struts around the mid-section of the member may be effective. The outer circle 2602 of the embodiment in FIGS. 26-27 may represent the distal edge of a membrane, a secondary latitudinal strut, or both.

Figure 28:
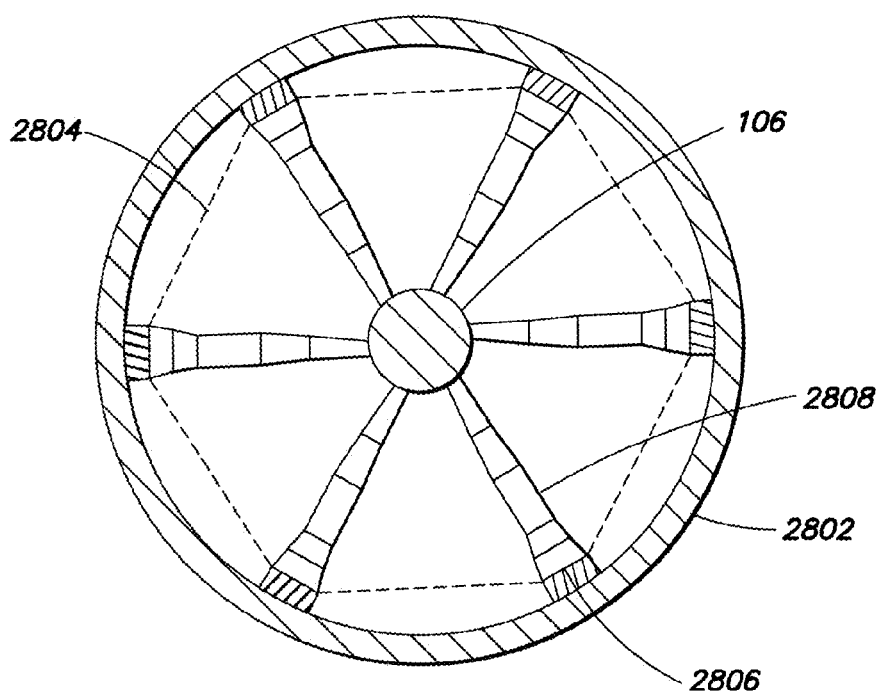

Distal secondary struts may advantageously facilitate contact between the distal open end of an umbrella-like flow modulation member and the luminal blood vessel wall by creating a more perfectly circular shape, instead of straight edges of membrane between the primary struts, thus better conforming the distal end of the member to the latitudinal plane of the vessel wall. This is illustrated, for example, in FIG. 28 by the distal latitudinal strut 2802, instead of straight membrane edges 2804. In addition to more firmly engaging the blood vessel wall, secondary struts may minimize trauma to the blood vessel walls by improving the distribution of radial force.

Latitudinal struts may be added to the mid-section of an umbrella-like flow modulation member in order to further stabilize the member, make the mid-section of the umbrella more rigid, and/or exert pressure at various points against blood flow. The embodiments in FIGS. 26 and 27 also feature latitudinal struts 2604 (and potentially 2602) around the mid-section of the member.

Figure 29A:
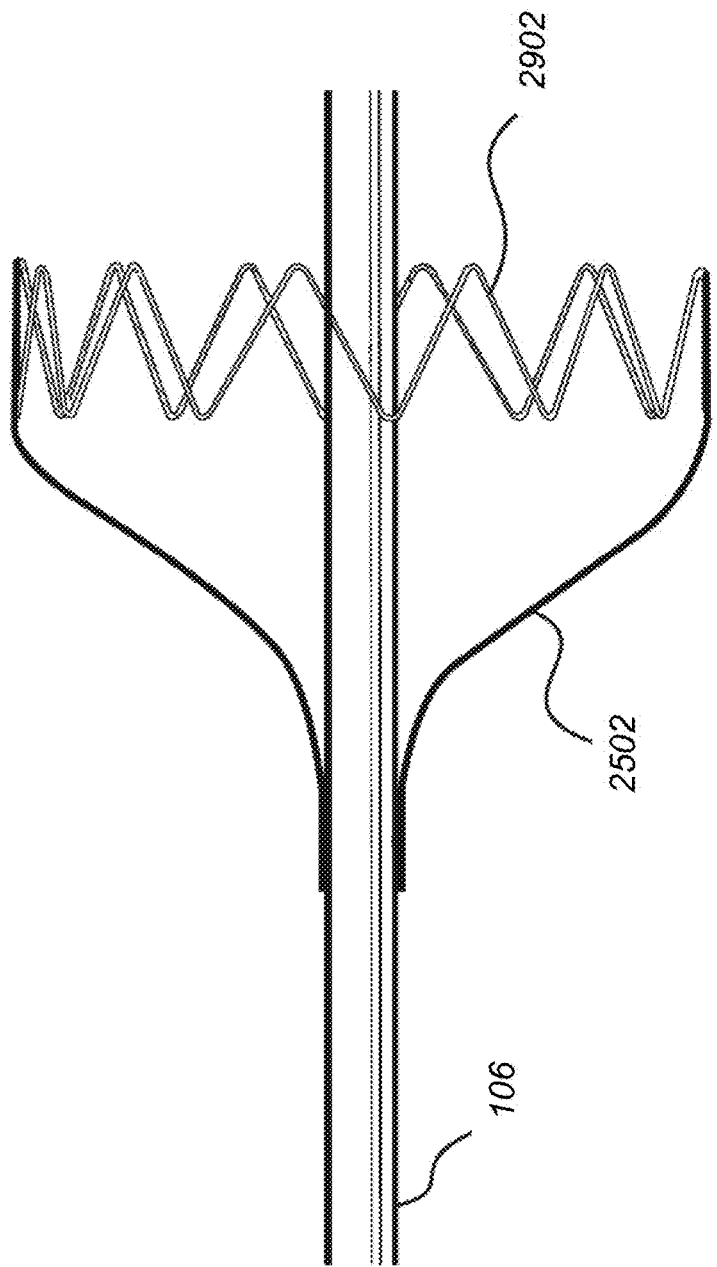
FIGS. 29A-29B illustrate an umbrella-like flow modulation member with a latitudinal strut having a zigzag configuration in accordance with some embodiments of the present invention.
Figure 29B:
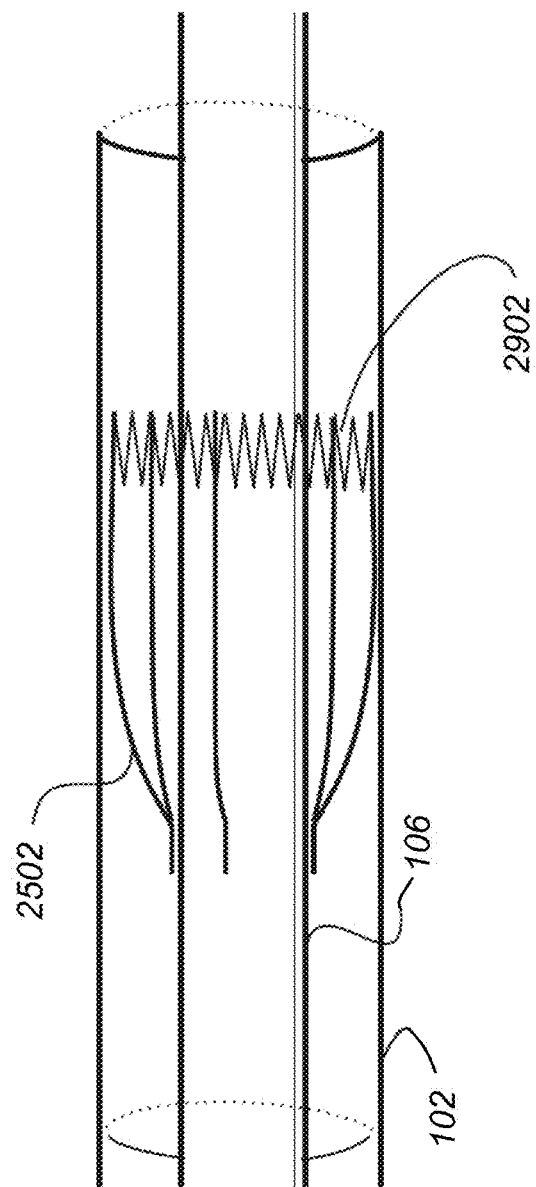

In preferred embodiments, a latitudinal strut is configured to include a series of straight sections and bends, referred to as a zigzag configuration. For example, the embodiments in FIGS. 29A and 29B feature a zigzag configuration for a latitudinal strut 2902 at the distal end of an umbrella-like flow modulation member. In addition to a zigzag-configured latitudinal strut 2704 at the distal end of an umbrella-like flow modulation member, the embodiment in FIG. 27 features a zigzag-configured latitudinal strut 2702 around the mid-section of the member. The zigzag configuration is useful because it exerts latitudinal force while, as shown in FIG. 29B, folding up easily to contract back into the microcatheter 102. Configurations other than zigzag may also be used for latitudinal struts.

In some embodiments, secondary struts include additional longitudinal struts that are not attached to the membrane of an umbrella-like flow modulation member. These stabilizing longitudinal struts may contact the blood vessel wall during deployment in order to center and further support the member. In certain embodiments, secondary struts include longitudinal struts that may pass through the hollow center of an umbrella-like flow modulation member, perhaps crossing the central axis 200.

According to some embodiments, secondary struts may be formed using the same materials with the same processes as primary struts. However, a secondary strut may have differently-shaped cross-section (e.g., a near-round cross-section) with a smaller diameter (e.g., 50 μm) than the primary struts. Secondary struts may be attached to primary struts via methods including welding, soldering, or adhesion. However, in preferred embodiments, when efficient, the primary and secondary struts are cut from the same piece of original material.

In some embodiments, radiopaque materials may be attached to or used to make or coat a portion or all of the struts (or strut attachments, e.g., solder) of a flow modulation member. The radiopaque material or materials may include: platinum, cobalt, molybdenum, silver, tungsten, iridium, polymers, or various combinations. In preferred embodiments, three of the longitudinal struts are made from or coated with a radiopaque material. The marked struts may be equidistant from each other so that that state of expansion can be accurately observed from many angles. In a further preferred embodiment, a flow modulation member has platinum radiopaque markers welded to the distal ends of the primary struts. Alternatively, or in addition to marking the distal ends of the struts of a flow modulation member, radiopaque material may be used to mark the proximal ends of the struts, the pushwire at a point close to the base of the struts, the pushwire at points adjacent to where the open end of the flow modulation member touches when re-sheathed, and the distal end of the microcatheter.

Membranes

In accordance with some embodiments, the struts of an umbrella-like flow modulation member support a membrane, which blocks or slows the flow of blood when deployed in a vessel. In some embodiments, the membrane is flexible enough to allow the flow modulation member to pass through the brain's narrow and tortuous blood vessels. In preferred embodiments, the membrane is impermeable to blood and is elastic. To achieve these characteristics, the membrane of the umbrella may be constructed from various materials. Polypropylene is preferred but other materials may be used such as, thermoplastic polymers, elastomeric silicones, latexes, other polymers or a blend thereof. An example is ENGAGE® (Dow Chemical). Elasticity allows the membrane to expand and contract with the movement of the struts. However, in other embodiments, the membrane need not be elastic, instead simply bending or folding with the movement of the struts. In some embodiments, the membrane need not even be impermeable.

In additional to polymers, the membrane may be made from other materials that block or slow blood flow, including types of woven fabric mesh or a web of fabric (e.g., made from Dacron). The membrane, as well as other or all parts of a flow modulation member, may be coated with a non-stick substance to reduce friction and enable easy movement through and upon exit from the microcatheter. Suitable friction-reducing or lubricating substances may include, but are not limited to, silicone-based lubricating agents, and polytetrafluoroethylene or other polymer coatings.

Figure 30:
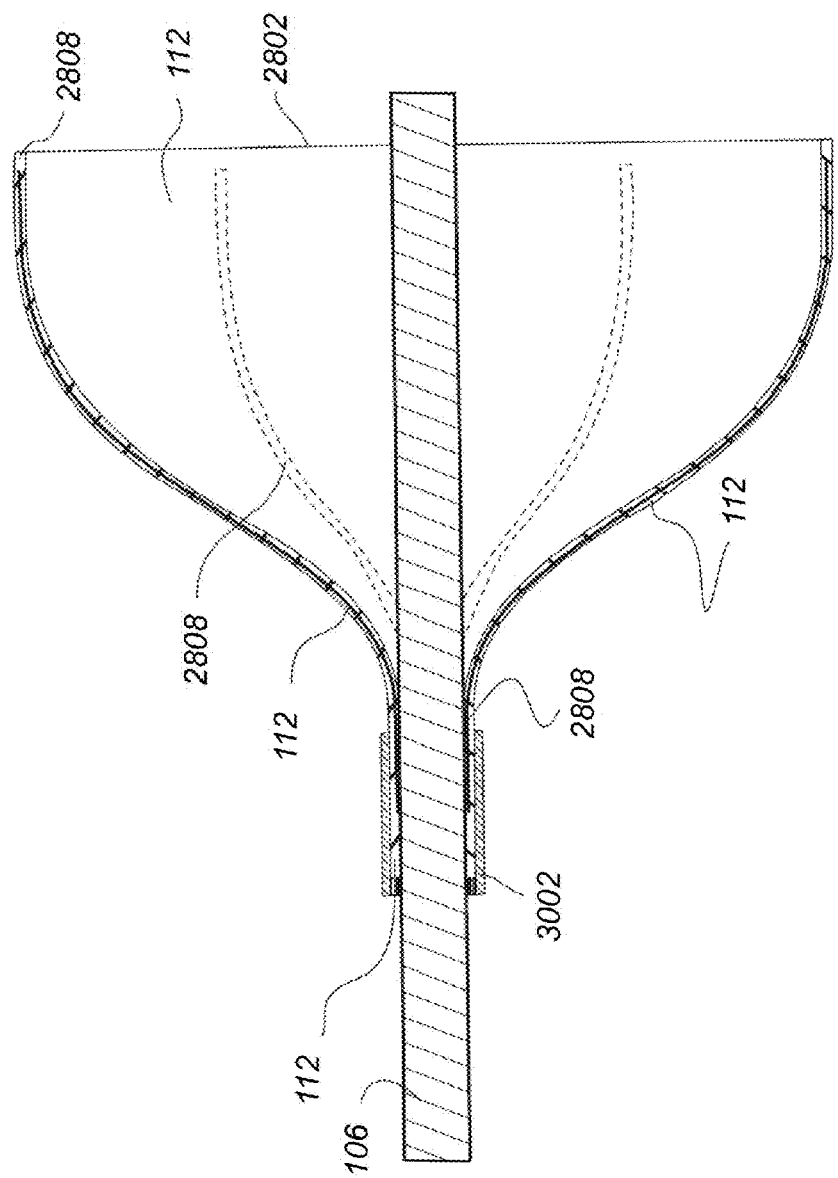
FIGS. 30-31 illustrate membranes for an umbrella-like flow modulation member in accordance with some embodiments of the present invention.
Figure 31:
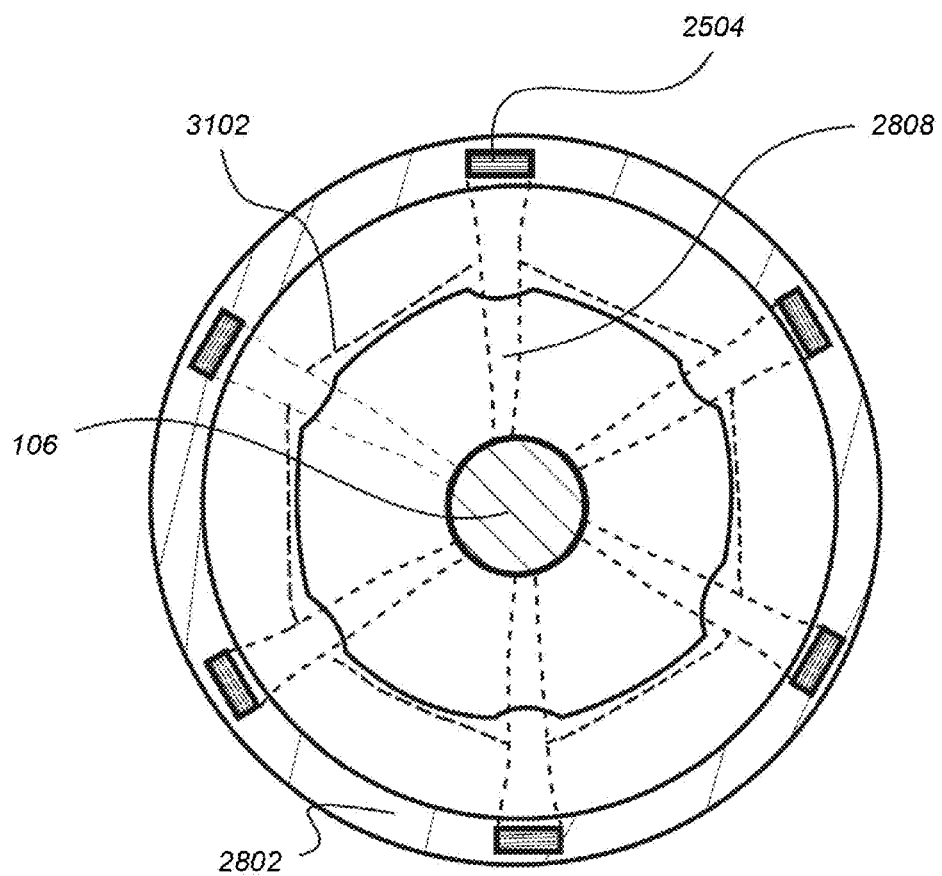

According to preferred embodiments, the membrane material near the distal outer edge of an umbrella-like flow modulation member presents a rounded or even edge to the blood vessel wall. In order to conform to the blood vessel wall, the distal edge of the membrane may also be stiffer, thicker, and/or of a different material than the rest of the membrane. In the embodiment shown in FIG. 28, the distal edge 2802 of the membrane 112 is both stiffer and thicker than the rest of the membrane 112 but still of the same material. This alteration to the distal edge, which might otherwise consist of straight edges stretched between primary struts, conforms the distal edge of the membrane to the latitudinal plane of the blood vessel wall and thus creates a tighter seal. This is illustrated, for example, in FIG. 28 by the curved shape of the distal membrane edge 2802, instead of the straight membrane edges 2804. This form-asserting distal edge may also reduce friction between the flow modulation member and the blood vessel wall, limiting trauma to the blood vessel wall—that is already weakened from the ischemia. In preferred embodiments, and as shown in FIG. 30, the distal edge 2802 of the membrane 112 extends past the distal ends of the struts 2808. In some embodiments, and as shown in FIG. 31, areas of the membrane proximal to the distal edge may be less rounded and instead stretched into straight membrane planes 3102.

In most embodiments, a method is used to connect the membrane to the primary struts that minimizes the possibility of the membrane detaching from the struts during deployment of the flow modulation member. Appropriate methods for attaching the membrane include, but are not limited to adhesion, or encasement of the struts either completely or partially.

Figure 34:
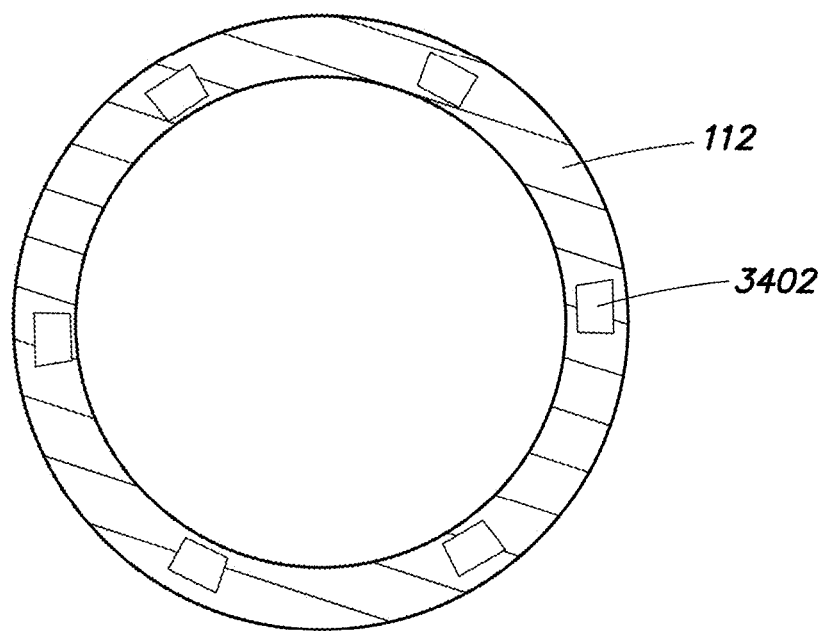
FIG. 34 is a cross-sectional view of an umbrella-like flow modulation member with struts embedded within a membrane in accordance with some embodiments of the present invention.

In preferred embodiments, as shown in FIGS. 30 and 32-33, an umbrella-like flow modulation member 3202 has a membrane 112 that completely encases the struts in the latitudinally expanding regions of the member. Encasement may be accomplished, for example, by melting and molding the plastic around the struts. This is illustrated by section view A-A 3302 in FIG. 33C, as well as FIG. 34, where the struts 3402 appear to be embedded within the membrane 112. As illustrated in FIG. 20, if the struts 2008 and ring-base 2002 are one piece, and if a membrane encases the struts 2008, then the proximal membrane edge may be near the distal edge of the ring-base 2004.

Figure 35:
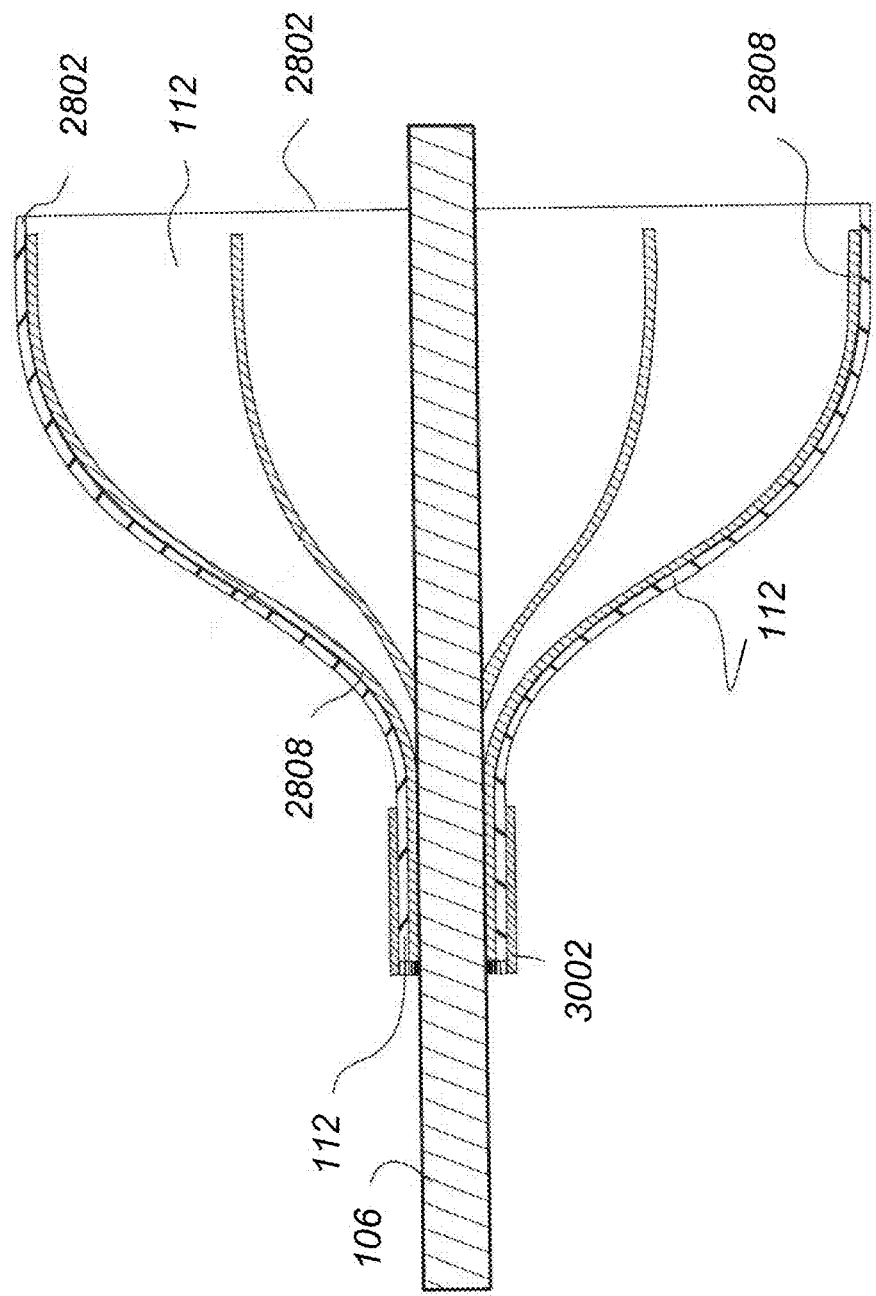
FIG. 35 illustrates an umbrella-like flow modulation member with an attachment ring in accordance with some embodiments of the present invention.

In another attachment solution FIG. 35, an attachment ring 3502 may be a separate piece and made of a material such as steel. The steel attachment ring 3502 is compressed, using swaging, over the proximal ends of the flow modulation member and the pushwire 106. Swaging creates even sealing without heating the nitinol, which would potentially alter the flow modulation member's shape memory.

In alternative embodiments, a membrane may be attached to the outside or inside of the struts of an umbrella-like flow modulation member. The embodiment shown in FIG. 35 shows a membrane 112 attached to the outside of the primary struts 2808. This attachment of a membrane to the outside of the struts may be more efficient from a manufacturing perspective; however, attaching a membrane to the inside of the struts may reduce friction between the membrane and the microcatheter.

In some embodiments, the membrane is tapered to, for example, be thinner at its proximal end. In accordance with the embodiments shown in FIGS. 30 and 35, the membrane 112 may extend toward the proximal end of the struts 2808 and into the hub 3002. The membrane may extend into a ring or a sleeve covering the proximal base of the struts 2808 to create a good seal.

Figure 36A:
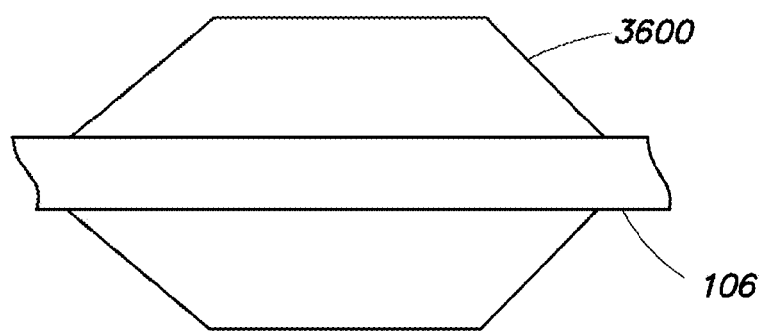
FIGS. 36A-36C illustrate various flow modulation members in accordance with some embodiments of the present invention.
Figure 36B:
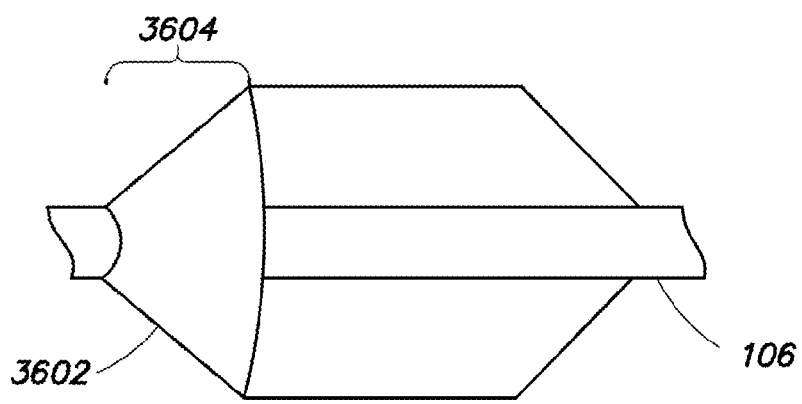
Figure 36C:
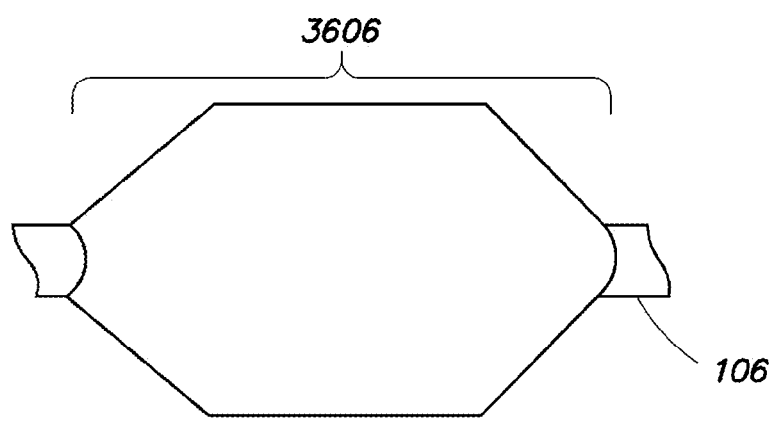

According to some embodiments, the shape or configuration that the flow modulation member's struts make when expanded may be different than an umbrella in appearance. The flow modulation member may take any shape or configuration capable of being deployed and retracted as well as capable of allowing the membrane to modulate blood flow. For example, a flow modulation member where the struts terminate together at the distal end may be used. FIG. 36A illustrates an embodiment of a flow modulation member 3600 with this shape attached to a pushwire 106. Such embodiments pre-establish the placement and centering of the flow modulation system and allow an operator to verify that no sharp edges are making contact with the blood vessel wall. In addition, such embodiments have the advantage of increasing the contact area of the member with the blood vessel wall for greater stability, more easily ensuring a smooth curved contact area of the member with the blood vessel wall, and potentially fortifying the ability of the member to block blood flow. A membrane may cover the entire flow modulation member or a portion—any or a combination of the proximal portion, the distal portion, and the generally cylindrical portion in between—of the flow modulation member struts. In the embodiment shown in FIG. 36B, the membrane 3602 covers the distal portion 3604 of flow modulation member 3600. Meanwhile, in the embodiment shown in FIG. 36C, the membrane 3606 covers the entire flow modulation member 3600.

According to some embodiments, the flow modulation member may be designed so that the distal portion is not covered by a membrane and this uncovered distal portion is deployed before the membrane-covered portion. By deploying the uncovered portion first, an operator may secure the placement and trajectory of the flow modulation member prior to the active occlusion of blood flow. This allows the operator to deploy the membrane-covered portion more rapidly, safely, and confidently. To achieve these different effects across the membrane-covered and uncovered portions of a flow modulation member, the central cylinder portion may use a more pliable pattern than lattice, cellular, or other more rigid patterns. Straight struts, for example, would more easily allow part of the flow modulation member to be released while part remained in the microcatheter. The uncovered portions of the flow modulation member may remain expanded throughout postconditioning. In accordance with certain embodiments, a flow modulation member, particularly the primary struts, may be marked with radiopaque material to distinguish the membrane-covered and uncovered portions of the flow modulation member.

According to other embodiments, a flow modulation member may take the general form of a neurovascular stent. Neurovascular stents have a naturally cylindrical shape that is tangent to the blood vessel wall. A flow blocking membrane could be attached to cover all or part of a stent.

In further embodiments, the flow modulation member is part of the same element as the clot capture member. FIG. 37 shows a series of hybrid clot capture and flow modulation member embodiments. In the embodiment shown in FIG. 37B, a flow-blocking membrane 3702 covers the proximal portion 3704 of a clot capture member. A hybrid clot capture and flow modulation member may be less expensive and may be easier to retract back into the microcatheter and out of the body than multiple separate members. Besides reducing the number of moving parts, a hybrid clot capture and flow modulation member may allow flow modulation closer to the clot.

Figure 37D:
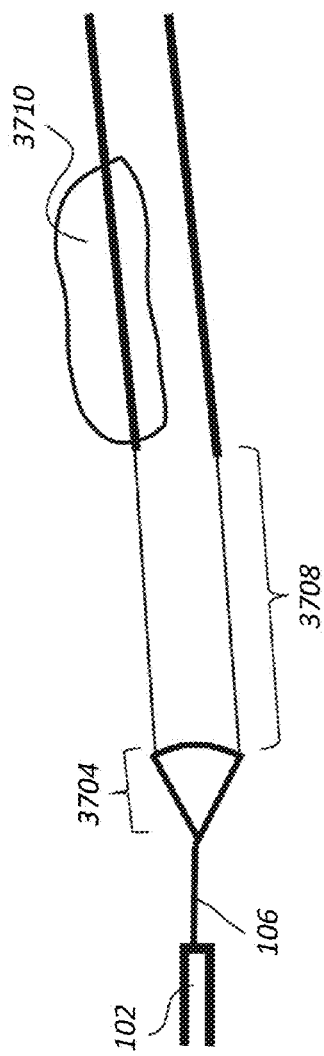
Figure 37E:
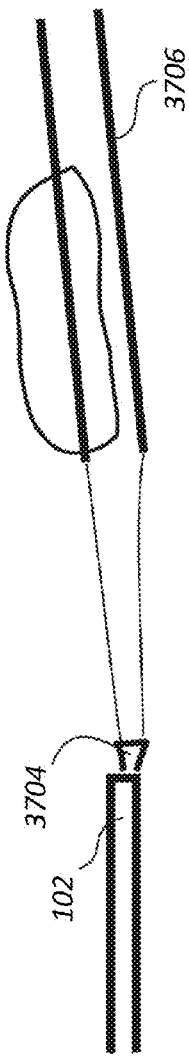

In order to accommodate the membrane, a hybrid clot capture and flow modulation member may need to be longer than a typical clot capture member. FIG. 37C illustrates the distal clot contact area 3706 with this increase in length 3708, which may be, for example, 10 mm. According to most embodiments, the proximal end of a hybrid clot capture and flow modulation member would need to be positioned close enough to the microcatheter so that a minimal push of the microcatheter could re-sheathe the flow-blocking membrane during postconditioning. Additional modifications may be made to allow a hybrid clot capture and flow modulation member to remain partially deployed without significantly deforming the portion of the member in contact with the clot. For example, as illustrated in FIGS. 37D and 37E, an area of the cylindrical portion 3708 between the membrane 3702 and the distal clot 3710 contact area 3706 may be made more structurally flexible or proximally tapered to dissipate the deforming force of re-sheathing on the distal clot contact area 3706.

Clot Capture Members

Embodiments of the clot capture member allow an operator to treat a clot or embolus, usually to effectuate reperfusion. Examples of such treatment include removal (of all, part, or multiple pieces of the clot or embolus), maceration, lysis, compression, pushing, pulling, moving, dissolving, or maintaining in situ. According to some embodiments, a clot capture member may resemble or comprise expandable stent technology, a corkscrew, a jackhammer, a lasso, a loop, a parachute, a filter, a cheese slicer, a vacuum, an inflatable object, a fishing net, a bottle brush, and/or ultrasound technology. The choice of a clot capture member may depend on the conditions of a specific occluded blood vessel.

In certain embodiments, a clot capture member may have acting components that are partially or entirely non-mechanical in nature. A clot capture member may contain for release or be coated by chemical, pharmaceutical or other particular agents, which may act to, for example, lubricate the member, dissolve a clot, loosen a clot, cause a clot to contract, or increase the bonding of a clot with the clot capture member. Such agents may also act on tissue surrounding a clot to, for example, vacillate, heal, minimize reperfusion injury, or minimize infarct size.

According to a preferred embodiment, a clot capture member is based on retrievable stent technology. Retrievable stent technology is especially effective at achieving desired patient outcomes because of its ability to successfully enmesh and drag out large portions of clots. Retrievable stents may also be self-expanding and self-conforming to the size and shape of the blood vessel lumen, thus increasing the simplicity and safety of a clot capture member. Generally, the central body (i.e., the part most likely to contact the clot) of a clot capture member may be cylindrical. The central body may be connected to a pushwire by a plurality of struts. Both the proximal end and/or distal end may be either open, closed, tapered, and/or connected to a pushwire while maintaining an expandable cell structure. In some embodiments, the central body wraps around itself.

Figure 38A:
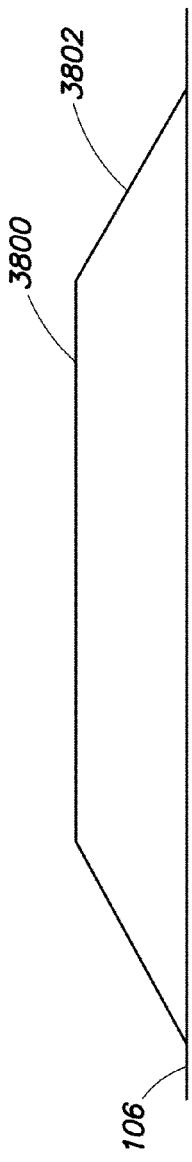
FIGS. 38A-38C and 39 illustrate a clot capture member in accordance with some embodiments of the present invention.
Figure 38B:
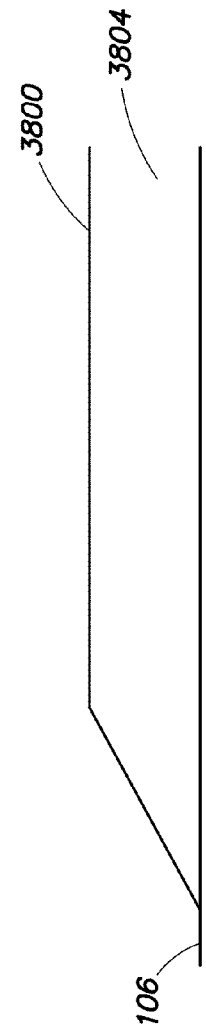
Figure 38C:
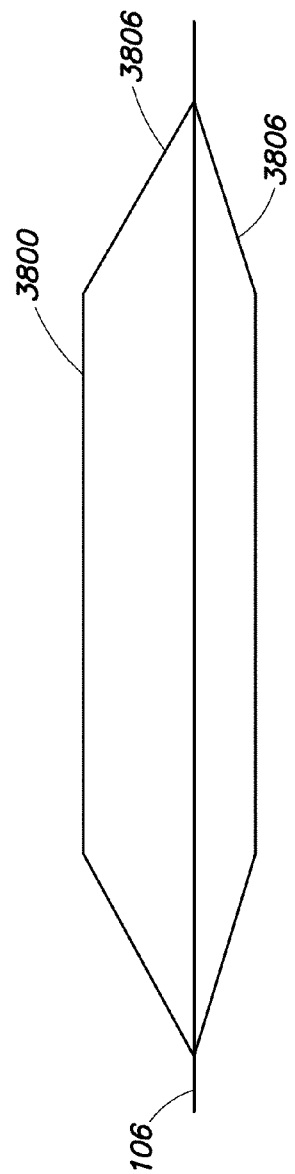
Figure 39:
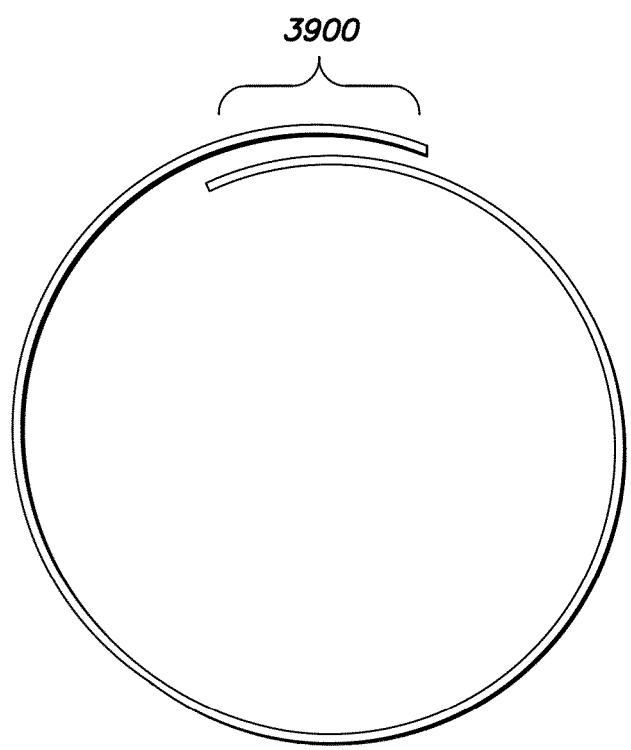

FIG. 38A illustrates an embodiment of the clot capture member with a central body 3800 and closed distal end 3802, both attached to a pushwire 106. Alternatively, FIG. 38B illustrates an embodiment of the clot capture member with a central body 3800 and an open distal end 3804. Meanwhile, FIG. 38C illustrates an embodiment of the clot capture member with a central body 3800 and a plurality of struts 3806. Finally, FIG. 39 illustrates an embodiment of the clot capture member with a central body that is not connected but wraps around itself 3900.

The preferred dimensions of a clot capture member may be varied depending on, among other factors, the radius of the blood vessel, the radius of the clot, and the consistency or resistance of the clot. For example, the length of a clot capture member may range from 1 cm to 5 cm. At full expansion, the radius of a clot capture member may range from 1 mm to 4 mm.

The latitudinal resistive force may vary according to, among other factors; the dimensions of the clot capture member, the dimensions of the struts, and the density of the cells. Also, the latitudinal resistive force may change as the clot capture member expands. Different latitudinal resistive properties may be desirable depending on the condition of the patient and of the clot.

In some embodiments, a clot capture member is manufactured in a manner similar to a neurovascular stent, that is, the pattern of struts is laser-cut from a tube of suitable material, such as nitinol, and then electropolished. Generally, embodiments of the clot capture member may be manufactured using methods and materials described above or known in the art. In preferred embodiments, the expandable cell structure is made from a single piece of nitinol; however, separate pieces and other shape-memory materials, shape-memory alloys, or other super-elastic materials that tend to exert pressure to expand to their set shape may be used (e.g., nickel titanium alloy, stainless steel, or cobalt chrome alloy).

An alternative way of making the capture member is to use separate pieces and attached them using a method such as soldering. Wires, struts, and cell components may be first cut as separate parts and then attached.

The proximal ends of the capture member are attached to the pushwire in a similar manner as the umbrella's struts. In one attachment solution FIG. 35, an attachment ring 3002 may be a separate piece and made of a material such as steel. The steel attachment ring is compressed, using swaging, over the ends of the umbrella's struts 2808 and the pushwire 106. Swaging creates even sealing without heating the nitinol, which would potentially alter the capture member's shape memory.

Figure 40:
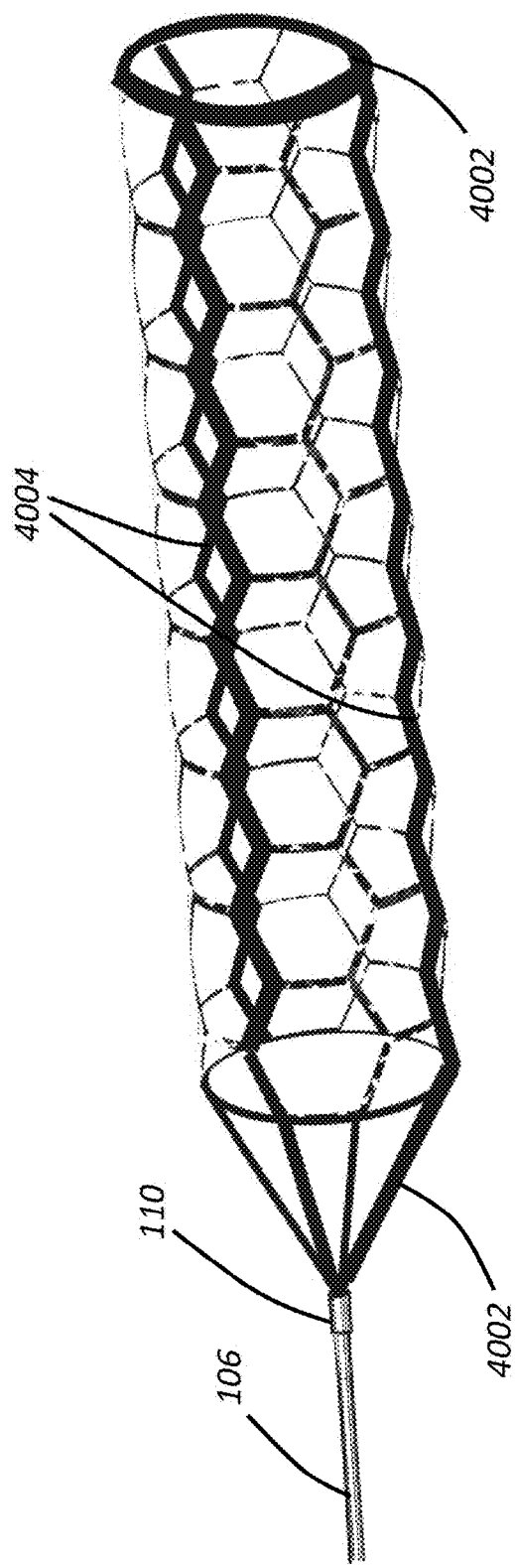
FIG. 40 illustrates a clot capture member with radiopaque markers in accordance with some embodiments of the present invention.

Radiopaque materials may be used to determine relative position, measure expansion, and gauge degree of clot entrapment. Radiopaque materials may include platinum, cobalt, molybdenum, gold, silver, tungsten, iridium, polymers, and combinations of various materials. In a preferred embodiment, as shown in FIG. 40, radiopaque markers 4002 are attached to the proximal and distal ends of a clot capture member, and select cell segments running longitudinally through the central body are covered with a radiopaque coating 4004.

Cell Structures

Denser clots may and often do require multiple passes. This means that several unsuccessful—and time consuming—attempts are made to redeploy the device against the clot. A capture member exerting greater radial force could help the member to grip the clot. A hexagonal cell structure may provide the right amount radial force. The wider angles of a hexagon (in comparison to a diamond) allow the capture member to push against and into the clot more strongly, while still affording enough flexibility to be sheathed within the microcatheter.

The central body of a clot capture member may be composed of various cell structures. Different cell geometries and dimensions (e.g., length, diameter, and pressure) may influence the extent and facility with which a clot capture member engages with a clot. For example, larger cells, especially cells with narrower clot-facing width, may cut through a clot more easily. Meanwhile, smaller cells, especially cells with greater non-clot facing depth, may exert more overall pressure on a clot, tending to compress the clot against the blood vessel wall. Therefore, different cell geometries and dimensions may be desired for different situations, sizes and locations of clots or emboli.

Figure 41:
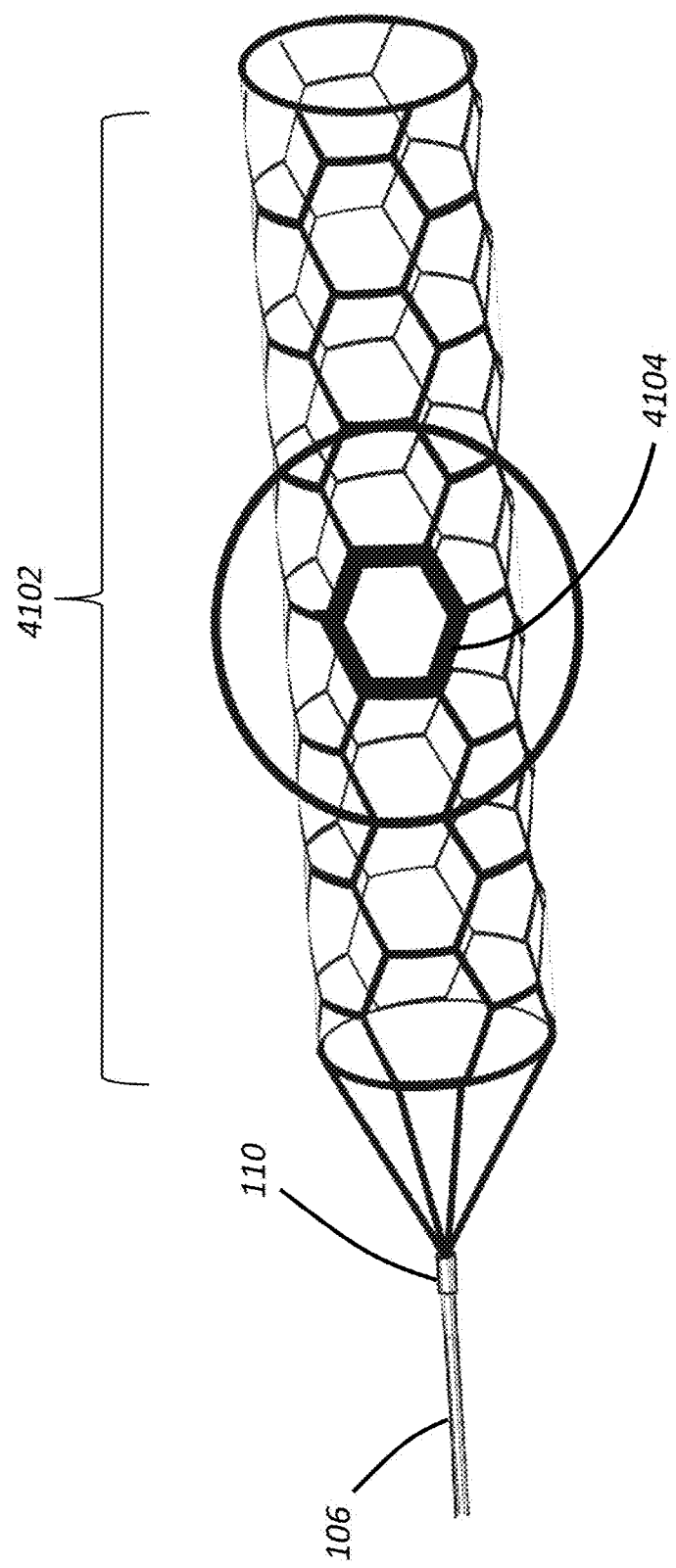
FIG. 41 illustrates a clot capture member with a hexagonal cell pattern in accordance with some embodiments of the present invention.
Figure 42B:
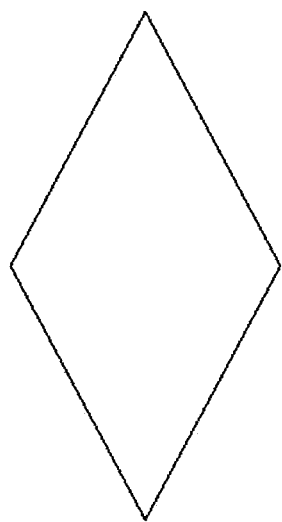
FIGS. 42A-42D illustrate various cell shapes for a clot capture member in accordance with some embodiments of the present invention.
Figure 42D:
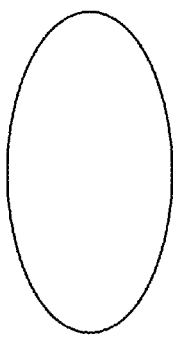
Figure 42A:
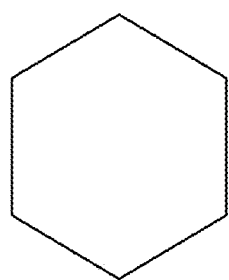
Figure 42C:
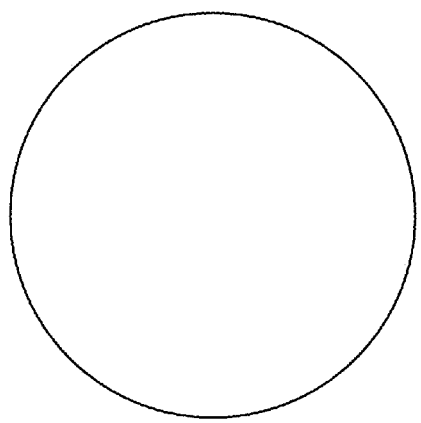
Figure 43:
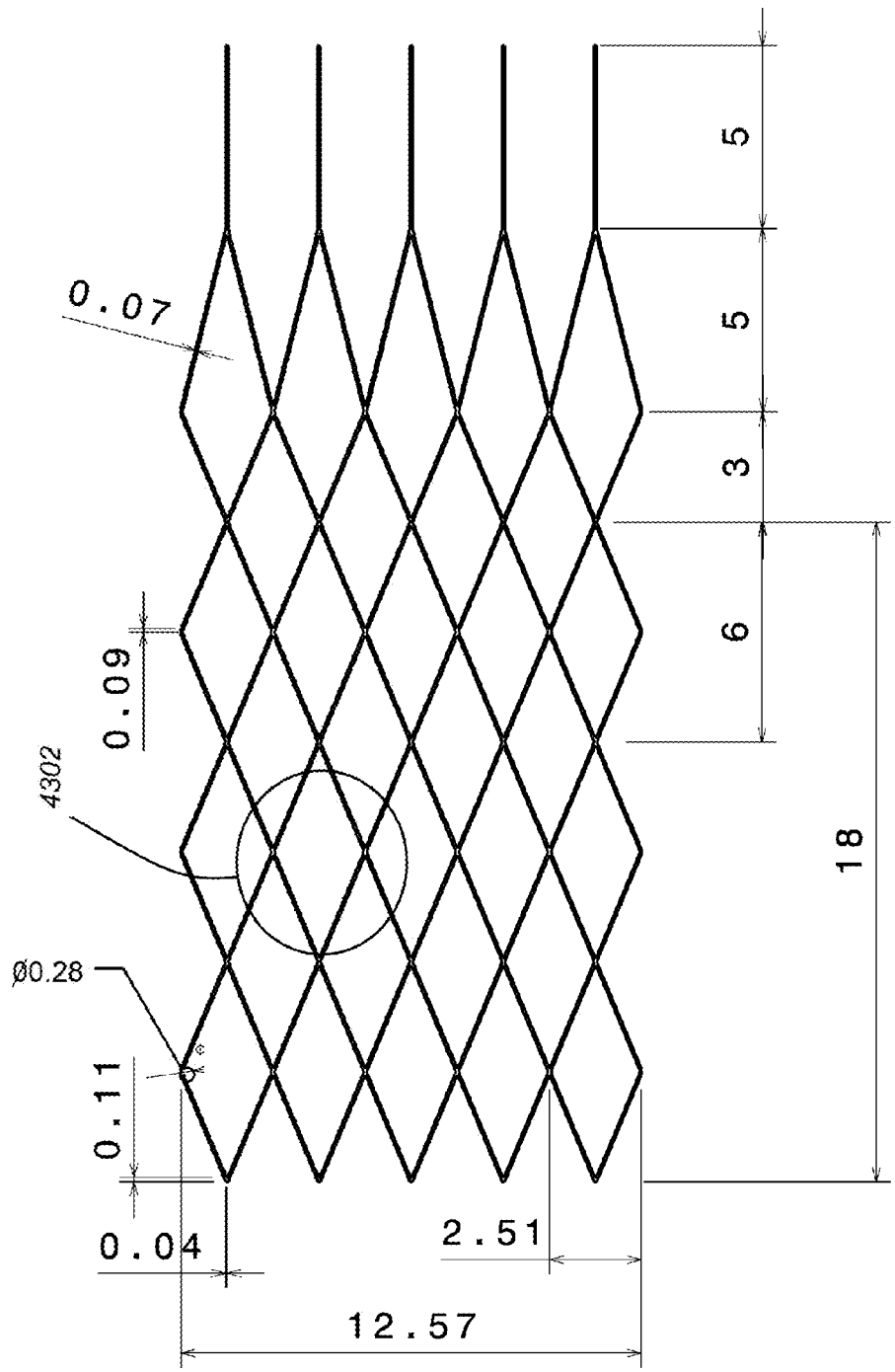
FIGS. 43-44 illustrate two-dimensional cell patterns for a clot capture member in accordance with some embodiments of the present invention.
Figure 44:
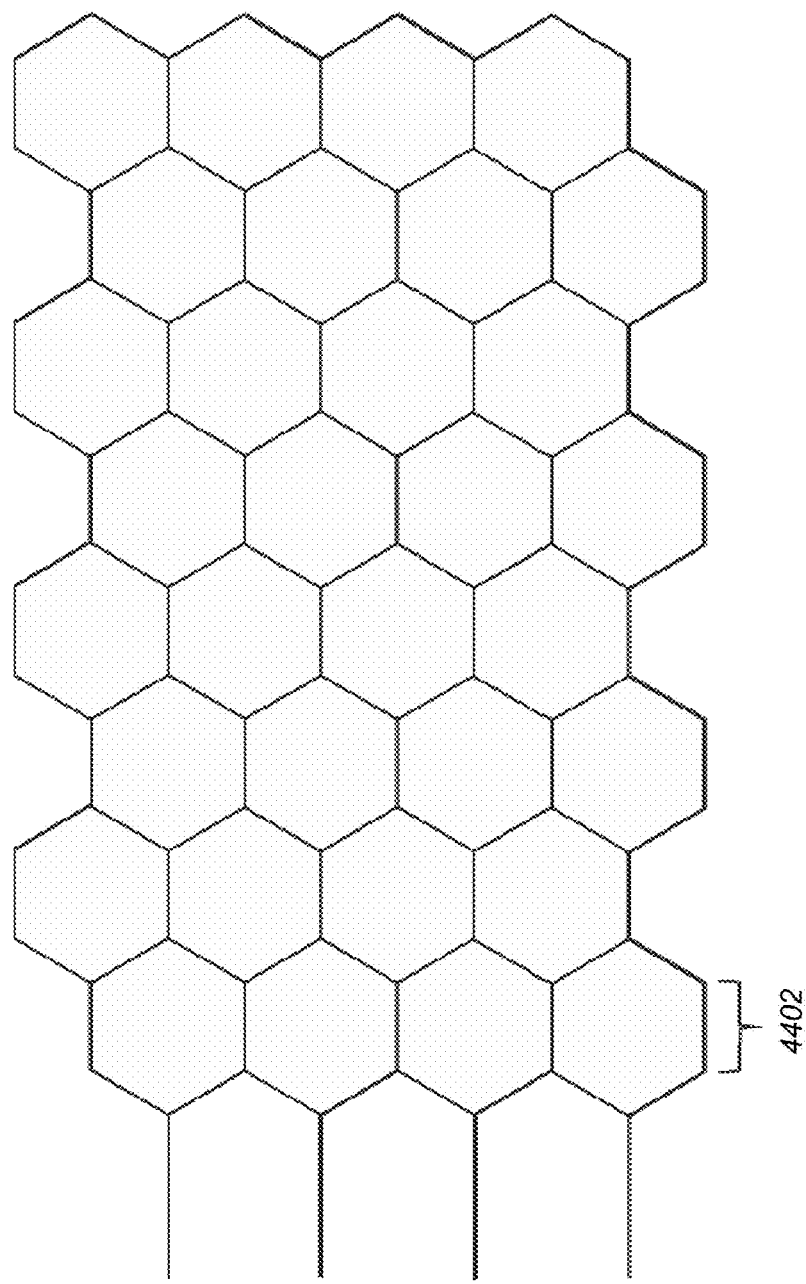

FIG. 41 illustrates a preferred embodiment of the clot capture member with a central body 4102 having a cylindrical structure with a plurality of individual cells 4104. According to some embodiments, the cell pattern may include a hexagon (shown in FIG. 42A), a quadrilateral (shown in FIG. 42B), a circle (shown in FIG. 42C), and/or an oval (shown in FIG. 42D). Accordingly, as shown by a two-dimensional diagram in FIG. 43, a cell structure pattern may include diamond-shaped cells 4302. In some embodiments, the cell structure pattern may resemble off-cycle wave curves. Among the above, embodiments with a hexagonal cell structure, as shown in FIG. 41, may provide superior latitudinal force. A two-dimensional diagram of the same hexagonal cell pattern is shown in FIG. 44. Although the number and dimensions of the cells may vary, the length of one side 4402 of a hexagonal cell in the illustrated embodiment is 1.8 mm. In other embodiments, the cells may be stretched so that the cells are longer across the central longitudinal axis than they are wide.

Figure 45:
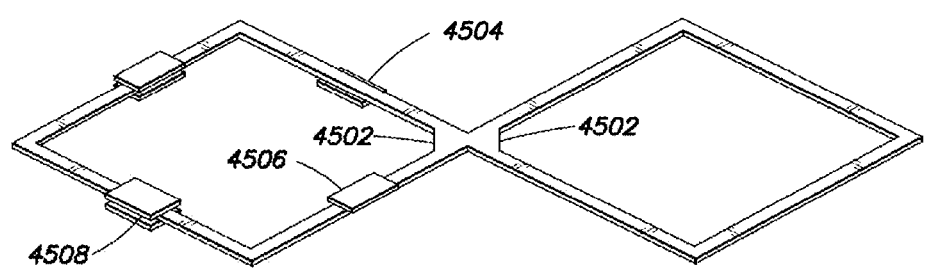
FIG. 45 illustrates a strut junction between two cells in a clot capture member in accordance with some embodiments of the present invention.

Connecting junctions and other thicker parts of cells in a clot capture member may be used and enhanced to facilitate clot adhesion to the member. FIG. 45 illustrates a strut junction 4502 with a greater radius than other parts of the struts and thicker parts, which may be on the outside 4504, the inside 4506, or both 4508 sides of a cell.

Strut Cross-Sections

According to some embodiments, the cross-sectional shape and dimensions of the struts in a clot capture member may vary, both in general and within the same member. For example, the cross-sections of the struts in a clot capture member may be circular, oval, or rectangular. In a preferred and particularly innovative embodiment, a clot capture member uses an arrowhead-shaped strut cross-section to provide significant advantages for clot and embolus retrieval.

The strut cross-sections in a clot capture member may affect the quality of its engagement with a clot. If a clot does not sufficiently adhere to a clot capture member, multiple passes of the member may be required, thus complicating and prolonging the procedure. Even multiple passes do not guarantee successful engagement with a clot and may increase the risks, such as brain damage, associated with stroke. Furthermore, if a clot sufficiently adheres to a clot capture member then emboli may be less likely to break away, migrate downstream, and irretrievably block smaller blood vessels.

In preferred embodiments, the clot capture member has arrowhead-shaped strut cross-sections. Similar to how an arrowhead used for hunting pierces its target easily but is then difficult to dislodge, an arrowhead-shaped, or generally triangular, profile facilitates trapping a clot within the clot capture member by piercing the clot yet providing more resistance to grip the clot after penetration and during retrieval. In most embodiments, the smallest angle (i.e., sharpest point) of the triangular cross-section points laterally outward toward the blood vessel wall (and clot) to facilitate clot penetration.

Numerous variations of an arrowhead-shaped or triangular cross-section may be used, with a few of these modifications exhibited in the embodiments of FIGS. 46A-46K. First, FIG. 46A illustrates an isosceles-triangle embodiment where the lengths of two sides 4600 and the other side 4602 of a triangular cross-section are, for example, 70 µm and 50 µm respectively. FIG. 46B illustrates an arrowhead-shaped embodiment with the same cross-section as the isosceles triangle except for a bend 4606 in the shorter side to increase the width of the inner side of the clot capture member's struts. By providing more contact area on the inside of a clot capture member, clot adhesion and compression may be improved. The same is true for other embodiments with cross-sections having wider base sides, such as the equilateral-triangle embodiment shown in FIG. 46C, the compressed isosceles-triangle embodiment shown in FIG. 46D, the isosceles-trapezoid embodiment shown in FIG. 46E, the concave equilateral-triangle embodiment shown in FIG. 46I, the concave isosceles-trapezoid embodiment shown in FIG. 46J, and the concave half-oval embodiment shown in FIG. 46K. In particular, those embodiments with cross-sections having a bended or concave surface facing the clot capture member's central longitudinal axis may further prevent a clot from migrating away from the member.

Next, FIG. 46F illustrates an isosceles-triangle embodiment where the smallest angle (i.e., sharpest point) 4608, which points laterally outward toward the blood vessel wall, has been dulled. By rounding the sharp edges of a clot capture member in a process such as electropolishing, trauma to the blood vessel walls is minimized. The same is true for other embodiments with cross-sections having dulled points 4608, such as the half-circle embodiment shown in FIG. 46G, the half-oval embodiment shown in FIG. 46H, and the concave half-oval embodiment shown in FIG. 46K.

Figure 47A:
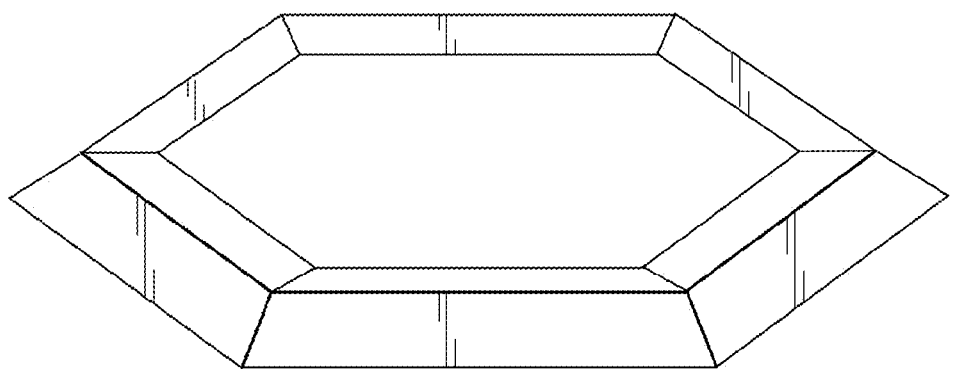
FIGS. 47A-47B are three-dimensional views of clot capture member struts with an isosceles-triangular cross-section in accordance with some embodiments of the present invention.
Figure 47B:
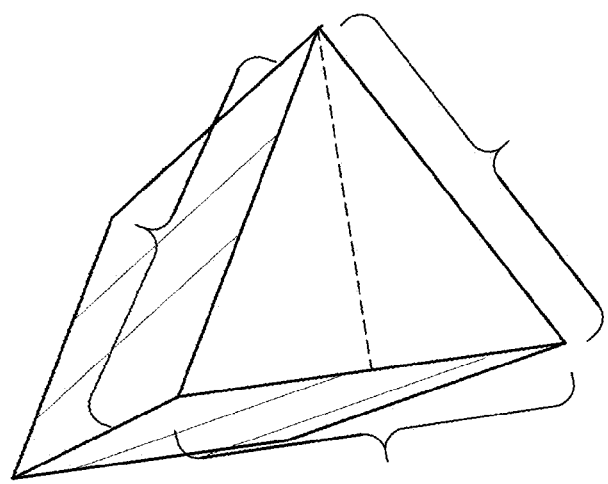

Finally, FIG. 47A illustrates a hexagonal cell for an embodiment of the clot capture member with the isosceles-triangle cross-section shown in FIG. 46A. Meanwhile, FIG. 47B shows a three-dimensional section of strut with the same isosceles-triangle cross-section. The above modifications to the cross-sections may be used alone or in combination in a clot capture member and/or a single strut of a clot capture member.

Applications of Reperfusion and/or Flow Modulation Devices and Systems

Figure 48A:
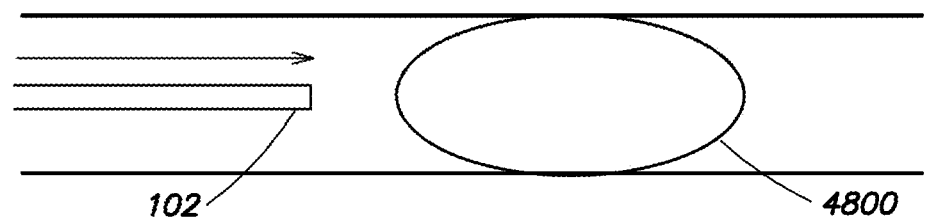
FIGS. 48A-48F illustrate steps for deploying a clot capture member and a flow modulation member in accordance with some embodiments of the present invention.
Figure 48B:
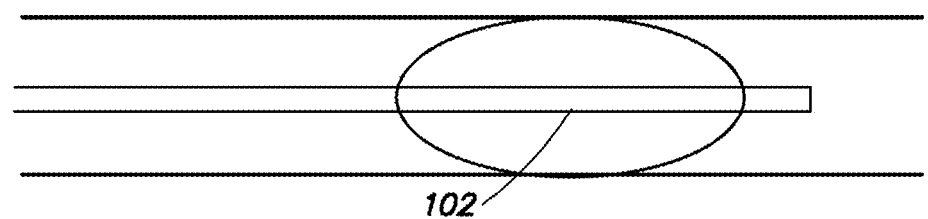
Figure 48C:
Figure 48D:
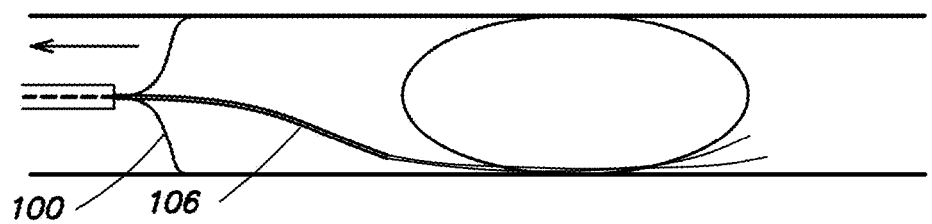
Figure 48E:
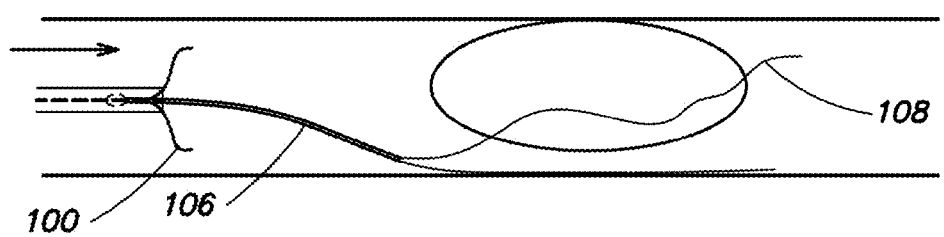
Figure 48F:
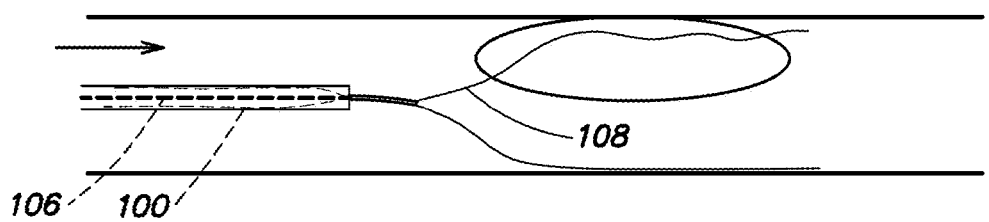

Embodiments of the flow modulation system and its components may be used to perform reperfusion and/or postconditioning procedures. In one embodiment as shown in FIG. 48A, an operator may push a microcatheter 102 to a location proximal to a clot 4800. Then, in FIG. 48B, the operator may push the microcatheter 102 through the clot 4800 so that the distal end of the microcatheter is distal to the clot and the full length of the clot is contacted by the microcatheter. Often, however, the microcatheter 102 follows the path of least resistance and maneuvers around the clot 4800, wedging itself between the clot and the blood vessel wall 114, rather than passing directly through the clot. A pushwire 106 with a flow modulation member 100 and a clot capture member 108 may be positioned within the microcatheter 102. The operator may pull the microcatheter 102 back while the pushwire 106 is held in place, unsheathing both the clot capture member 108 and the flow modulation member 100, which self-expands to occlude blood flow. Meanwhile, the clot capture member 108, which substantially spans the clot 4800 when unsheathed, may begin to self-expand, compressing the clot against the opposing wall of the blood vessel and reopening the occluded vessel for blood flow. Postconditioning may be performed at this point when re-canalization first occurs.

The operator may push the microcatheter 102 to partially re-sheathe the flow modulation member 100 and cause reperfusion. The operator may continue to pull (to open the flow modulation member 100 and decrease flow) and push (to close the flow modulation member 100 and increase flow) the microcatheter 102, while holding the pushwire 106 still, to cyclically modulate blood flow and achieve sufficient postconditioning before allowing natural reperfusion. The operator may facilitate these movements by using a handel or control member, as would be understood by those skilled in the art. The flow modulation member 100 may be either opened or closed before reperfusion begins; however, in a preferred method, the flow modulation member is opened before reperfusion for more precise control over, and knowledge of when, reperfusion and postconditioning begins.

According to an embodiment using the flow modulation member shown in FIG. 18, an operator could push the associated microcatheter forward by 3 mm to transition from having the modulation member fully deployed (blocking blood flow) to having the modulation member completely sheathed (allowing blood flow). In some embodiments, an operator may leave or hold the flow modulation member partially, or not fully, deployed to allow limited blood flow or to minimize friction with the blood vessel wall.

Figure 49A:
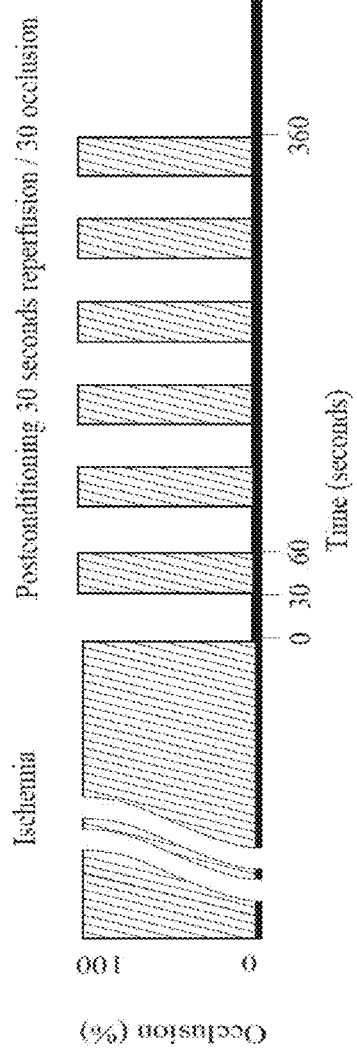
Figure 49B:
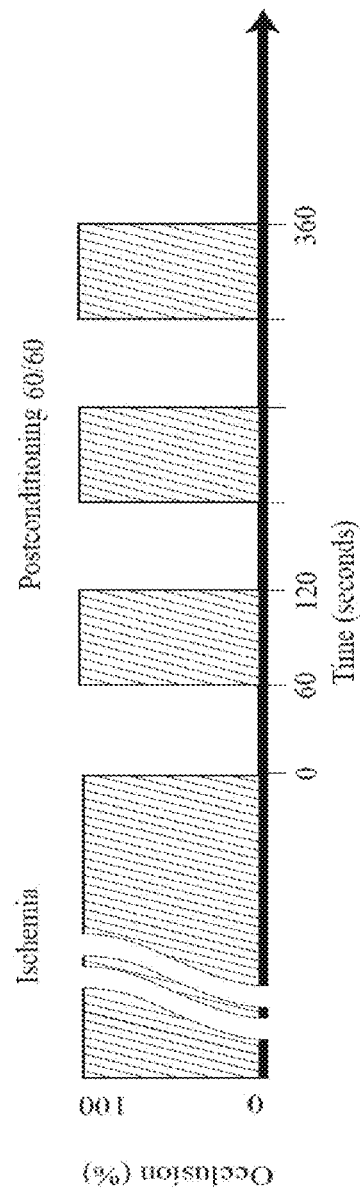
Figure 49E:
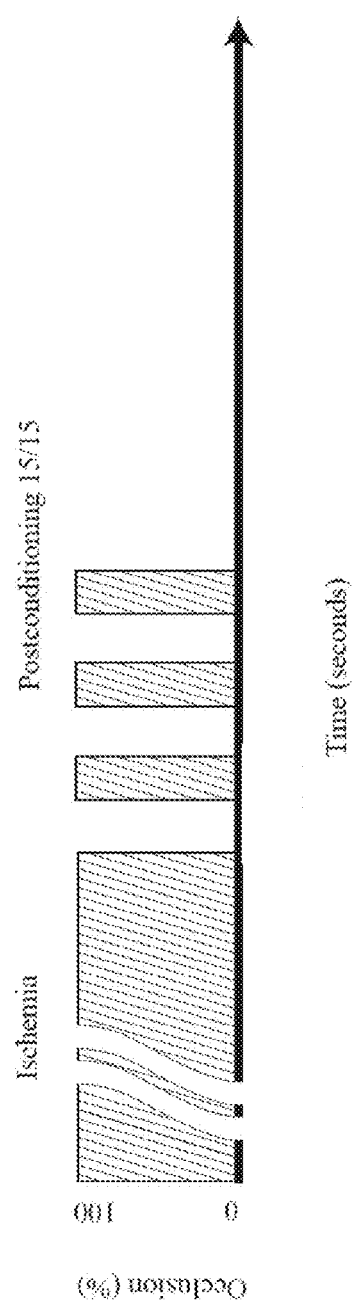
Figure 49F:
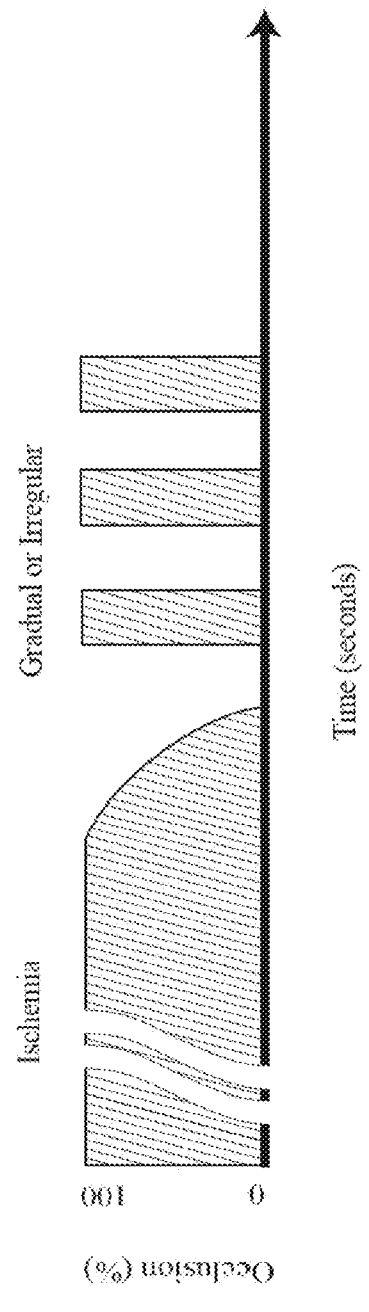
Figure 49I:
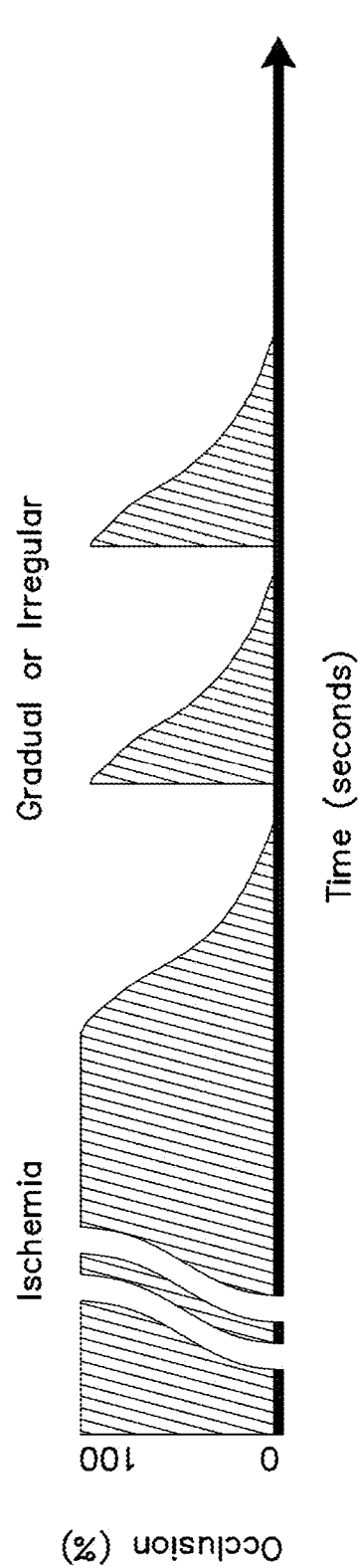
Figure 49J:
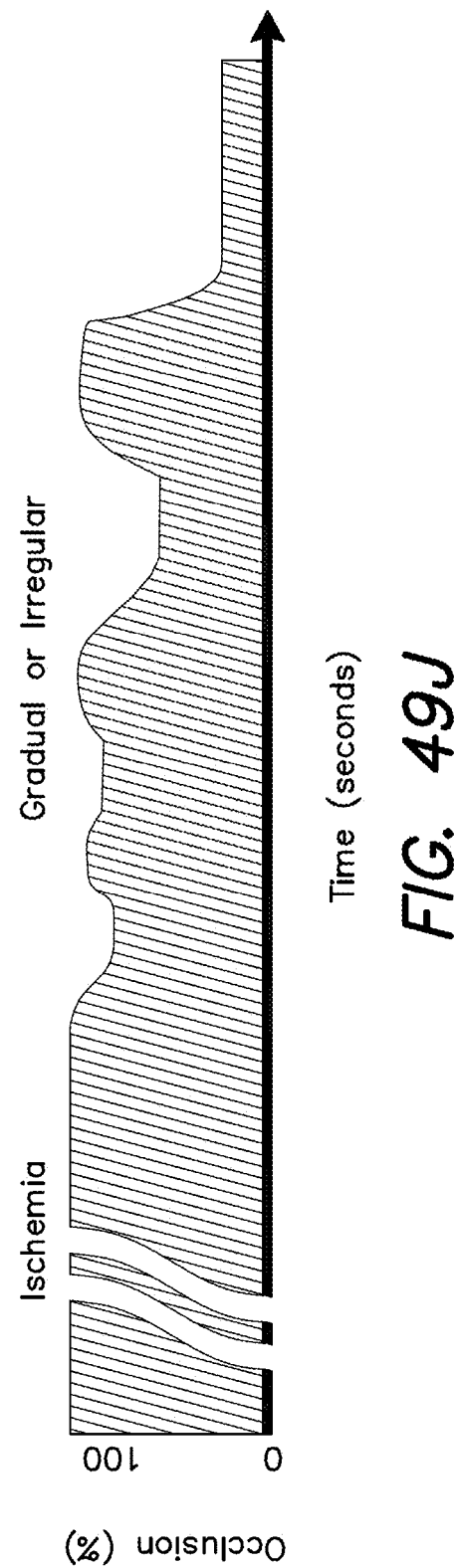

The number and length of the time intervals for postconditioning may vary as determined by the operator. For example, the operator may choose more and/or longer cycle periods when the time from the onset of the ischemia is greater. An example of a desirable interval schedule may be 6 alternating intervals of 30 seconds unblocked 1000 and 30 seconds blocked 1002, as shown in FIG. 49A. Gradual or partial occlusion with a flow modulation member may be used with the examples shown in FIGS. 49F-49J. In particular, FIG. 49J shows a postconditioning schedule where the degree of reperfusion in the blood vessel increases over successive cycles as the clot is being compressed by a clot capture member. Meanwhile, the flow modulation member is deployed gradually for slower and steadier occlusion of a blood vessel, as can be seen from the rounded curves in FIG. 49J. Postconditioning is preferred to be performed as close to the onset of reperfusion as possible. The actual degree of reperfusion achieved, as compared to normal flow rates, may vary depending on the degree to which reperfusion is achieved by the clot capture member or the degree to which occlusion is achieved by the flow modulation member.

Returning to FIG. 48, as the clot capture member 108 continues to self-expand, the metal cells of the member cut through the clot and the clot becomes enmeshed. To aid enmeshment, the operator may partially or fully re-sheathe and unsheathe the clot capture member once or multiple times. Partial re-sheathing advantageously allows the clot capture member to maintain contact with the clot. Once enmeshment is complete and postconditioning is performed (if desired on the current pass) or the time allowed for capture member expansion has elapsed, the operator may push the microcatheter 102 to re-sheathe the flow modulation member 100 and the clot capture member 108 then drag the pushwire 106, microcatheter 102, and the clot down the blood vessel, into a larger catheter, and out of the body.

In some embodiments, an operator uses radiopaque markers as reference points to monitor and gauge the position of members, the state of member expansion, and the appropriate distances to move the microcatheter or pushwire.

In certain embodiments, an operator receives blood flow data, such as the presence of flow. Techniques, such as angiography, which may use contrast agent, may be used.

Embodiments of the flow modulation system or devices may also be used with chemicals, pharmaceuticals, or other agents to, for example: further minimize reperfusion injury, aid in removing a clot, or otherwise benefit a patient's condition. Agents that may minimize reperfusion injury include cyclosporine, sodium-calcium Na2+/Ca2+ exchange inhibitors, monoclonal antibodies, temperature reducing agents, or agents that slow cell metabolism. Agents that may aid in removing a clot include tPA and other agents that aid in dissolving, dislodging, or macerating clots. Agents that may otherwise benefit the patient's condition include pharmaceuticals commonly used for treating clots; agents for treating clots, preventing restenosis, or that commonly coat intravascular devices such as vasodilators; namodopene; sirolimus; paclitaxel; anti-platelet compounds; agents that promote the entanglement or attachment of a clot with a clot capture member; and anticoagulants such as heparin.

According to some embodiments, various parts of the flow modulation system may carry chemicals, pharmaceuticals, or other agents. For example, an umbrella-shaped flow modulation member or a capture member may be coated with an agent. In a preferred method, an agent is held within the hollow space inside the umbrella, between the pushwire and the membrane.

Any patents, publications, or other references mentioned in this application for patent are hereby incorporated by reference.

As will be apparent to one of ordinary skill in the art from a reading of this disclosure, the present disclosure can be embodied in forms other than those specifically disclosed above. The particular embodiments described above are, therefore, to be considered as illustrative and not restrictive. Those skilled in the art will recognize, or be able to ascertain, using no more than routine experimentation, numerous equivalents to the specific embodiments described herein. The scope of the present invention is as set forth in the appended claims and equivalents thereof, rather than being limited to the examples contained in the foregoing description.

The invention claimed is:

1. An apparatus comprising:
 a catheter,
 a balloon disposed on the catheter in the vicinity of a distal end of the catheter, the catheter including an orifice for inflating the balloon,
 a stent attached to a distal end of a wire that extends through a lumen of the catheter and configured to be deployed at a clot location when pushed through an open distal end of the catheter,
 the stent having an open distal end and a closed proximal end, the open end of the stent configured to expand to the shape of a vessel wall when deployed to engage the clot, the closed end of the stent configured to remain closed and attached to the distal end of the wire when deployed;
 a sealing interface between the wire and the lumen, that is adapted to seal the lumen so that the balloon may be inflated;
 wherein the sealing interface includes an outwardly facing surface on the wire and an inwardly facing surface on the lumen; and
 wherein the sealing surface of the lumen engages with the outwardly facing surface on the wire via friction;
 wherein the stent is configured to be deployed through the open distal end of the catheter when the wire is translated distally relative to the catheter and the lumen is sealed;
 wherein the stent is configured to be re-sheathed into the catheter when the wire is pulled proximally relative to the catheter.

2. The apparatus of claim 1 wherein the outwardly facing surface of the wire has a larger diameter than other portions of the wire.

3. The apparatus of claim 1, wherein the catheter includes an inner surface,
 wherein the sealing interface includes a sealing ring,
 wherein the sealing ring is sized to sealingly engage the inner surface of the catheter so that when engaged the sealing ring substantially blocks flow of fluid through the catheter.

4. The apparatus of claim 3 wherein the apparatus is capable of transporting fluid that contains one or more of the following: contrast agent, tissue plasminogen activator PA, cyclosporine, calpain inhibitors, sodium-calcium Na+/Ca2+ exchange inhibitors, monoclonal antibodies, temperature reducing agents, agents that slow cell metabolism, plasminogen activator, agents that may aid in removing a clot agents that aid in dissolving, dislodging, or macerating clots, pharmaceuticals or compounds commonly used for treating clots, preventing restenosis, intravascular device coatings such as vasodilators, namodopene, sirolimus, paclitaxel, anti-platelet compounds and agents that promote the entanglement or attachment of a clot with a clot capture member such as fibronectin.

5. An assembly configured to treat ischemia in a patient, comprising:
 a catheter with a proximal region, a distal region with an open distal end, and a single lumen;
 a flow modulation member coupled to the proximal region of the catheter and comprising an inflatable balloon able to reversibly decrease and increase the flow of fluid through the blood vessel at least twice, and thereby modulate blood flow through the blood vessel, wherein the inflatable balloon has a balloon inflation aperture continuous with the single lumen and able to receive inflating fluid from the single lumen;
 a pushwire with a proximal end and a distal end, wherein the pushwire is at least partially within the single lumen;
 a flow restoration member for increasing the flow of blood through the clot when deployed through the open distal end of the catheter, coupled to the distal end of the pushwire
 wherein a distal end of the flow restoration member is configured to expand to the shape of a vessel wall to engage the clot when deployed, and a proximal end of the flow restoration member is configured to remain coupled to the distal end of the pushwire when deployed; and
 one or more sealing members adapted to decrease or stop the flow rate of inflating fluid leaving the single lumen
 wherein the pushwire and the flow restoration member are configured to translate distally relative to the lumen to deploy the flow restoration member through the open end of the catheter when the sealing members decrease or stop the flow rate of inflating fluid leaving the single lumen;
 wherein the pushwire is configured to be withdrawn proximally relative to the lumen to re-sheath the flow restoration member.

6. The assembly of claim 5, wherein one of the one or more sealing members is made of an electro-active compound, whereby applying and/or altering an electric current applied to the pushwire causes the electro-active sealing member to expand so as to provide more resistance to the flow of fluid through the catheter, wherein the flow modulation member is capable of expanding to produce a desired seal.

7. The assembly of claim 6 wherein the assembly is adapted to operate with a pressure of the fluid less than 5 atm.

8. The assembly of claim 6, wherein the flow restoration member for increasing the flow of blood through a blood vessel beyond a clot comprises a self-expanding scaffold, adapted to engage a clot in a blood vessel.

9. The assembly of claim 6, wherein the catheter comprises a first section in the proximal region and a second section in the distal region, the area in the second section of the lumen, in the plane normal to the central axis of the catheter, being smaller than the area in the first section of the lumen, in the plane normal to the central axis of the catheter.

10. The assembly of claim 6, wherein the one or more sealing members comprise a protrusion with an outwardly facing surface attached to the pushwire at a location on the pushwire proximal to the flow restoration member, wherein the protrusion slows the flow of fluid through the lumen when the protrusion engages an inwardly facing surface at the distal region of the catheter.

11. The assembly of claim 6, wherein the one or more sealing members comprise a sealing tip at the distal end of the catheter, wherein a luminal edge of the sealing tip comes in close proximity with a sealing surface of the pushwire and slows the flow of fluid through the lumen when the sealing surface of the pushwire is placed through the sealing tip.

12. The assembly of claim 11, wherein the sealing tip allows the flow restoration member to pass the sealing tip when the catheter is translated relative to the pushwire.

13. The assembly of claim 5, wherein the flow modulation member further comprises a plurality of self-expanding struts.

14. The assembly of claim 5, wherein the device is capable of transporting fluid that contains one or more of the following: contrast agent, tissue plasminogen activator (tPA), cyclosporine, calpain inhibitors, sodium-calcium Na+/Ca2+ exchange inhibitors, monoclonal antibodies, temperature reducing agents, agents that slow cell metabolism, plasminogen activator, agents that may aid in removing a clot agents that aid in dissolving, dislodging, or macerating clots, pharmaceuticals or compounds commonly used for treating clots, preventing restenosis, intravascular device coatings such as vasodilators, namodopene, sirolimus, paclitaxel, anti-platelet compounds and agents that promote the entanglement or attachment of a clot with a clot capture member such as fibronectin.

\* \* \* \* \*